US007595159B2

(12) United States Patent
Scherzer et al.

(10) Patent No.: US 7,595,159 B2
(45) Date of Patent: Sep. 29, 2009

(54) PREDICTION OF PARKINSON'S DISEASE USING GENE EXPRESSION LEVELS OF PERIPHERAL BLOOD SAMPLES

(75) Inventors: Clemens R. Scherzer, Newton, MA (US); Steven R. Gullans, Natick, MA (US); Roderick Jensen, Pelham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 261 days.

(21) Appl. No.: 11/266,774

(22) Filed: Nov. 3, 2005

(65) Prior Publication Data
US 2006/0134664 A1 Jun. 22, 2006

Related U.S. Application Data

(60) Provisional application No. 60/645,423, filed on Jan. 19, 2005, provisional application No. 60/624,592, filed on Nov. 3, 2004.

(51) Int. Cl.
C12Q 1/68 (2006.01)
G01N 33/53 (2006.01)
C12P 19/34 (2006.01)
C07H 21/04 (2006.01)

(52) U.S. Cl. .......................... 435/6; 435/7.1; 435/7.24; 435/91.2; 435/287.2; 536/24.31

(58) Field of Classification Search ........................ None
See application file for complete search history.

(56) References Cited

FOREIGN PATENT DOCUMENTS

WO  WO 02/057496    7/2002
WO  WO 03/074654    9/2003

OTHER PUBLICATIONS

Pusztai and Hess. Clinical trial design for microarray predictive marker discovery and assessment. Annals of Oncology, vol. 15, pp. 1731-1737, 2004.*
Golub et al. Molecular classification of cancer: Class discovery and class prediction by gene expression monitoring. Science, Bol. 286, pp. 531-537, Oct. 1999.*
Bahn et al., "Gene expression profiling in the post-mortem human brain—no cause for dismay," *J Chem. Neuroanat.*, 22:79-94, 2001.
Balazs et al., "Molecular typing of HLA-A, -B, and DRB using a high throughput micro array format," *Human Immunology*, 62(8):850-857, 2001.
Campbell et al., "Assessment of normal variability in peripheral blood gene expression," *Disease Markers*, 18(4):201-206, 2002.
Caronti et al., "Reduced dopamine in peripheral blood lymphocytes in Parkinson's disease," *Neuroreport.*, 10:2907-2910, 1999.
Chabas et al., "The influence of the proinflammatory cytokine, osteopontin, on autoimmune demyelinating disease," *Science*, 294:1731-1735,2001.
Chea, "T Test finds ovarian cancer early: Bethesda firm's invention could provide reliable screening," Washington Post, p. A02, Feb. 8, 2002.
Citron et al., "Excessive production of amyloid beta-protein by peripheral cells of symptomatic and presymptomatic patients carrying the Swedish familial Alzheimer disease mutation," *Proc. Natl. Acad. Sci. USA*, 91:11993-11997, 1994.
Davies et al., "Consensus report of the working group on: 'Molecular and biochemical markers of Alzheimer's disease,'" *Neurobiology of Aging*, 19(2):109-116, 1998.
Di Luca et al., "Platelets as a peripheral district where to study pathogenetic mechanisms of alzheimer disease: the case of amyloid precursor protein," *Eur. J. Pharmacol.*, 405:277-283, 2000.
Endo et al., "HLA system in senile dementia of Alzheimer type and multi-infarct dementia in Japan," *Arch Gerontol Geriatr*, 5(1):51-6, 1986.
Ferrer et al., "Glycogen synthase kinase-3 is associated with neuronal and glial hyperphosphorylated tau deposits in Alzheimer's disease, Pick's disease, progressive supranuclear palsy and corticobasal degeneration," *Acta Neuropathol. (Berl)*, 104:583-591, 2002.
GenBank Accession No. D83043. Feb. 6, 1999.
Gerhold et al., "Better therapeutics through microarrays", *Nat Genet*, 32:547-551, 2002.
Gordon et al., "Translation of microarray data into clinically relevant cancer diagnostic tests using gene expression ratios in lung cancer and mesothelioma", *Cancer Res*, 62:4963-4967, 2002.
Grünblatt, "The benefits of microarrays as tools for studying neuropsychiatric disorders," *Drugs of Today*, 40(2):147-156, 2004.
Guo et al., "Oligonucleotide arrays for high-throughput SNPs detectino in the MHC class I genes: HLA-B as a model system," *Genome Research*, 12(3):447-457, 2002.
Hughes et al., "Accuracy of clinical diagnosis of idiopathic Parkinson's disease: a clinico-pathological study of 100 cases," *J. Neurol. Neurosurg. Psychiatry*, 55:181-184, 1992.
Ibarreta et al., "Distinct pH homeostatic features in lymphoblasts from Alzheimer's disease patients," *Ann. Neurol.*, 44:216-222, 1998.
Kalchman et at, "HIP1, a human homologue of *S. cerevisiae* Sla2p, interacts with membrane-associated huntingtin in the brain," *Nat. Genet.*, 16:44-53, 1997.
Kalchman et al., "Huntingtin is ubiquitinated and interacts with a specific ubiquitin-conjugating enzyme," *J. Biol. Chem.*, 271:19385-19394, 1996.
Kamme et al., "Single-cell microarray analysis in hippocampus CA1: demonstration and validation of cellular heterogeneity," *J. Neurosci.*, 23:3607-3615, 2003.
Kim et al., "Association of vitamin D receptor gene polymorphism and Parkinson's disease in Koreans," *J. Korean Med. Sci.*, 20:495-498, 2005.

(Continued)

*Primary Examiner*—Christopher S. F. Low
*Assistant Examiner*—Jennifer Dunston
(74) *Attorney, Agent, or Firm*—Fulbright & Jaworski, LLP

(57) ABSTRACT

The present invention identifies a number of gene markers whose expression is altered in neurodegenerative diseases (ND). These markers can be used to diagnose or predict ND in subjects, and can be used in the monitoring of therapies. In addition, these genes identify therapeutic targets, the modification of which may prevent ND development or progression.

19 Claims, 13 Drawing Sheets
(9 of 13 Drawing Sheet(s) Filed in Color)

OTHER PUBLICATIONS

Li et al., "The amyloid precursor protein of Alzheimer disease in human brain and blood," *J. Leukoc. Biol.*, 66:567-574, 1999.

Loring et al., "A gene expression profile of Alzheimer's disease," *DNA and Cell Biology*, 20(11):683-695, 2001.

Middleton et al., "Frequency of HLA-A and B alleles in early and late-onset Alzheimer's disease," *Neurosci Lett.*, 262(2):140-2, 1999.

Mootha et al., "Identification of a gene causing human cytochrome c oxidase deficiency by integrative genomics," *Proc. Natl. Acad. Sci. USA*, 100:605-610, 2003.

Pasinetti et al., "From epidemiology to therapeutic trials with anti-inflammatory drugs in Alzheimer's disease: the role of NSAIDs and cyclooxygenase in beta-amyloidosis and clinical dementia," *J. Alzheimers Dis.*, 4:435-445, 2002.

Petricoin et al., "Use of proteomic patterns in serum to identify ovarian cancer", *Lancet*, 359:572-577, 2002.

Radich et al., "Individual-specific variation of gene expression in peripheral blood leukocytes," *Genomics*, 83(6):980-988, 2004.

Rebhan et al., *GeneCards: encyclopedia for genes, proteins and diseases*, Rehovot, Israel, 1997. Trends in Genetics, 13(4):163.

Reed et al., "HLA antigens in Alzheimer's disease," *Tissue Antigens*, 21(2):164-167, 1983.

Renvoize, "An HLA and family study of Alzheimer's disease," *Psycho Med.*, 14(3):515-20, 1984.

Scherzer et al., "Gene expression changes presage neurodegeneration in a Drosophila model of Parkinson's disease," *Hum. Mol. Genet.*, 12:2457-2466, 2003.

Scherzer et al., "Loss of apolipoprotein E receptor LR11 in Alzheimer disease," *Arch Neurol.*, 61:1200-1205, 2004.

Scherzer et al., "Simplifying complex neurodegenerative diseases by gene chip analysis," In: *Principles of Molecular Neurosurgery*, Freese et al. (Eds.), *Prog. Neurol Surg. Basel, Karger*, 18:1-12, 2004.

Schlossmacher et al., "Detection of distinct isoform patterns of the beta-amyloid precursor protein in human platelets and lymphocytes," *Neurobiol. Aging*, 13:421-434, 1992.

Shin et al., "Expression patterns of alpha-synuclein in human hematopoietic cells and in *Drosophila* at different developmental stages," *Mol. Cells*, 10:65-70, 2000.

Slonim, "From patterns to pathways: gene expression data analysis comes of age," *Nat. Genet.*, 32(suppl):502-508, 2002.

Sorkina et al., "Constitutive and protein kinase C-induced internalization of the dopamine transporter is mediated by a clathrin-dependent mechanism," *Traffic*, 6:157-170, 2005.

Sunada et al., "Differential expression of the parkin gene in the human brain and peripheral leukocytes," *Neurosci. Lett.*, 1998;254:180-182, 1998.

Tusher et al., "Significance analysis of microarrays applied to the ionizing radiation response," *Proc. Natl. Acad. Sci. USA*, 98:5116-5121, 2001.

van't Veer et al., "Gene expression profiling predicts clinical outcome of breast cancer," *Nature*, 415:530-536, 2002.

Wang et al., "Vitamin D(3) attenuates 6-hydroxydopamine-induced neurotoxicity in rats," *Brain Res.*, 904:67-75, 2001.

Whitney et al., "Individuality and variation in gene expression patterns in human blood," *Proceedings of the National Academy of Sciences of the United States of America*, 100(4):1896-1901, 2003.

Wittliff and Erlander, "Laser capture microdissection and its applications in genomics and proteomics," *Methods Enzymol.*, 356:12-25, 2002.

Auluck et al., "Chaperone suppression of alpha-synuclein toxicity in a *Drosophila* model for Parkinson's disease," *Science*, 295(5556):865-868, 2002.

Barbanti et al., "Increased expression of dopamine receptors on lymphocytes in Parkinson's disease," *Movement Disorders*, 14(5):764-771, 1999.

Caronti et al., "Dopamine transporter immunoreactivity in peripheral blood lymphocytes in Parkinson's disease," *J. Neural. Transm.*, 108:803-807, 2001.

Flower et al., "Heat shock prevents alpha-synuclein-induced apoptosis in a yeast model of Parkinson's disease," *J. Mol. Biol.*, 351:1081-1100, 2005.

Grünblatt et al., "Gene expression analysis in *N*-methyl-4-phenyl-1,2,3,6-tetrahydropyridine mice model of Parkinson's disease using cDNA microarray: effect of *R*-apomorphine," *Journal of Neurochemistry*, 78:1-12, 2001.

Hauser et al., "Expression profiling of substantia nigra in Parkinson's disease, progressive supranuclear palsy, and frontotemporal dementia with Parkinsonism," *Arch Neurol*, 62:917-921, 2005.

Höhfeld et al., "Hip, a novel cochaperone involved in the eukaryotic Hsc70/Hsp40 reaction cycle," *Cell*, 83:589-598, 1995.

Klucken et al., "Hsp70 reduces α-Synuclein aggregation and toxicity," *The Journal of Biological Chemistry*, 279(24):25497-25502, 2004.

Miller et al., "α-Synuclein in blood and brain from familial Parkinson disease with *SNCA* locus triplication," *Neurology*, 62:1835-1838, 2004.

Nollen et al., "Modulation of in Vivo HSP70 chaperone activity by Hip and Bag-1," *The Journal of Biological Chemistry*, 276(7):4677-4682, 2001.

Scherzer and Feany, "Yeast genetics targets lipids in Parkinson's disease," *TRENDS in Genetics*, 20(7):273-277, 2004.

Sunada et al., "Differential expression of the parkin gene in the human brain and peripheral leukocytes," *Neuroscience Letters*, 254:180-182, 1998.

* cited by examiner

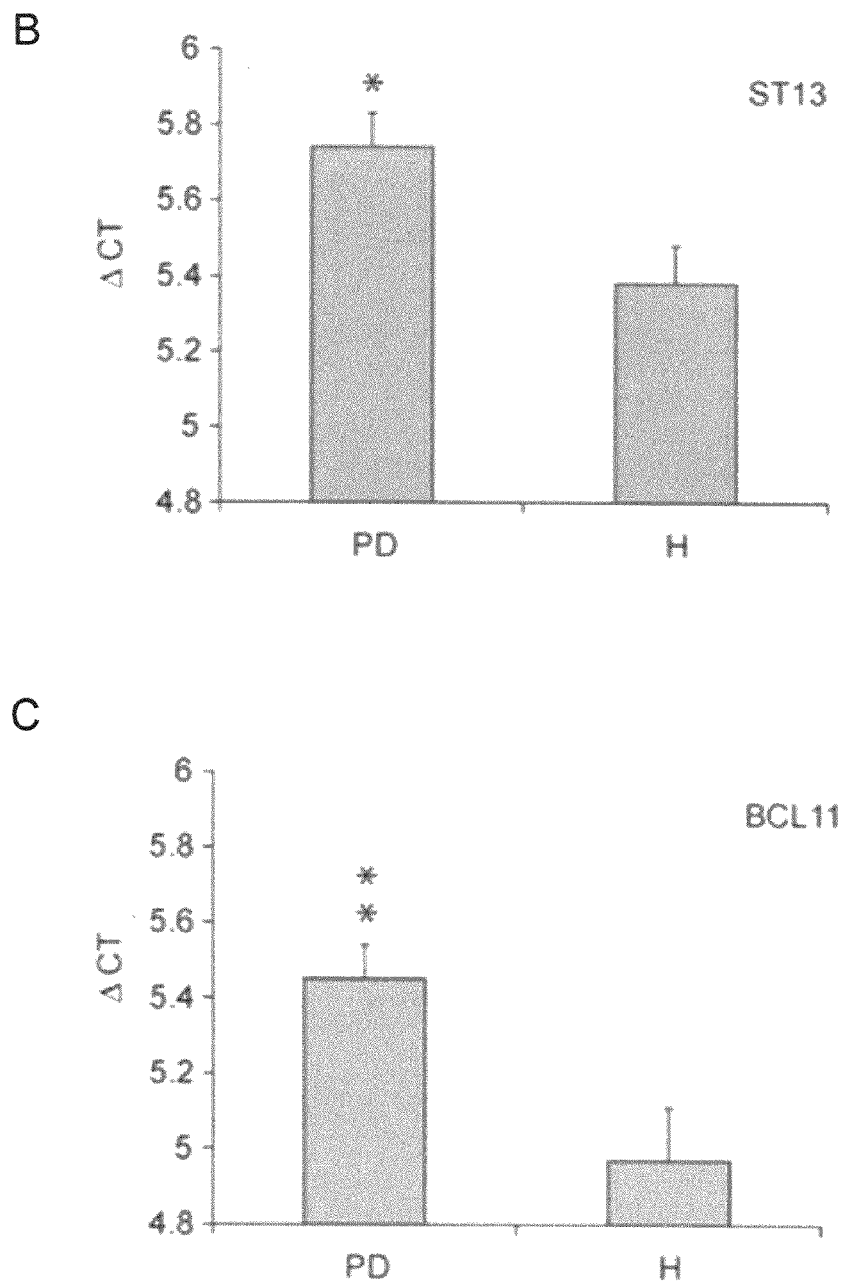
FIG. 2B-C

US 7,595,159 B2

PREDICTION OF PARKINSON'S DISEASE USING GENE EXPRESSION LEVELS OF PERIPHERAL BLOOD SAMPLES

This application claims benefit of priority to U.S. Provisional Application Ser. No. 60/645,423, filed Jan. 19, 2005, and U.S. Provisional Application Ser. No. 60/624,592, filed Nov. 3, 2004, the entire contents of which are hereby incorporated by reference.

BACKGROUND OF THE INVENTION

1. Field of the Invention

The present invention relates generally to the fields of molecular biology, genomics, immunology and neurobiology. More particularly, it concerns the identification of specific genes that are dysregulated in patients afflicted with neurodegenerative diseases (ND). These genes can be used to identify subjects suffering from or at risk of NDs, and can also provide targets for ND therapies.

2. Description of Related Art

Genes for many autosomal dominant or recessive neurodegenerative diseases have been already identified. However, little is known about the complex genetics behind the vast majority of sporadic or 'idiopathic' neurodegenerative diseases. These diseases are likely to be caused by the combinatorial effect of several susceptibility genes acting in concert with environmental risk factors. Identifying the relevant genes, elucidating their molecular function, and defining targets for neuroprotective drugs pose great challenges and will require novel scientific methodologies. These genetic strategies will help to bring the benefits of the recent genomic revolution to the clinic and the operating room, by developing treatment strategies for neurodegenerative diseases.

Traditional scientific approaches have always focused on serial studies of one gene at a time. For complex diseases that are caused by a multiplicity of susceptibility genes, high-throughput analysis of many genes in parallel is a more efficient and informative approach, though cost considerations have been a major problem in the past. Gene chips or 'microarrays' attach probes for transcripts of tens of thousands of genes onto a rigid support such as a glass slide and permit a comprehensive genome-wide analysis of transcript changes. However, such comprehensive gene listings for neurodegenerative diseases have yet to be established.

SUMMARY OF THE INVENTION

Thus, in accordance with the present invention, there is provided a method of predicting whether a subject is or will be afflicted with a neurodegenerative disease (ND) comprising (a) obtaining an mRNA- or protein-containing sample from said subject; (b) determining expression information for one or more genes/gene products from the group consisting of those set forth in Tables 1-5; (c) comparing expression information for said selected genes/gene products with the expression information of the same genes/gene products in a subject not afflicted with ND; and (d) predicting whether said subject is or will be afflicted with ND.

The expression information for more one gene/gene product in the group of claim 1(b) may be determined, for example, for at least 2, 3, 4, 5, 6, 7, 8, 9, 10, 12, 15, 20, 25, 30, 35, 40, 45, 50, 60, 70, 80, 90 or 100 genes/gene products from Tables 1-5. The sample may comprise peripheral blood-derived mononuclear cells. The ND may be Parkinson's Disease, Alzheimer's Disease, Progressive Supranuclear Palsy, multiple system atrophy, corticobasal degeneration Huntington's Disease, or dementia with Lewy bodies.

The expression information is determined from a nucleic acid (e.g., mRNA) by multiplex PCR of transcripts, northern blot., reverse trancription PCR (RT-PCR), microarray analysis of mRNA transcripts (e.g., a plurality of oligonucleotides dispersed on the surface of a chip or wafer), or RNAse protection. Alternatively, expression information is determined by examining proteins by immunohistochemistry, ELISA or western blot.

In another embodiment, there is provided a chip or wafer comprising a nucleic acid microarray, wherein said nucleic acids hybridize to target transcripts or cDNAs for a plurality of genes set forth in Tables 1-5. The number of genes may be 2, 3, 4, 5, 6, 7, 8, 9, 10, 12, 15, 20, 25, 30, 35, 40, 45, 50, 60, 70, 80, 90, 100 more. The chip may be comprised of polymers, plastics, resins, polysaccharides, silica or silica-based materials, fiberoptic materials, carbon, metals, inorganic glasses, or nitrocellulose. The nucleic acids may be cDNAs or oligonucleotides. Oligonucleotides may be in the range of about 10 to about 50 base pairs or less in length.

In yet another embodiment, there is provided a method for monitoring a therapy for a neurodegenerative disease (ND) comprising (a) obtaining an mRNA-containing sample from a subject receiving said therapy; (b) determining expression information for one or more genes comprising Tables 1-5; and (c) comparing expression information for said selected genes with the expression information of the same genes in an ND subject not receiving said therapy. The ND may be Parkinson's Disease, Alzheimer's Disease, Progressive Supranuclear Palsy, multiple system atrophy, corticobasal degeneration Huntington's Disease, dementia with Lewy bodies.

The expression information is determined from a nucleic acid (e.g., mRNA) by multiplex PCR of transcripts, northern blot., reverse trancription PCR (RT-PCR), microarray analysis of mRNA transcripts (e.g., a plurality of oligonucleotides dispersed on the surface of a chip or wafer), or RNAse protection. Alternatively, expression information is determined by examining proteins by immunohistochemistry, ELISA or western blot. The sample may be peripheral blood.

The method may further comprise modifying said therapy based upon the altered expression of one or more of said selected genes, and the method may further comprise making a prediction on the efficacy of treating the subject from which said sample was obtained. The ND subject not receiving said therapy may be the same subject prior to receiving said therapy. The method may further comprise determining expression information for said selected genes from said subject at multiple time points.

In still yet another embodiment, there is provided a method for determining the efficacy of a therapy for a neurodegenerative disease (ND) comprising (a) obtaining an mRNA- or protein-containing sample from a subject receiving said therapy; (b) determining expression and/or functional information for one or more selected genes/proteins selected from the group consisting of Tables 1-5; (c) comparing expression and/or functional information for said one or more selected genes/proteins with the expression information of the same gene or genes in an ND subject not receiving said therapy; and (d) determining the efficacy of said therapy based on the ability of said therapy to alter the expression and/or function of said one or more genes/proteins.

In a further embodiment, there is provided a method for treating a neurodegenerative disease (ND) comprising administering to a subject with ND a drug that normalizes the expression level or activity of a gene product listed in Tables 1-5.

In an even further embodiment, there is provided a method of predicting whether a subject develop a severe form of neurodegenerative disease (ND) comprising (a) obtaining an mRNA-containing sample from said subject; (b) determining expression information for one or more genes from the group consisting of those set forth in Tables 1-5; (c) comparing expression information for said selected genes with the expression information of the same genes in a subject afflicted with ND that does or does not progress to a severe from of ND; and (d) predicting whether said subject will progress to a severe form of ND.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

(FIG. 1A) Expression data matrix of eight marker genes of 66 blood samples from PD and control subjects (right panel). Each row represents a blood sample, and each column represents a gene. As shown in the color bar, overexpression is displayed in red, and underexpression in green. Blood samples are ordered by their risk score (left panel), which is defined as the correlation with the average profile of the PD group minus the correlation with the average profile of the controls. The molecular marker correctly ranked 29 out of the 31 PD samples (93%) at the top of the list (high risk scores). 26 out of the 35 controls (74%) received low risk scores and were ranked at the bottom of the list. Solid lines designate tertiles of risk score values. The clinical diagnosis for each individual is shown on the right. (FIG. 1B) Validation of the risk marker on independent test samples confirms that high scores are significantly associated with increased PD risk (P for trend=0.04). Same as for FIG. 1A, but the expression data matrix is for 39 independent samples. (FIG. 1C) The ROC curve in the test set (blue curve) is highly consistent with the ROC curve for the leave-one-out cross-validated (LVOOCV) marker in the training set (grey) confirming the risk prediction observed for different cutoffs. The nominal ROC curve in the training set represents an upper limit (red). (FIG. 1D) Dopamine replacement medication does not bias the risk score. There is no difference in risk scores of PD patients on dopamine medication versus unmedicated de novo patients (mean±SE, 0.06±0.04 and 0.11±0.1, respectively; P=0.96). Average risk scores are low (negative) in healthy controls (−0.24±0.04) and neurodegenerative disease controls (AD, −0.25±0.05; PSP, −0.19±0.06; multiple system atrophy (MSA), −0.34±0.17; corticobasal degeneration (CBD), −0.26; essential tremor (ET), −0.15). ND, denotes neurodegenerative disease control; H, denotes healthy control; error bars indicate standard errors.

FIGS. 2A-C. Discovery of genes differentially expressed in PD compared to healthy controls. (FIG. 2A) 24 probe sets, assaying 22 unique genes, are significantly differentially expressed in cellular blood of 31 PD patients (including five de novo PD patients) compared to healthy controls (FDR=0.03). Dopamine replacement status (DRT) is displayed (pink bar, de novo PD patients; black bar, PD patients on DRT). Expression matrices as in FIGS. 1A-D except that genes here are shown on the vertical axis. Notably in this comparison all genes are underexpressed in PD. The majority of PD patients are at early stages of the disease process as indicated by the Hoehn and Yahr (H&Y) scale. The label H&Y "2" here is used to designate patients with either stage 2 (bilateral disease) or 2.5 (bilateral disease with mild postural imbalance). Dendrograms illustrate genes with similar expression patterns by cluster analysis. (FIG. 2B) and (FIG. 2C), underexpression of the HSP70-interacting protein gene (ST13) in the ubiquitin-proteasome pathway and the BCL11B gene in the apoptosis pathway in PD is confirmed by real time PCR in large age-, sex-, and blood count-matched samples (n=51 and 45, respectively; P=0.025 and P=0.005, respectively by t-test). Delta cycle thresholds (ΔCT) are displayed. In PD patients, ST13 and BCL11B amplify at higher ΔCTs than in controls confirming lower abundance of ST13 and BCL11B mRNA. Fold changes were 0.78 for ST13 and 0.72 for BCL11B. GAPD was used as internal control gene to account for input mRNA quantity.

(FIG. 3A) 21 genes were differentially expressed in AD and (FIG. 3B) 12 in PSP compared to healthy controls (FDR=0.04 and 0.07, respectively). COX2 (PTGS2), a prostaglandin cyclooxygenase implicated in the disease process (Pasinetti, 2002), was most highly overrepresented in blood of AD patients (2.2 fold). (FIG. 3C) COX2 overexpression was replicated by real-time PCR (n=17; fold change=1.4; ΔD, ΔCT 6.93±0.10 (mean±SE); H, ΔCT 7.48±0.17; P=0.014). GSK3A (b), one of two human glycogen synthase kinase-3 isoforms implicated in PSP (Ferrer et al., 2002), was among the genes overexpressed in PSP patients by microarray. (FIG. 3D) Genes differentially transcribed in AD or PSP patients cluster in the related biological processes of prostaglandin synthesis, lysosomal function, and immune response, in addition to processes also perturbed in PD. The relative abundance of known genes in each biological process is displayed.

(FIG. 5A) Distribution of Pearson correlations between all genes (probe sets) and the actual class labels (red) or 1000 random permutations of the class labels (blue). (FIG. 5B) Number of observed probe sets with absolute Pearson correlation above the effective threshold in 1000 permutations of class labels, where the effective threshold is the lowest absolute correlation of a probe set used in the eight-gene PD risk marker (0.4725). Only four of 1000 random permutations resulted in $\geq 8$ genes in the PD risk marker. On average, 0.62 genes are expected by chance alone to have a correlation with PD status at this correlation threshold. The probability of discovering eight genes with correlations equal or greater than those observed for the eight marker genes purely by chance was 0.004 based on 1000 random permutations.

DESCRIPTION OF ILLUSTRATIVE EMBODIMENTS

Figure 1A:
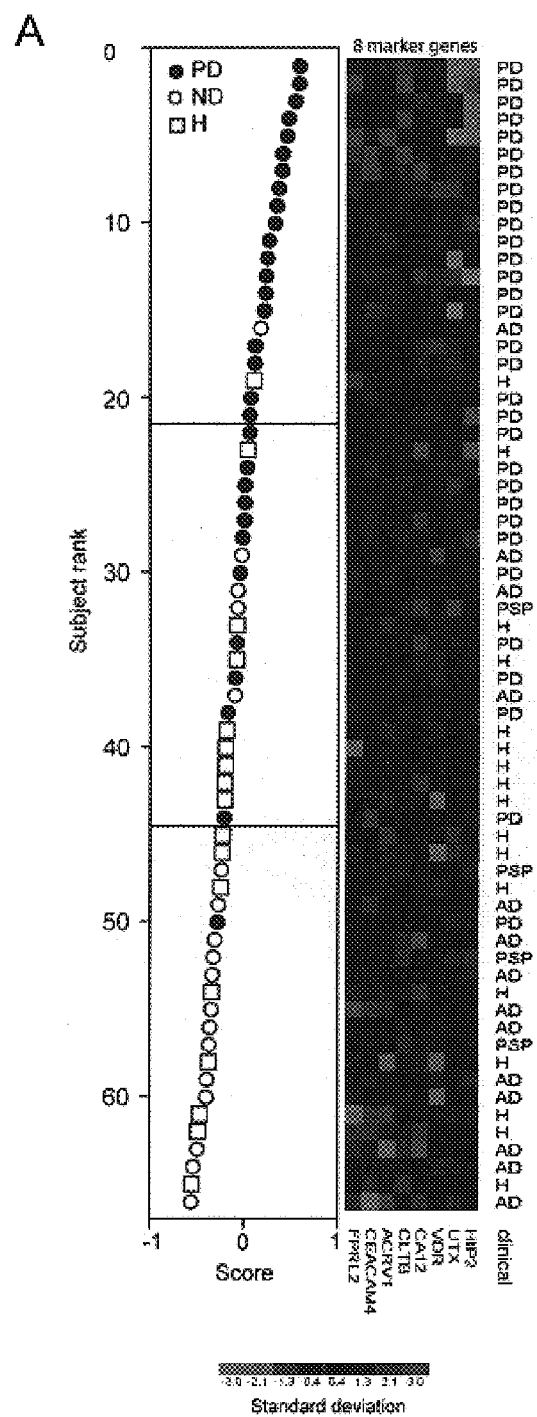
FIGS. 1A-D. Molecular markers associated with PD risk.
Figure 1B:
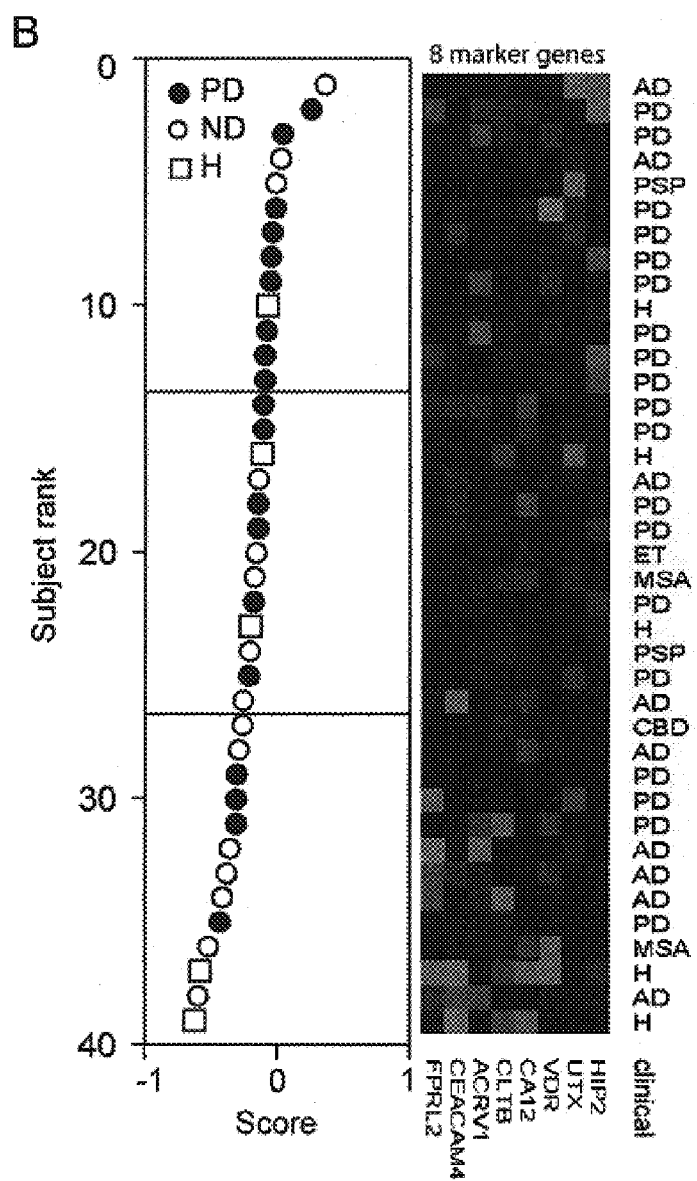

Many investigators propose the use of a combination of microarrays, bioinformatics, and simple validation experiments to define a short list of one to ten high-priority candidate genes. A stepwise filtering process is generally applied to the initial microarray datasets. The present inventors typically start with error models tailored to the specific microarray platforms, to optimize quantification of the gene expression levels. They also recommend a stringent three-step statistical analysis to minimize false positives due to biological or technical variation and to correct for multiple testing.

First, a selective intensity filter is applied to exclude genes with low hybridization signal intensities, because false-positive results are particularly high for low-intensity genes. With Affymetrix gene arrays, they generally require that the gene 'Average Difference' or 'Signal' be greater that the 'Target Intensity' (defined as the trimmed-mean expression level on the array) for at least one sample in the study. This will focus further analysis on the 30-40% most abundant transcripts.

Second, a ratio threshold (generally-fold changes of >1.5-2.0) is applied to eliminate small changes in expression that are of unclear technical and biological significance. Although smaller fold-changes may be statistically significant they are very difficult to verify by other means (e.g., quantitative polymerase chain reaction with reverse transcription; RT-PCR).

Finally, a t-like test statistic is used to identify genes that are expressed differentially on the basis of confidence values or P values (Slonim, 2002). Permutation tests (e.g., Significance Analysis of Microarrays, Tusher et al., 2001) are performed to estimate the significance of the test statistic and to correct for multiple testing. The number of false positives expected by chance alone is determined by repeatedly permuting the samples' class labels and computing t statistics for all genes in the scrambled data.

To qualify each gene further after the primary microarray assessment, a secondary screen may be required to independently confirm the observed changes in gene expression. If the primary screen results in a relatively short list (less than fifty genes), quantitative RT-PCR can be performed (on samples) for technical validation. Investigators may further prioritize genes as candidate targets on the basis of their organismal roles; for example, hormones may be favored as potential therapeutic proteins, or receptors or enzymes that are amenable to modulation by small-molecule drugs may be chosen (for further study). For genes with unknown or unclear functions, prioritizing those of greatest physiological relevance requires further analysis such as quantitative RT-PCR or protein expression analysis. Western blot or immunohistochemistry are preferred for protein analysis, but an antibody is not always readily available. The secondary screening process may obtain a more detailed dissection of the biological process using time series, more diverse biological samples, and anatomical specificity.

Secondary screens become labor intensive, time consuming, and expensive if a large list of genes need be confirmed. Therefore, the inventors have begun to use multiple microarray platforms for efficient technical validation of large numbers of differentially expressed genes. Different high-density oligonucleotide platforms (e.g., Affymetrix, Amersham, Agilent) spot distinct probes for the genes interrogated and have distinct technical advantages and weaknesses. The results suggest that for the more highly expressed transcripts, 70-80% of the >2-fold gene expression changes are concordant when the same RNA sample is run on Affymetrix and Amersham arrays. In the inventors' opinion, the current optimal secondary screen takes advantage of two independent high-density oligonucleotide platforms in a cross-validation strategy that the inventors term 'shotgun' or sequential microarray analysis.

When using microarrays to identify differentially expressed genes, it is important to recognize the inherent error caused by technical and biological variations. Reproducibility and sensitivity problems can generate both falsenegative and false-positive results. But these issues can be addressed readily through robust experimental design, rigorous statistical analysis, the use of biological and technical replicates, and independent verification by quantitative RT-PCR or other microarray platforms. Although microarrays represent a powerful tool for forming initial hypotheses, it is essential to consider the limitations of interpreting biological responses through measurements of mRNA abundance alone. Measurements of mRNA do not directly reflect protein quantities, enzyme activities, or extranuclear signal transduction. Microarray experiments also may fail to resolve true "modifier genes" from homeostatic responses that attempt to restore the original state of the system. Generally, microarray measurements fail to resolve cause from effect. Thus, successful use of microarray technology requires that sources of error be controlled carefully in the design and execution of experiments.

The primary microarray screen will identify a shortlist of high-priority modifier candidates. Each type of selective profiling identifies differentially expressed genes characteristic for a particular RNA source. The choice of (tissue) source and controls will modify the biases flowing into the results of the screen. Invariably, validation experiments will be indicated to distinguish microarray-derived candidates that are strong modifiers of the disease process and to overcome the limitations of each RNA source.

Several approaches can be taken to validate and to prioritize candidate modifiers once a shortlist has been identified. Among the most important are gene knockout and knock-in strategies in cells and model organisms, because these can replicate more closely the actions of potential modifiers and identify phenotypic changes and mechanisms. For a high-throughput genetic validation of microarray candidates, simple model organisms such as yeast, flies, and worms are most frequently used.

An elegant application of this strategy resulted in the discovery of a new modifier candidate for multiple sclerosis (MS). Microarray analysis of MS lesions yielded new modifiers of MS that were validated in autoimmune encephalomyelitis (Chabas et al., 2001). In a landmark study, Lawrence Steinman's group at Stanford defined microarray-derived modifiers of human MS. By combining expression analysis and high-throughput sequencing of expressed sequence tags in a rat model of MS and human MS plaque tissue, they found an increase in osteopontin mRNA abundance in both human and rat tissues. The biological role of osteopontin in the progression of MS was then further validated in knockout mice: osteopontin-deficient mice were resistant to the progressive MS subtype and had significantly more remissions compared to wild-type mice. Using microarrays as a screening tool, osteopontin is now a promising novel drug target for blocking progressive MS in humans.

When using microarrays to discover modifier genes in neurodegenerative diseases, genome-wide mRNA expression profile is determined in postmortem brain tissue from patients. The investigator applies a series of noise filters and significance statistics to identify candidate modifier genes that are differentially expressed in patient tissue out of the tens of thousands of genes interrogated by human genome arrays.

Neurodegenerative processes are highly selective for specific neuronal populations and brain regions and are often associated with characteristic histological lesions. Each neurodegenerative disease preferentially affects distinct neuronal populations and distinct brain regions and is associated with hallmark histopathological lesions. This vulnerable neuronal population is often distributed in distinct brain regions. For example, in Parkinson's disease (PD) dopaminergic neurons localized to the substantia nigra pars compacta are predominantly affected, while dopaminergic cells in other brain regions are less vulnerable. Regional and cellular profiling techniques have been developed that are tailored to investigate the selective regional and cellular vulnerability of neurodegenerative diseases.

Expression analysis of vulnerable brain regions (regional profiling), vulnerable neuronal or glial populations (cellular profiling), or characteristic histological lesions such as MS plaques (Chabas et al., 2001) (lesion profiling) has lead to intriguing results reflecting the strengths and weaknesses of each approach. Nonspecific gene expression changes related to neuronal loss or reactive glial proliferation must be considered in the interpretation of gene expression in affected brain regions have used disease controls with dopaminergic cell loss such as progressive supranuclear paralysis to control cell loss not specific to PD pathogenesis. Alternatively, expression changes of neuronal markers such as neurofilaments or of neuronal specific subpopulations such as tyrosine hydroxylase and other dopamine biosynthesis enzymes, and glial markers such as glial fibrillary acidic protein, may be used to estimate the range of gene expression changes accounted for by unspecific cell loss and gliosis alone. Validation of regional expression changes in vulnerable neuronal populations by double-labeling immunohistochemistry or double-labeling in situ hybridization can address this concern. Analysis of gene expression in patients 'at risk' or at presymptomatic disease stages could reduce some of these biases but tissue availability and diagnostic uncertainty limit this approach.

Laser-capture microdissection (LCM) of vulnerable neuronal populations allows direct sampling of the neuronal population of interest under the microscope (Bahn et al., 2001; Wittliff and Erlander, 2002; Kamme et al., 2003). LCM controls for some biases associated with regional profiling such as reactive gliosis or nonspecific neuron loss. Distinct considerations guide the interpretation of LCM expression profiles. During interpretation of results, one must take into account whether gene expression changes observed are specific to the disease in question or whether they may be generally found in dying neurons irrespective of the specific disease process. Comparison with cellular profiles in disease controls could help to estimate this bias. In addition, a selection bias might be introduced by LCM; cellular profiling might select for neurons less affected in the disease process. This is particularly a concern if advanced disease stages are profiled. For example, in PD, an estimated 70% of nigral neurons have died prior to the onset of clinical symptoms (Fearnley and Lees, 1991). Dopaminergic neurons that survive the disease process and thus are found in postmortem tissue might reflect a particularly resistant subpopulation rather than reflecting the transcription profile of vulnerable dopaminergic cells. The cellular gene expression profile thus might identify transcripts of genes conferring enhanced resistance within the vulnerable cell population.

A novel approach to avoid some of these limitations has made use of altered gene expression in peripheral tissues of patients with neurodegenerative diseases. In this paradigm, neurodegenerative diseases are approached as a systemic disease with systemic changes in the expression of disease-modifying and susceptibility genes that act in a combinatorial fashion with localizing factors unique to vulnerable neuronal populations and lead to selective neurodegeneration. Biochemical and transcriptional alterations in peripheral tissues such as platelets (Di Luca et al., 2000), lymphocytes (Ibarreta et al., 1998; Caronti et al., 1999), fibroblasts (Citron et al., 1994) and muscle of neurodegenerative patients have been extensively documented in Alzheimer's disease (AD), PD, and other neurodegenerative diseases. Indeed, most genes implicated in familial AD (Di Luca et al., 2000; Citron et al., 1994; Li et al., 1999; Schlossmacher et al., 1992) and familial PD (Shin et al., 2000; Sunada et al., 1998) are ubiquitously expressed.

To gain insight into the molecular basis of these alterations, the inventors screened differential gene expression in lymphoblasts of controls and two independent groups of AD patients using cDNA microarrays. This genomic screen identified six differentially expressed genes. One of the six genes (LR11) is a novel neuronal ApoE receptor and thus an excellent candidate modifier. Subsequent validation experiments in the brain indicated that LR11 was enriched in vulnerable cortical and hippocampal pyramidal neurons in human control brains, and that it was concentrated in neuronal endosomal-lysosomal compartments. In striking contrast to normal tissue, LR11 was diminished in AD brains with dramatic reductions in surviving neurons. In cultured cells, LR11 overexpression markedly reduced extracellular AP levels, providing a mechanistic link between LR11 and Aβ clearance. Thus, changes in LR11 expression in AD lymphoblasts and brain, and its effects on extracellular Aβ, suggested an important role for this apoE receptor in AD pathogenesis.

Toxic and genetic animal models of neurodegenerative diseases faithfully replicate key features of human neurodegenerative diseases. Microarray analysis of tissue from animal models, which is generally more available than human tissue samples, allows for dissection of the molecular machinery involved in progressive neurodegeneration. In extension of the 'static' gene expression snapshot detectable in human postmortem tissue representative of the disease endpoint, transgenic animal models allow for detection of the 'dynamic' range of gene expression changes during the disease progression, at any selected timepoints when the animals are sacrificed. This approach is particularly valuable in the analysis of chronic progressive neurodegenerative diseases. Pathology may begin several years prior to the onset of clinical symptoms and progresses from early disease stages associated with low morbidity and good response to medications to clinically debilitating end stages associated with the depletion of select neuronal populations. Specimens from animal models can capture these changes over the entire course of a disease, in statistically meaningful numbers.

For example, in PD, tremor and bradykinesia develop only after an estimated 70% of vulnerable dopaminergic neurons in the substantia nigra have already died during the presymptomatic stage, spanning a period of years (Feamley and Lees, 1991). It is a fundamental goal for the neurologist to develop medications that stop or slow disease progression at presymptomatic or early disease stages. Modeling changes in presymptomatic or early symptomatic stages is especially crucial for understanding molecular pathogenesis and, perhaps even more importantly, for identifying therapeutic targets that might help to slow the disease process before it reaches the threshold for clinical symptoms.

In one model of PD, *Drosophila* expressing human α-synuclein (αS) carrying the disease-linked A30P mutation in a panneural pattern faithfully replicate age-dependent onset and chronic progression of human PD. Transgenic αS *Drosophila* develop adult-onset, progressive degeneration of dopaminergic cells, with widespread Lewy body inclusions and impaired locomotor function as monitored by progressive loss of climbing ability (Feany and Bender, 2000). Loss of dopaminergic neurons and inclusion formation are first detected at 10 days of age, while at day 1 post-eclosion, the A30P-αS *Drosophila* are still histologically and behaviorally normal.

To identify gene expression changes at presymptomatic, early and advanced disease stages, the inventors hybridized RNA extracted from fly heads to high-density oligonucleotide arrays spotted with probes representing the entire *Drosophila* genome. In presymptomatic §S transgenics, microarray analysis was more sensitive than conventional neuropathological techniques in elucidating disease-associated changes (Scherzer et al., 2003). It was interesting that despite a 'normal' phenotype at this stage, in the one-day-old αS transgenics, transcription of thirty six genes was significantly and reproducibly dysregulated. These abnormalities presage neuronal loss, Lewy body-like inclusion formation, and locomotor impairment at later stages. The inventors found that the αS signature genes are dysregulated independent of disease stage in both presymptomatic and symptomatic animals (FIGS. 1A-F). This suggests that parts of the molecular machinery dysregulated during symptomatic disease stages is already altered in presymptomatic transgenics prior to the onset of neurodegeneration (FIGS. 1A-F). Temporal profiling of progressive gene expression changes in neurodegenerative disease models provides unbiased starting points for defining disease mechanisms and for identifying potential targets for neuroprotective drugs at preclinical stages.

The present invention also has broader implications than neurologic diseases. Thus, one may use differentially expressed RNA of any gene in blood to a) identify susceptibility genes and age-at-onset genes for any disease; and b) to identify therapeutic targets. Specific applications of this technology are described in greater detail, below.

I. Neurodegenerative Diseases

Neurodegenerative Diseases (NDs) include a wide variety of debilitating afflictions of the central and peripheral nervous systems. Most, however, affect the CNS. Such diseases include Alzheimer's Disease, Pick's Disease, senile dementia, Parkinson's Disease, multiple sclerosis, multiple system atrophy, dementia with Lewy bodies, Huntingon's Disease, Progressive Supranuclear Palsy, Creutzfeldt-Jakob Disease and amyotrophic lateral sclerosis.

1. Parkinson's Disease

Parkinson's Disease (PD) is one of a group of conditions classified as movement disorders. It is both chronic and progressive. Parkinson's disease occurs when cells of the substantia nigra begin to malfunction and eventually die. This results in the loss of production of production, a chemical messenger that transports signals to the parts of the brain that control movement initiation and coordination. The primary symptoms are tremors, rigidity or stiffness of the limbs and trunk, bradykinesia or slowness of movement, and postural instability or impaired balance and coordination. Secondary symptoms included speech changes, loss of facial expression, difficulty swallowing, drooling, pain, dementia or confusion, sleep disturbances, depression, fear or anxiety, memory difficulties, urinary problems, fatigue and aching, and loss of energy. However, symptoms vary, and the disease progression may be rapid or not.

Upwards of one million Americans suffer from PD. While approximately 15% of Parkinson's patients are diagnosed before the age of 40, incidence increases with age. The cause is unknown, and although there is presently no cure, there are many treatment options such as medication and surgery to manage the symptoms. The degree of success of each treatment varies among individuals, as does the length of time the treatment option remains effective.

Levodopa is a dopamine precursor, which was considered a breakthrough in the treatment of PD. Unfortunately, patients experienced debilitating side effects, including severe nausea and vomiting, and with increased dosing and prolonged use, patients experienced other side effects including dyskinesias. Sinemet (Levodopa+Carbidopa) represented a significant improvement in that the addition of carbidopa prevents levodopa from being metabolized in the gut, liver and other tissues, allowing more of it to get to the brain. Thus, a smaller dose of levodopa is needed, and the severe nausea and vomiting was greatly reduced.

Stalevo (carbidopa+levodopa+entacapone) is combination tablet for patients who experience signs and symptoms of end-of-dose "wearing-off." The tablet combines carbidopa/levodopa with entacapone. While carbidopa reduces the side effects of levodopa, entacapone extends the time levodopa is active in the brain (up to 10 percent longer).

Symmetrel (amantadine hydrochloride) activates both the release of dopamine from storage sites, and possibly blocks the re-uptake of dopamine into nerve terminals. It also has a glutamate receptor blocking activity. Its dopaminergic actions result in its usefulness in reducing dyskinesia induced by levodopa and is thus called an indirect-acting dopamine agonist, and is widely used as an early monotherapy, and with the more powerful Sinemet added when needed.

Anticholinergics (trihexyphenidyl, benztropine mesylate, procyclidine, etc.) do not act directly on the dopaminergic system. Instead they act to decrease the activity of another neurotransmitter, acetylcholine. There is a complex interaction between levels of acetylcholine in the brain and levels of dopamine. Many clinicians find that if an agonist or levodopa does not relieve tremor, then the addition of an anticholinergic drug is often effective. Adverse effects include blurred vision, dry mouth and urinary retention. These drugs may be contraindicated in older patients since they can cause confusion and hallucination.

Other drugs include Selegiline or deprenyl (Eldepryl), which have has been shown to delay the need for Sinemet when prescribed in the earliest stage of PD. Dopamine agonists are drugs that activate dopamine receptors directly, and can be taken alone or in combination with Sinemet. Such agonists include bromocriptine (Parlodel), pergolide (Permax), pramipexole (Mirapex) and ropinirole (Requip). COMT inhibitors such as tolcapone (Tasmar) and entacapone (Comtan) prolong the duration of symptom relief by blocking the action of an enzyme which breaks down levodopa.

Surgery is an option for some patients after medications are no longer satisfactory. A patient should discuss surgery thoroughly with his or her neurologist before making any decision. Two older lesioning procedures are pallidotomy and thalamotomy. Pallidotomy can alleviate rigidity and bradykinesia symptoms, and thalamotomy helps to control tremors. Doctors rarely perform either procedure because both permanently destroy parts of the brain and have serious side effects. The damage could make it impossible to perform surgeries that may become available in the future, such as brain tissue transplants.

Deep brain stimulation (DBS) is safer and more effective, has replaced these methods. It is a preferred surgical option because it has the same, if not better results than pallidotomy and thalamotomy. DBS also leaves open the possibility of other therapies, should they become available in the future. As with any surgical procedure, there are risks and side effects. The main benefit of DBS surgery is to reduce motor fluctuations, i.e., the ups and downs caused by a decreasing effectiveness of Sinemet. The electrode is usually placed on one side of the brain. The DBS electrode implanted in the left side of the brain will control the symptoms on the right side of the body and vice versa. In some cases, patients will need to have stimulators on both sides of the brain.

2. Alzheimer's Disease

Dementia is a brain disorder that seriously affects a person's ability to carry out daily activities. Alzheimer's disease (AD) is the most common form of dementia among older people. Scientists believe that up to 4 million Americans suffer from AD. The disease usually begins after age 60, and risk goes up with age. While younger people also may get AD, it is much less common. About 3 percent of men and women ages 65 to 74 have AD, and nearly half of those age 85 and older may have the disease. While the subject of intensive research, the precise causes of AD are still unknown, and there is no cure.

AD attacks parts of the brain that control thought, memory, and language. It was named after Dr. Alois Alzheimer, a German doctor. In 1906, Dr. Alzheimer noticed changes in the brain tissue of a woman who had died of an unusual mental illness. He found abnormal clumps (now called amyloid plaques) and tangled bundles of fibers (now called neurofibrillary tangles). Today, these plaques and tangles in the brain are considered hallmarks of AD.

Scientists also have found other brain changes in people with AD. There is a loss of nerve cells in areas of the brain that are vital to memory and other mental abilities. There also are lower levels of chemicals in the brain that carry complex messages back and forth between nerve cells. Thus, AD may disrupt normal thinking and memory by inhibiting, both physically and chemically, the transfer of message between nerve cells.

AD is a progressive, neurodegenerative disease characterized by memory loss, language deterioration, impaired visuospatial skills, poor judgment, indifferent attitude, but preserved motor function. AD usually begins after age 65, however, its onset may occur as early as age 40, appearing first as memory decline and, over several years, destroying cognition, personality, and ability to function. Confusion and restlessness may also occur. The type, severity, sequence, and progression of mental changes vary widely. The early symptoms of AD, which include forgetfulness and loss of concentration, can be missed easily because they resemble natural signs of aging. Similar symptoms can also result from fatigue, grief, depression, illness, vision or hearing loss, the use of alcohol or certain medications, or simply the burden of too many details to remember at once.

There is no cure for AD and no way to slow the progression of the disease. For some people in the early or middle stages of the disease, medication such as tacrine may alleviate some cognitive symptoms. Aricept (donepezil) and Exelon (rivastigmine) are reversible acetylcholinesterase inhibitors that are indicated for the treatment of mild to moderate dementia of the Alzheimer's type. Also, some medications may help control behavioral symptoms such as sleeplessness, agitation, wandering, anxiety, and depression. These treatments are aimed at making the patient more comfortable.

AD is a progressive disease. The course of the disease varies from person to person. Some people have the disease only for the last 5 years of life, while others may have it for as many as 20 years. The most common cause of death in AD patients is infection.

The molecular aspect of AD is complicated and not yet fully defined. As stated above, AD is characterized by the formation of amyloid plaques and neurofibrillary tangles in the brain, particularly in the hippocampus which is the center for memory processing. Several molecules contribute to these structures: amyloid β protein (Aβ), presenilin (PS), cholesterol, apolipoprotein E (ApoE), and Tau protein. Of these, Aβ appears to play the central role.

Aβ contains approximately 40 amino acid residues. The 42 and 43 residue forms are much more toxic than the 40 residue form. A' is generated from an amyloid precursor protein (APP) by sequential proteolysis. One of the enzymes lacks sequence specificity and thus can generate Aβ of varying (39-43) lengths. The toxic forms of Aβ cause abnormal events such as apoptosis, free radical formation, aggregation and inflammation.

Presenilin encodes the protease responsible for cleaving APP into Aβ. There are two forms—PS1 and PS2. Mutations in PSI, causing production of $A\beta_{42}$, are the typical cause of early onset AD.

Cholesterol-reducing agents have been alleged to have AD-preventative capabilities, although no definitive evidence has linked elevated cholesterol to increased risk of AD. However, the discovery that Aβ contains a sphingolipid binding domain lends further credence to this theory.

Similarly, ApoE, which is involved in the redistribution of cholesterol, is now believed to contribute to AD development. Individuals having the ε4 allele, which exhibits the least degree of cholesterol efflux from neurons, are more likely to develop AD.

Tau protein, associated with microtubules in normal brain, forms paired. helical filaments (PHFs) in AD-affected brains which are the primary constituent of neurofibrillary tangles. Recent evidence suggests that Aβ proteins may cause hyperphosphorylation of Tau proteins, leading to disassociation from microtubules and aggregation into PHFs.

For AD, drugs have been used to limit the progression of the disease and to alleviate or improve certain of the associated symptoms. These drug generally fit into the broad categories of cholinesterase inhibitors, muscarinic agonists, anti-oxidants or anti-inflammatories. Galantamine (Reminyl), tacrine (Cognex), selegiline, physostigmine, revistigmin, donepezil, (Aricept), rivastigmine (Exelon), metrifonate, milameline, xanomeline, saeluzole, acetyl-L-carnitine, idebenone, ENA-713, mermic, quetiapine, neurestrol and neuromidal are just some of the drugs proposed as therapeutic agents for Alzheimer's disease.

3. Progressive Supranuclear Palsy

Progressive supranuclear palsy (PSP) is a rare brain disorder that causes serious and permanent problems with control of gait and balance. The most obvious sign of the disease is an inability to aim the eyes properly, which occurs because of lesions in the area of the brain that coordinates eye movements. Some patients describe this effect as a blurring. PSP patients often show alterations of mood and behavior, including depression and apathy as well as progressive mild dementia.

The pattern of symptoms can be quite different from person to person. The symptoms of PSP are caused by a gradual deterioration of brain cells in a few tiny but important places at the base of the brain, in the region called the brainstem. PSP is often misdiagnosed because some of its symptoms are very much like those of Parkinson's disease, Alzheimer's disease, and more rare neurodegenerative disorders, such as Creutzfeldt-Jakob disease. The key to establishing the diagnosis of PSP is the identification of early gait instability and difficulty moving the eyes, the hallmark of the disease, as well as ruling out other similar disorders, some of which are treatable. Although PSP gets progressively worse, PSP itself is not fatal.

There is currently no effective treatment for PSP, although in some patients, the slowness, stiffness, and balance problems may respond to anti-Parkinsonian agents such as levodopa, or levodopa combined with anticholinergic agents, but the effect is usually temporary. The speech, vision, and swallowing difficulties usually do not respond to any drug treatment. Another group of drugs that has been of some modest success in PSP are antidepressant medications. The most commonly used of these drugs are Prozac, Elavil, and Tofranil. The anti-PSP benefit of these drugs seems not to be related to their ability to relieve depression.

Non-drug treatment for PSP can take many forms. Patients frequently use weighted walking aids because of their tendency to fall backward. Bifocals or special glasses called prisms are sometimes prescribed for PSP patients to remedy the difficulty of looking down. Formal physical therapy is of no proven benefit in PSP, but certain exercises can be done to keep the joints limber. A surgical procedure, a gastrostomy, may be necessary when there are swallowing disturbances. This surgery involves the placement of a tube through the skin of the abdomen into the stomach (intestine) for feeding purposes.

PSP gets progressively worse but is not itself directly life-threatening. It does, however, predispose patients to serious complications such as pneumonia secondary to difficulty in swallowing (dysphagia). The most common complications are choking and pneumonia, head injury, and fractures caused by falls. The most common cause of death is pneumonia. With good attention to medical and nutritional needs, however, most PSP patients live well into their 70's and beyond.

4. Multiple System Atrophy

Multiple system atrophy (MSA) is a neurodegenerative disease marked by a combination of symptoms affecting movement, blood pressure, and other body functions; hence the label "multiple system" atrophy. Symptoms of MSA vary in distribution, onset and severity from person to person. Because of this, three different diseases were initially described to encompass this range of symptoms: Shy-Drager syndrome, striatonigral degeneration, and olivopontocerebellar atrophy. In Shy-Drager syndrome, the most prominent symptoms are those involving the autonomic system, the body system that regulates blood pressure, urinary function, and other functions not involving conscious control. Striatonigral degeneration causes parkinsonian symptoms such as slowed movements and rigidity, while olivopontocerebellar atrophy principally affects balance, coordination, and speech. These diseases are now considered forms of MSA.

MSA can cause a wide range of symptoms, including stiffness or rigidity, freezing or slowed movements, postural instability, loss of balance, incoordination, orthostatic hypotension, dizziness, lightheadedness, fainting, blurred vision, male impotence, urinary difficulties, constipation, speech and swallowing difficulties. MSA progresses over the course of several years to cause more widespread and severe symptoms, such as mild loss of cognitive abilities, with impairments in attention and speed of thinking.

A number of drugs can be used to treat the various symptoms of MSA, although they become less effective as the disease progresses. Levodopa and dopamine agonists, used to treat Parkinson's disease, are sometimes effective for slowness and rigidity. Orthostatic hypotension can be improved with fludrocortisone, midodrine, or other drugs that raise blood pressure. Male impotence may be treated with penile implants or drugs. Incontinence may be treated with medications or catheterization.

II. Diagnostic/Prognostic Determinations In Neurodegenerative Diseases

The gene lists presented in Tables 1-5 were generated by comparing the gene expression profile of peripheral blood (derived from a comparison of 50 patients afflicted by Parkinson's disease and 50 control subjects.

TABLE 1

Alzheimer's Disease Genes

Input Parameters

Imputation Engine
Data Type
Data in log scale?
Number of Permutations
Blocked Permutation?
RNG Seed
(Delta, Fold Change)
(Upper Cutoff, Lower Cutoff)
Computed Quantities Computed Exchangeability Factor S0
S0 percentile
False Significant Number (Median, 90 percentile)
False Discovery Rate (Median, 90 percentile)
Pi0Hat TABLE 1-continued Alzheimer's Disease Genes 123 Positive Significant Genes

| Row | Affymetrix probe set | Gene ID | Fold Change | q-value (%) | Accession # | Gene symbol |
|---|---|---|---|---|---|---|
| | 208729_x_at | major histocompatibility complex, class I, B | 1.26462 | 4.124513619 | D83043.1 | HLA-B |
| | 202258_s_at | hypothetical protein from BCRA2 region | 1.43615 | 4.124513619 | U50532.1 | CG005 |
| | 217819_at | HSPC041 protein | 1.24574 | 4.124513619 | NM_016099.1 | LOC51125 |
| | 201071_x_at | splicing factor 3b, subunit 1, 155 kDa | 1.22692 | 4.124513619 | NM_012433.1 | SF3B1 |
| | 208944_at | transforming growth factor, beta receptor II (70/80 kDa) | 1.21041 | 4.124513619 | D50683.1 | TGFBR2 |
| | 200899_s_at | meningioma expressed antigen 5 (hyaluronidase) | 1.19093 | 4.124513619 | NM_012215.1 | MGEA5 |
| | 208720_s_at | RNA-binding region (RNP1, RRM) containing 2 | 1.22868 | 4.124513619 | AI890947 | RNPC2 |
| | 200847_s_at | hypothetical protein MGC8721 | 1.21446 | 4.124513619 | NM_016127.1 | MGC8721 |
| | 217436_x_at | — | 1.21876 | 4.124513619 | M80469 | — |
| | 204122_at | TYRO protein tyrosine kinase binding protein | 1.27206 | 4.124513619 | NM_003332.1 | TYROBP |
| | 213017_at | abhydrolase domain containing 3 | 1.59338 | 4.124513619 | AL534702 | ABHD3 |
| | 201362_at | NS1-binding protein | 1.30117 | 4.124513619 | AF205218.1 | NS1-BP |
| | 212177_at | ESTs, Moderately similar to SR rich protein [*Homo sapiens*] [*H. sapiens*] | 1.33571 | 4.124513619 | AL080186.1 | — |
| | 221619_s_at | mitochondrial carrier homolog 1 | 1.18682 | 4.124513619 | AF189289.1 | MTCH1 |
| | 212176_at | SR rich protein | 1.33056 | 4.124513619 | AL080186.1 | DKFZp564B0769 |
| | 202157_s_at | CUG triplet repeat, RNA binding protein 2 | 1.1469 | 4.124513619 | U69546.1 | CUGBP2 |
| | 208893_s_at | dual specificity phosphatase 6 | 1.6957 | 4.124513619 | BC005047.1 | DUSP6 |
| | 209140_x_at | major histocompatibility complex, class I, B | 1.15098 | 4.124513619 | L42024.1 | HLA-B |
| | AFFX-HSAC07/X00351_M_at | actin, beta | 1.2034 | 4.124513619 | X00351 | ACTB |
| | 201371_s_at | cullin 3 | 1.22204 | 5.155642023 | AF062537.1 | CUL3 |
| | 209933_s_at | leukocyte membrane antigen | 1.19121 | 5.155642023 | AF020314.1 | CMRF-35H |
| | 200033_at | DEAD/H (Asp-Glu-Ala-Asp/His) box polypeptide 5 (RNA helicase, 68 kDa) | 1.15575 | 5.155642023 | NM_004396.2 | DDX5 |
| | 203518_at | Chediak-Higashi syndrome 1 | 1.31909 | 5.155642023 | NM_000081.1 | CHS1 |
| | 204072_s_at | hypothetical protein CG003 | 1.33971 | 5.379800372 | NM_023037.1 | 13CDNA73 |
| | 209238_at | syntaxin 3A | 1.28013 | 5.379800372 | BE966922 | STX3A |
| | 200677_at | pituitary tumor-transforming 1 interacting protein | 1.17831 | 5.379800372 | NM_004339.2 | PTTG1IP |
| | 200797_s_at | myeloid cell leukemia sequence 1 (BCL2-related) | 1.18335 | 5.379800372 | NM_021960.1 | MCL1 |
| | 38149_at | KIAA0053 gene product | 1.22759 | 5.379800372 | D29642 | KIAA0053 |
| | 209007_s_at | hypothetical protein dJ465N24.2.1 | 1.4336 | 5.379800372 | AF267856.1 | DJ465N24.2.1 |
| | 201009_s_at | thioredoxin interacting protein | 1.20659 | 5.379800372 | NM_006472.1 | TXNIP |
| | 201944_at | hexosaminidase B (beta polypeptide) | 1.19953 | 5.379800372 | NM_000521.2 | HEXB |
| | 204806_x_at | major histocompatibility complex, class I, F | 1.20788 | 5.379800372 | NM_018950.1 | HLA-F |
| | 208718_at | *Homo sapiens*, clone IMAGE: 5264473, mRNA | 1.10703 | 5.379800372 | Z97056 | — |
| | 211529_x_at | HLA-G histocompatibility antigen, class I, G | 1.22016 | 5.379800372 | M90684.1 | HLA-G |
| | 217982_s_at | mortality factor 4 like 1 | 1.17772 | 5.379800372 | NM_006791.1 | MORF4L1 |
| | 202181_at | KIAA0247 gene product | 1.25039 | 5.379800372 | NM_014734.1 | KIAA0247 |
| | 203973_s_at | CCAAT/enhancer binding protein (C/EBP), delta | 1.36909 | 5.379800372 | NM_005195.1 | CEBPD |
| | 218067_s_at | hypothetical protein FLJ10154 | 1.43167 | 5.379800372 | NM_018011.1 | FLJ10154 |
| | 211799_x_at | major histocompatibility complex, class I, C | 1.29344 | 5.379800372 | U62824.1 | HLA-C |
| | 213418_at | heat shock 70 kDa protein 6 (HSP70B') | 1.24909 | 5.379800372 | NM_002155.1 | HSPA6 |
| | 202878_s_at | complement component 1, q subcomponent, receptor 1 | 1.24643 | 5.379800372 | NM_012072.2 | C1QR1 |
| | 202727_s_at | interferon gamma receptor 1 | 1.26247 | 5.379800372 | NM_000416.1 | IFNGR1 |
| | 203063_at | protein phosphatase 1F (PP2C domain containing) | 1.33503 | 5.379800372 | NM_014634.1 | PPM1F |
| | 203879_at | phosphoinositide-3-kinase, catalytic, delta polypeptide | 1.1983 | 5.379800372 | U86453.1 | PIK3CD |
| | 201041_s_at | dual specificity phosphatase 1 | 1.28146 | 5.379800372 | NM_004417.2 | DUSP1 |
| | 217739_s_at | pre-B-cell colony-enhancing factor | 1.3185 | 5.999292536 | NM_005746.1 | PBEF |
| | 208374_s_at | capping protein (actin filament) muscle Z-line, alpha 1 | 1.23647 | 5.999292536 | NM_006135.1 | CAPZA1 |
| | 202228_s_at | stromal cell derived factor receptor 1 | 1.2847 | 5.999292536 | NM_017455.1 | SDFR1 |
| | 218865_at | hypothetical protein FLJ22390 | 1.87627 | 5.999292536 | NM_022746.1 | FLJ22390 |
| | 211911_x_at | major histocompatibility complex, class I, B | 1.18099 | 5.999292536 | L07950.1 | HLA-B |
| | 200667_at | ubiquitin-conjugating enzyme E2D 3 (UBC4/5 homolog, yeast) | 1.38233 | 5.999292536 | BF448062 | UBE2D3 |
| | 204076_at | lysosomal apyrase-like 1 | 1.31159 | 5.999292536 | AB002390.1 | LYSAL1 |
| | 45687_at | hypothetical protein MGC3121 | 1.27278 | 5.999292536 | AA161130 | MGC3121 |
| | 200728_at | *Homo sapiens* mRNA; cDNA DKFZp566E233 (from clone DKFZp566E233) | 1.20826 | 5.999292536 | AA699583 | — |
| | 211509_s_at | reticulon 4 | 1.16322 | 6.874189364 | AB015639.1 | RTN4 |
| | 201651_s_at | protein kinase C and casein kinase substrate in neurons 2 | 1.24334 | 6.874189364 | NM_007229.1 | PACSIN2 |
| | 218191_s_at | hypothetical protein FLJ11240 | 1.19397 | 6.874189364 | NM_018368.1 | FLJ11240 |
| | 209240_at | O-linked N-acetylglucosamine (GlcNAc) transferase (UDP-N-acetylglucosamine:polypeptide-N-acetylglucosaminyl transferase) | 1.24468 | 6.874189364 | AF070560.1 | OGT |
| | 213737_x_at | *Homo sapiens*, clone IMAGE: 4133122, mRNA | 1.41322 | 6.874189364 | AI620911 | — |
| | 201369_s_at | zinc finger protein 36, C3H type-like 2 | 1.40662 | 10.5899674 | NM_006887.1 | ZFP36L2 |
| | 212934_at | hypothetical protein LOC137886 | 1.40951 | 10.5899674 | AI245523 | LOC137886 |
| | 201594_s_at | protein phosphatase 4, regulatory subunit 1 | 1.24052 | 10.5899674 | NM_005134.1 | PPP4R1 |
| | 201795_at | lamin B receptor | 1.2988 | 10.5899674 | NM_002296.1 | LBR |

TABLE 1-continued

Alzheimer's Disease Genes

| | | | | | |
|---|---|---|---|---|---|
| 211676_s_at | interferon gamma receptor 1 | 1.26167 | 10.5899674 | AF056979.1 | IFNGR1 |
| 211075_s_at | CD47 antigen (Rh-related antigen, integrin-associated signal transducer) | 1.22213 | 10.5899674 | Z25521.1 | CD47 |
| 220066_at | caspase recruitment domain family, member 15 | 1.42721 | 10.5899674 | NM_022162.1 | CARD15 |
| 208783_s_at | membrane cofactor protein (CD46, trophoblast-lymphocyte cross-reactive antigen) | 1.34358 | 10.5899674 | AL570661 | MCP |
| 201363_s_at | NS1-binding protein | 1.34679 | 10.5899674 | AB020657.1 | NS1-BP |
| 212033_at | S164 protein | 1.30705 | 10.5899674 | BE466128 | S164 |
| 217865_at | goliath protein | 1.17647 | 10.5899674 | NM_018434.1 | GP |
| 201987_at | Homo sapiens cDNA FLJ30332 fis, clone BRACE2007254. | 1.33791 | 10.5899674 | NM_005121.1 | — |
| 208901_s_at | topoisomerase (DNA) I | 1.20747 | 10.5899674 | J03250.1 | TOP1 |
| 211997_x_at | H3 histone, family 3B (H3.3B) | 1.16324 | 10.5899674 | NM_005324.1 | H3F3B |
| 211185_s_at | hypothetical protein FLJ14753 | 1.17687 | 13.24385107 | AF130099.1 | FLJ14753 |
| 209201_x_at | chemokine (C—X—C motif) receptor 4 | 1.17969 | 13.24385107 | L01639.1 | CXCR4 |
| 204949_at | intercellular adhesion molecule 3 | 1.21969 | 13.24385107 | NM_002162.2 | ICAM3 |
| 208891_at | dual specificity phosphatase 6 | 1.46404 | 13.24385107 | BC003143.1 | DUSP6 |
| 203041_s_at | lysosomal-associated membrane protein 2 | 1.21644 | 13.24385107 | J04183.1 | LAMP2 |
| 210225_x_at | leukocyte immunoglobulin-like receptor, subfamily B (with TM and ITIM domains), member 3 | 1.3547 | 13.24385107 | AF009635.1 | LILRB3 |
| 217989_at | retinal short-chain dehydrogenase/reductase 2 | 1.16327 | 13.24385107 | NM_016245.1 | RetSDR2 |
| 206342_x_at | iduronate 2-sulfatase (Hunter syndrome) | 1.32878 | 13.24385107 | NM_006123.1 | IDS |
| 213612_x_at | hypothetical protein DJ328E19.C1.1 | 1.14312 | 13.24385107 | AI800419 | DJ328E19.C1.1 |
| 201152_s_at | muscleblind-like (Drosophila) | 1.25269 | 13.24385107 | NM_021038.1 | MBNL1 |
| 212820_at | rabconnectin-3 | 1.27196 | 13.24385107 | AB020663.1 | RC3 |
| 201978_s_at | KIAA0141 gene product | 1.23359 | 13.24385107 | NM_014773.1 | KIAA0141 |
| 203415_at | programmed cell death 6 | 1.23959 | 13.24385107 | NM_013232.1 | PDCD6 |
| 221840_at | protein tyrosine phosphatase, receptor type, E | 1.16613 | 13.24385107 | AA775177 | PTPRE |
| 202510_s_at | tumor necrosis factor, alpha-induced protein 2 | 1.19158 | 13.24385107 | NM_006291.1 | TNFAIP2 |
| 205788_s_at | KIAA0663 gene product | 1.14103 | 13.24385107 | NM_014827.1 | KIAA0663 |
| 200909_s_at | ribosomal protein, large P2 | 1.16941 | 13.24385107 | NM_001004.1 | RPLP2 |
| 212515_s_at | DEAD/H (Asp-Glu-Ala-Asp/His) box polypeptide 3 | 1.32246 | 13.24385107 | R60068 | DDX3 |
| 213359_at | Homo sapiens mRNA; cDNA DKFZp313H039 (from clone DKFZp313H039) | 1.27725 | 13.24385107 | W74620 | — |
| 218319_at | pellino homolog 1 (Drosophila) | 1.32469 | 13.24385107 | NM_020651.2 | PELI1 |
| 208865_at | casein kinase 1, alpha 1 | 1.1455 | 13.24385107 | BG534245 | CSNK1A1 |
| 200709_at | FK506 binding protein 1A, 12 kDa | 1.15014 | 13.24385107 | NM_000801.1 | FKBP1A |
| 202429_s_at | protein phosphatase 3 (formerly 2B), catalytic subunit, alpha isoform (calcineurin A alpha) | 1.20672 | 13.24385107 | AL353950.1 | PPP3CA |
| 205495_s_at | granulysin | 1.52956 | 13.24385107 | NM_006433.1 | GNLY |
| 203420_at | family with sequence similarity 8, member A1 | 1.30098 | 13.24385107 | NM_016255.1 | FAM8A1 |
| 221698_s_at | C-type (calcium dependent, carbohydrate-recognition domain) lectin, superfamily member 12 | 1.33696 | 13.24385107 | AF313468.1 | CLECSF12 |
| 200921_s_at | B-cell translocation gene 1, anti-proliferative | 1.18383 | 13.24385107 | NM_001731.1 | BTG1 |
| 220720_x_at | hypothetical protein FLJ14346 | 1.43949 | 13.24385107 | NM_025029.1 | FLJ14346 |
| 219452_at | putative dipeptidase | 1.23357 | 13.24385107 | NM_022355.1 | LOC64174 |
| 201779_s_at | ring finger protein 13 | 1.22765 | 13.24385107 | AF070558.1 | RNF13 |
| 211458_s_at | GABA(A) receptors associated protein like 3 | 1.33045 | 13.24385107 | AF180519.1 | GABARAPL3 |
| 208763_s_at | delta sleep inducing peptide, immunoreactor | 1.23613 | 13.24385107 | AL110191.1 | DSIPI |
| 203140_at | B-cell CLL/lymphoma 6 (zinc finger protein 51) | 1.25778 | 13.24385107 | NM_001706.1 | BCL6 |
| 204897_at | prostaglandin E receptor 4 (subtype EP4) | 1.35521 | 13.24385107 | NM_000958.1 | PTGER4 |
| 37145_at | granulysin | 1.42708 | 13.24385107 | M85879 | GNLY |
| 208724_s_at | RAB1A, member RAS oncogene family | 1.20931 | 13.63750471 | BC000905.1 | RAB1A |
| 201857_at | zinc finger RNA binding protein | 1.24551 | 13.63750471 | NM_016107.1 | ZFR |
| 203760_s_at | Src-like-adaptor | 1.32376 | 13.63750471 | U44403.1 | SLA |
| 204194_at | BTB and CNC homology 1, basic leucine zipper transcription factor 1 | 1.36544 | 13.63750471 | NM_001186.1 | BACH1 |
| 212867_at | nuclear receptor coactivator 2 | 1.25228 | 13.63750471 | AI040324 | NCOA2 |
| 200754_x_at | splicing factor, arginine/serine-rich 2 | 1.16968 | 13.63750471 | NM_003016.1 | SFRS2 |
| 221728_x_at | Homo sapiens cDNA FLJ30298 fis, clone BRACE2003172. | 1.90901 | 13.63750471 | AK025198.1 | — |
| 220044_x_at | cisplatin resistance-associated overexpressed protein | 1.3387 | 13.63750471 | NM_016424.1 | LUC7A |
| 208990_s_at | heterogeneous nuclear ribonucleoprotein H3 (2H9) | 1.22049 | 13.63750471 | AF132362.1 | HNRPH3 |
| 209858_x_at | metallo phosphoesterase | 1.23264 | 13.63750471 | BC002877.1 | MPPE1 |
| 212643_at | chromosome 14 open reading frame 32 | 1.17003 | 13.63750471 | AI671747 | C14orf32 |
| 217122_s_at | KIAA0447 gene product | 1.18529 | 13.63750471 | AL031282 | KIAA0447 |
| 204982_at | G protein-coupled receptor kinase-interactor 2 | 1.42893 | 13.63750471 | NM_014776.1 | GIT2 |
| 218614_at | hypothetical protein FLJ10652 | 1.26927 | 13.63750471 | NM_018169.1 | FLJ10652 |
| 211932_at | hypothetical protein LOC220988 | 1.27474 | 13.63750471 | BE867771 | LOC220988 |

1 Negative Significant Genes

| | Gene Name | Gene ID | Fold Change | q-value (%) | | |
|---|---|---|---|---|---|---|
| 204031_s_at | poly(rC) binding protein 2 | | 0.82032 | 4.124513619 | NM_005016.1 | PCBP2 |

TABLE 2

Late Parkinson's Disease Genes

Input Parameters

| | |
|---|---|
| Imputation Engine | 10-Nearest Neighbor Imputer |
| Data Type | Two Class, unpaired data |
| Data in log scale? | FALSE |
| Number of Permutations | 1000 |
| Blocked Permutation? | FALSE |
| RNG Seed | 1234567 |
| (Delta, Fold Change) | (0.25652, 1.25000) |
| (Upper Cutoff, Lower Cutoff) | (2.10933, −2.11361) |

Computed Quantities

| | |
|---|---|
| Computed Exchangeability Factor S0 | 3.457144791 |
| S0 percentile | 0 |
| False Significant Number (Median, 90 percentile) | (31.44334, 84.15717) |
| False Discovery Rate (Median, 90 percentile) | (35.32959, 94.55862) |
| Pi0Hat | 0.9248 |

46 Positive Significant Genes

| Affymetrix Probe Set | Gene ID | Score(d) | Numerator(r) | Denominator(s + s0) | Fold Change | q-value (%) | Accession# | Gene symbol |
|---|---|---|---|---|---|---|---|---|
| 207094_at | interleukin 8 receptor, alpha | 2.823133697 | 196.1675 | 69.48572794 | 1.28542 | 20.5512022 | NM_000634.1 | IL8RA |
| 210784_x_at | leukocyte immunoglobulin-like receptor, subfamily B (with TM and ITIM domains), member 3 | 2.786139032 | 132.3528571 | 47.50403898 | 1.38898 | 20.5512022 | AF009634.1 | LILRB3 |
| 203045_at | ninjurin 1 | 2.748467948 | 112.6996429 | 41.00453234 | 1.38237 | 20.5512022 | NM_004148.1 | NINJ1 |
| 204255_s_at | vitamin D (1,25-dihydroxyvitamin D3) receptor | 2.746281195 | 30.66940476 | 11.1676127 | 1.50246 | 20.5512022 | NM_000376.1 | VDR |
| 211135_x_at | leukocyte immunoglobulin-like receptor, subfamily B (with TM and ITIM domains), member 3 | 2.665378689 | 139.4654762 | 52.32482603 | 1.39789 | 20.5512022 | AF009644.1 | LILRB3 |
| 214992_s_at | deoxyribonuclease II, lysosomal | 2.65367187 | 27.94130952 | 10.52930087 | 1.45157 | 20.5512022 | AD000092 | DNASE2 |
| 220486_x_at | hypothetical protein FLJ22679 | 2.641117803 | 92.1497619 | 34.89043988 | 1.29422 | 20.5512022 | NM_017698.1 | FLJ22679 |
| 211458_s_at | GABA(A) receptors associated protein like 3 | 2.62758422 | 41.45464286 | 15.77671328 | 1.36097 | 20.5512022 | AF180519.1 | GABARAPL3 |
| 209088_s_at | ubinuclein 1 | 2.602898867 | 66.19571429 | 25.43153525 | 1.43261 | 20.5512022 | T70262 | UBN1 |
| 207205_at | carcinoembryonic antigen-related cell adhesion molecule 4 | 2.59143149 | 41.75869048 | 16.11414025 | 1.28078 | 20.5512022 | NM_001817.1 | CEACAM4 |
| 217094_s_at | itchy homolog E3 ubiquitin protein ligase (mouse) | 2.589257944 | 30.10821429 | 11.62812471 | 1.56367 | 20.5512022 | AL109923 | ITCH |
| 211043_s_at | clathrin, light polypeptide (Lcb) | 2.550293171 | 49.18404762 | 19.28564456 | 1.64647 | 20.5512022 | BC006332.1 | CLTB |
| 208262_x_at | Mediterranean fever | 2.545984193 | 38.71190476 | 15.20508449 | 1.30235 | 20.5512022 | NM_000243.1 | MEFV |
| 203749_s_at | retinoic acid receptor, alpha | 2.545377849 | 46.39309524 | 18.22640802 | 1.43414 | 20.5512022 | AI806984 | RARA |
| 210484_s_at | hypothetical protein MGC31957 | 2.493029461 | 40.86095238 | 16.39008003 | 1.35837 | 23.12010247 | BC005043.1 | MGC31957 |
| 221266_s_at | DC-specific transmembrane protein | 2.439504075 | 27.49583333 | 11.27107498 | 1.70562 | 23.12010247 | NM_030788.1 | DCSTAMP |
| 205403_at | interleukin 1 receptor, type II | 2.42360341 | 102.7469048 | 42.39427306 | 1.28625 | 23.12010247 | NM_004633.1 | IL1R2 |
| 206380_s_at | properdin P factor, complement | 2.358966952 | 74.06857143 | 31.39873213 | 1.27723 | 29.78182691 | NM_002621.1 | PFC |
| 211133_x_at | leukocyte immunoglobulin-like receptor, subfamily B (with TM and ITIM domains), member 3 | 2.338601913 | 83.83452381 | 35.84813788 | 1.25996 | 29.78182691 | AF009643.1 | LILRB3 |

TABLE 2-continued

Late Parkinson's Disease Genes

| | | | | | | | | |
|---|---|---|---|---|---|---|---|---|
| 211160_x_at | actinin, alpha 1 | 2.337947131 | 45.28607143 | 19.37001519 | 1.27873 | 29.78182691 | M95178.1 | ACTN1 |
| 202626_s_at | v-yes-1 Yamaguchi sarcoma viral related oncogene homolog | 2.31931877 | 236.2909524 | 101.8794637 | 1.25795 | 30.8268033 | NM_002350.1 | LYN |
| 217497_at | endothelial cell growth factor 1 (platelet-derived) | 2.3167546 | 31.29809524 | 13.50945639 | 1.26805 | 30.8268033 | AW613387 | ECGF1 |
| 204669_s_at | ring finger protein 24 | 2.28871869 | 123.9395238 | 54.15236235 | 1.33671 | 31.74700638 | NM_007219.2 | RNF24 |
| 210225_x_at | leukocyte immunoglobulin-like receptor, subfamily B (with TM and ITIM domains), member 3 | 2.280510364 | 100.0204762 | 43.85881238 | 1.32653 | 31.74700638 | AF009635.1 | LILRB3 |
| 205312_at | spleen focus forming virus (SFFV) proviral integration oncogene spi1 | 2.269137615 | 28.46880952 | 12.54609211 | 1.40281 | 31.74700638 | NM_003120.1 | SPI1 |
| 219457_s_at | Ras and Rab interactor 3 | 2.256762473 | 33.38488095 | 14.79326307 | 1.33269 | 31.74700638 | NM_024832.1 | RIN3 |
| 206177_s_at | arginase, liver | 2.218307517 | 26.95892857 | 12.15292666 | 1.46943 | 35.32959479 | NM_000045.2 | ARG1 |
| 201387_s_at | ubiquitin carboxyl-terminal esterase L1 (ubiquitin thiolesterase) | 2.212881214 | 33.17797619 | 14.99311214 | 1.48358 | 35.32959479 | NM_004181.1 | UCHL1 |
| 200660_at | S100 calcium binding protein A11 (calgizzarin) | 2.210757518 | 270.3917857 | 122.3073012 | 1.26 | 35.32959479 | NM_005620.1 | S100A11 |
| 217715_x_at | ESTs, Weakly similar to hypothetical protein FLJ20294 [Homo sapiens] [H. sapiens] | 2.201055702 | 37.86488095 | 17.20305439 | 1.25873 | 35.32959479 | BE045142 | — |
| 203591_s_at | colony stimulating factor 3 receptor (granulocyte) | 2.197945791 | 122.1710714 | 55.58420592 | 1.26174 | 35.32959479 | NM_000760.1 | CSF3R |
| 209396_s_at | chitinase 3-like 1 (cartilage glycoprotein-39) | 2.19512401 | 130.1642857 | 59.29700788 | 1.43203 | 35.32959479 | M80927.1 | CHI3L1 |
| 211748_x_at | prostaglandin D2 synthase 21 kDa (brain) | 2.193833543 | 59.69166667 | 27.20884037 | 1.43244 | 35.32959479 | BC005939.1 | PTGDS |
| 213921_at | somatostatin | 2.177461799 | 27.58142857 | 12.66677954 | 2.0556 | 35.32959479 | NM_001048.1 | SST |
| 219437_s_at | nasopharyngeal carcinoma susceptibility protein | 2.172586989 | 29.86321429 | 13.7454631 | 1.40131 | 35.32959479 | NM_013275.1 | LZ16 |
| 220001_at | peptidyl arginine deiminase, type IV | 2.161103861 | 54.74678571 | 25.33278789 | 1.27624 | 35.32959479 | NM_012387.1 | PADI4 |
| 216848_at | KIAA1660 protein | 2.154242184 | 30.77785714 | 14.2870924 | 1.5736 | 35.32959479 | AB051447.1 | KIAA1660 |
| 204524_at | 3-phosphoinositide dependent protein kinase-1 | 2.147769764 | 42.33238095 | 19.709925 | 1.25042 | 35.32959479 | NM_002613.1 | PDPK1 |
| 203523_at | lymphocyte-specific protein 1 | 2.144164637 | 93.18785714 | 43.46114824 | 1.27124 | 35.32959479 | NM_002339.1 | LSP1 |
| 220128_s_at | hypothetical protein FLJ13955 | 2.142480782 | 30.30869048 | 14.14654018 | 1.517 | 35.32959479 | NM_024759.1 | FLJ13955 |
| 203273_s_at | lung cancer candidate | 2.138464008 | 25.79345238 | 12.06167243 | 1.2645 | 35.32959479 | NM_007275.1 | FUS1 |
| 209322_s_at | SH2-B homolog | 2.118909707 | 26.84035714 | 12.66706035 | 1.89896 | 35.32959479 | AF227968.1 | SH2B |
| 211372_s_at | interleukin 1 receptor, type II | 2.117049341 | 61.70297619 | 29.14574309 | 1.26768 | 35.32959479 | U64094.1 | IL1R2 |
| 219748_at | hypothetical protein FLJ13693 | 2.112667314 | 33.90797619 | 16.04984181 | 1.42808 | 35.32959479 | NM_024807.1 | FLJ13693 |
| 217552_x_at | complement component (3b/4b) receptor 1, including Knops blood group system | 2.110082394 | 39.48547619 | 18.71276511 | 1.41647 | 35.32959479 | AI432713 | CR1 |
| 206125_s_at | kallikrein 8 (neuropsin/ovasin) | 2.109331047 | 29.58309524 | 14.02487072 | 1.33708 | 35.32959479 | NM_007196.1 | KLK8 |

TABLE 2-continued

Late Parkinson's Disease Genes

43 Negative Significant Genes

| Gene Name | Gene ID | Score(d) | Numerator(r) | Denominator(s + s0) | Fold Change | q-value (%) | #N/A #N/A #N/A | #N/A #N/A #N/A |
|---|---|---|---|---|---|---|---|---|
| 214298_x_at | septin 6 | −3.46408145 | −74.05904762 | 21.37912999 | 0.75616 | 10.2756011 | AL568374 | 36408 |
| 202741_at | protein kinase, cAMP-dependent, catalytic, beta | −3.324890491 | −91.62916667 | 27.55855176 | 0.78729 | 10.2756011 | AA130247 | PRKACB |
| 219528_s_at | B-cell CLL/lymphoma 11B (zinc finger protein) | −3.247871463 | −80.08916667 | 24.65897053 | 0.73738 | 10.2756011 | NM_022898.1 | BCL11B |
| 204274_at | estrogen receptor binding site associated, antigen, 9 | −3.060274531 | −28.95 | 9.459935607 | 0.69169 | 10.2756011 | AA812215 | EBAG9 |
| 216241_s_at | transcription elongation factor A (SII), 1 | −3.000267683 | −94.7075 | 31.56635007 | 0.79331 | 10.2756011 | X57198.1 | TCEA1 |
| 208666_s_at | suppression of tumorigenicity 13 (colon carcinoma) (Hsp70 interacting protein) | −2.954032308 | −27.88297619 | 9.438954378 | 0.73161 | 10.2756011 | U17714.1 | ST13 |
| 211971_s_at | leucine-rich PPR-motif containing | −2.90057545 | −34.33892857 | 11.8386607 | 0.76996 | 10.2756011 | AF052133.1 | LRPPRC |
| 208667_s_at | suppression of tumorigenicity 13 (colon carcinoma) (Hsp70 interacting protein) | −2.880798194 | −45.84738095 | 15.9148187 | 0.78379 | 10.2756011 | U17714.1 | ST13 |
| 208398_s_at | TBP-like 1 | −2.86779345 | −33.59821429 | 11.71570229 | 0.79461 | 10.2756011 | NM_004865.1 | TBPL1 |
| 217140_s_at | — | −2.809037196 | −35.28642857 | 12.56175199 | 0.74406 | 18.49608198 | AJ002428 | — |
| 217736_s_at | heme-regulated initiation factor 2-alpha kinase | −2.721475194 | −185.9922619 | 68.34244248 | 0.77774 | 20.5512022 | NM_014413.2 | HRI |
| 212829_at | Homo sapiens cDNA FLJ13267 fis, clone OVARC1000964. | −2.702548761 | −250.6620238 | 92.75023172 | 0.7832 | 20.5512022 | BE878277 | — |
| 201697_s_at | DNA (cytosine-5-)-methyltransferase 1 | −2.680067339 | −44.5172619 | 16.61050126 | 0.76245 | 20.5512022 | NM_001379.1 | DNMT1 |
| 217466_x_at | — | −2.658590386 | −142.8546429 | 53.7332278 | 0.77269 | 20.5512022 | L48784 | — |
| 201200_at | cellular repressor of E1A-stimulated genes | −2.652875637 | −64.51178571 | 24.31768184 | 0.78519 | 20.5512022 | NM_003851.1 | CREG |
| 208632_at | ring finger protein 10 | −2.636555402 | −162.9575 | 61.80696976 | 0.76556 | 20.5512022 | AL578551 | RNF10 |
| 203685_at | B-cell CLL/lymphoma 2 | −2.60217222 | −41.48440476 | 15.94222106 | 0.79034 | 20.5512022 | NM_000633.1 | BCL2 |
| 212004_at | DKFZP566C0424 protein | −2.59575644 | −46.81428571 | 18.03493001 | 0.72958 | 20.5512022 | AL050028.1 | DKFZP566C0424 |
| 213545_x_at | sorting nexin 3 | −2.568273647 | −123.2303571 | 47.98178624 | 0.79346 | 20.5512022 | BE962615 | SNX3 |
| 204945_at | protein tyrosine phosphatase, receptor type, N | −2.548462138 | −28.46666667 | 11.17013521 | 0.52687 | 20.5512022 | NM_002846.1 | PTPRN |
| 205060_at | poly (ADP-ribose) glycohydrolase | −2.52998379 | −22.44333333 | 8.870939577 | 0.6506 | 20.5512022 | NM_003631.1 | PARG |
| 221478_at | BCL2/adenovirus E1B 19 kDa interacting protein 3-like | −2.528763897 | −146.0079762 | 57.73887249 | 0.70335 | 20.5512022 | AL132665.1 | BNIP3L |
| 209274_s_at | hypothetical protein MGC4276 similar to CG8198 | −2.491679157 | −33.26809524 | 13.35167698 | 0.69264 | 23.12010247 | BC002675.1 | MGC4276 |
| 204798_at | v-myb myeloblastosis viral oncogene homolog (avian) | −2.408142906 | −23.22488095 | 9.64431176 | 0.67722 | 25.57968784 | NM_005375.1 | MYB |
| 221824_s_at | hypothetical protein MGC26766 | −2.40509116 | −171.0021429 | 71.10006711 | 0.76042 | 25.57968784 | AA770170 | MGC26766 |
| 210279_at | G protein-coupled receptor 18 | −2.394545136 | −37.77083333 | 15.77369863 | 0.78725 | 25.57968784 | AF261135.1 | GPR18 |
| 203115_at | ferrochelatase (protoporphyria) | −2.381271363 | −86.62511905 | 36.3776764 | 0.58363 | 25.57968784 | AU152635 | FECH |

TABLE 2-continued

Late Parkinson's Disease Genes

| | | | | | | | | |
|---|---|---|---|---|---|---|---|---|
| 208796_s_at | cyclin G1 | −2.369212609 | −52.68035714 | 22.23538611 | 0.7877 | 25.57968784 | BC000196.1 | CCNG1 |
| 209974_s_at | BUB3 budding uninhibited by benzimidazoles 3 homolog (yeast) | −2.361599339 | −50.49059524 | 21.3798312 | 0.79495 | 25.57968784 | AF047473.1 | BUB3 |
| 212502_at | hypothetical protein FLJ14547 | −2.359643834 | −21.04333333 | 8.918012554 | 0.79068 | 25.57968784 | AV713053 | FLJ14547 |
| 204019_s_at | likely ortholog of mouse Sh3 domain YSC-like 1 | −2.334889534 | −40.47428571 | 17.33456129 | 0.736 | 29.78182691 | NM_015677.1 | SH3YL1 |
| 210260_s_at | TNF-induced protein | −2.322801229 | −67.60869048 | 29.10653293 | 0.78771 | 29.78182691 | BC005352.1 | GG2-1 |
| 208860_s_at | alpha thalassemia/mental retardation syndrome X-linked (RAD54 homolog, *S. cerevisiae*) | −2.31748431 | −56.22511905 | 24.26127279 | 0.75334 | 29.78182691 | U09820.1 | ATRX |
| 215772_x_at | succinate-CoA ligase, GDP-forming, beta subunit | −2.304593093 | −22.7725 | 9.881353923 | 0.7926 | 29.78182691 | AL050226.1 | SUCLG2 |
| 205038_at | zinc finger protein, subfamily 1A, 1 (Ikaros) | −2.283931088 | −71.06547619 | 31.1154205 | 0.76491 | 29.78182691 | BG540504 | ZNFN1A1 |
| 202130_at | sudD suppressor of bimD6 homolog (*A. nidulans*) | −2.253177267 | −217.4464286 | 96.50657842 | 0.73246 | 29.78182691 | AW006290 | SUDD |
| 201019_s_at | eukaryotic translation initiation factor 1A | −2.244661166 | −41.79333333 | 18.61899424 | 0.7745 | 29.78182691 | NM_001412.1 | EIF1A |
| 212849_at | axin 1 | −2.236240843 | −31.3875 | 14.03583165 | 0.70249 | 29.78182691 | AA745954 | AXIN1 |
| 200994_at | importin 7 | −2.235560442 | −25.42880952 | 11.37469113 | 0.7728 | 29.78182691 | AL137335.1 | IPO7 |
| 210031_at | CD3Z antigen, zeta polypeptide (TiT3 complex) | −2.211406408 | −166.7761905 | 75.41634585 | 0.78116 | 30.8268033 | J04132.1 | CD3Z |
| 202126_at | PRP4 pre-mRNA processing factor 4 homolog B (yeast) | −2.199641085 | −26.2397619 | 11.92911066 | 0.78788 | 30.8268033 | AA156948 | PRPF4B |
| 208754_s_at | nucleosome assembly protein 1-like 1 | −2.133630359 | −33.25785714 | 15.58745028 | 0.78741 | 35.32959479 | AL162068.1 | NAP1L1 |
| 214214_s_at | complement component 1, q subcomponent binding protein | −2.113610624 | −20.52369048 | 9.710251377 | 0.79095 | 35.32959479 | AU151801 | C1QBP |

TABLE 3

Early Parkinson's Disease Genes

Input Parameters

| | |
|---|---|
| Imputation Engine | 10-Nearest Neighbor Imputer |
| Data Type | Two Class, unpaired data |
| Data in log scale? | FALSE |
| Number of Permutations | 100 |
| Blocked Permutation? | FALSE |
| RNG Seed | 1234567 |
| (Delta, Fold Change) | (0.32042, 1.35000) |
| (Upper Cutoff, Lower Cutoff) | (?, −2.43032) |

Computed Quantities

| | |
|---|---|
| Computed Exchangeability Factor S0 | 5.147539566 |
| S0 percentile | 0 |
| False Significant Number (Median, 90 percentile) | (3.80574, 11.41721) |
| False Discovery Rate (Median, 90 percentile) | (18.12255, 54.36765) |
| Pi0Hat | 0.95143 |

21 Negative Significant Genes

| Row | Affymetrix probe set | Gene ID | Score(d) | Numerator(r) | Denominator(s + s0) | Fold Change | q-value (%) | Accession# | Gene symbol |
|---|---|---|---|---|---|---|---|---|---|
| 3 | 200615_s_at | "adaptor-related protein complex 2, beta 1 subunit" | −3.126493123 | −48.19380952 | 15.41465393 | 0.63161 | 18.12255094 | AL567295 | AP2B1 |

TABLE 3-continued

Early Parkinson's Disease Genes

| | | | | | | | | | |
|---|---|---|---|---|---|---|---|---|---|
| 7 | 203677_s_at | TAR (HIV) RNA binding protein 2 | −3.025323771 | −53.09666667 | 17.55073859 | 0.61709 | 18.12255094 | NM_004178.2 | TARBP2 |
| 33 | 212829_at | "*Homo sapiens* cDNA FLJ13267 fis, clone OVARC1000964." | −2.97461471 | −426.9195238 | 143.5209482 | 0.63076 | 18.12255094 | BE878277 | — |
| 96 | 217748_at | CGI-45 protein | −2.774965114 | −651.6533333 | 234.8329822 | 0.61098 | 18.12255094 | NM_015999.1 | CGI-45 |
| 68 | 211546_x_at | "synuclein, alpha (non A4 component of amyloid precursor)" | −2.761667078 | −261.3909524 | 94.64969707 | 0.42219 | 18.12255094 | L36674.1 | SNCA |
| 103 | 215438_x_at | G1 to S phase transition 1 | — 2.703343946 | — 364.5219048 | 134.8411124 | 0.54603 | 18.12255094 | BE906054 | GSPT1 |
| 13 | 217140_s_at | — | −2.689144169 | −44.23142857 | 16.44814327 | 0.67918 | 18.12255094 | AJ002428 | — |
| 29 | 208667_s_at | suppression of tumorigenicity 13 (colon carcinoma) (Hsp70 interacting protein) | −2.66798907 | −68.20238095 | 25.54588691 | 0.67837 | 18.12255094 | U17714.1 | ST13 |
| 64 | 212973_at | ribose 5-phosphate isomerase A (ribose 5-phosphate epimerase) | −2.638505675 | −124.7561905 | 47.28289639 | 0.58481 | 18.12255094 | AI692341 | RPIA |
| 9 | 203718_at | neuropathy target esterase | −2.636425524 | −49.02428571 | 18.59498221 | 0.72872 | 18.12255094 | NM_006702.1 | NTE |
| 5 | 208666_s_at | suppression of tumorigenicity 13 (colon carcinoma) (Hsp70 interacting protein) | −2.589327182 | −33.49047619 | 12.93404574 | 0.67764 | 18.12255094 | U17714.1 | ST13 |
| 132 | 204466_s_at | "synuclein, alpha (non A4 component of amyloid precursor)" | −2.57234729 | −1358.392381 | 528.0750334 | 0.45247 | 18.12255094 | BG260394 | SNCA |
| 105 | 39729_at | peroxiredoxin 2 | −2.557890898 | −161.9919048 | 63.33026358 | 0.68445 | 18.12255094 | L19185 | PRDX2 |
| 136 | 217736_s_at | heme-regulated initiation factor 2-alpha kinase | −2.546200357 | −284.3647619 | 111.6820054 | 0.66018 | 18.12255094 | NM_014413.2 | HRI |
| 93 | 215684_s_at | ASC-1 complex subunit P100 | −2.537375334 | −107.6819048 | 42.4383036 | 0.64989 | 18.12255094 | AL096741.1 | FLJ21588 |
| 43 | 206050_s_at | ribonuclease/ angiogenin inhibitor | −2.516530496 | −90.97761905 | 36.1520034 | 0.64061 | 18.12255094 | NM_002939.1 | RNH |
| 110 | 206302_s_at | nudix (nucleoside diphosphate linked moiety X)-type motif 4 | −2.496930956 | −168.5461905 | 67.50134203 | 0.43493 | 18.12255094 | NM_019094.1 | NUDT4 |
| 113 | 202974_at | "membrane protein, palmitoylated 1, 55 kDa" | −2.47733583 | −247.7633333 | 100.012009 | 0.66927 | 18.12255094 | NM_002436.2 | MPP1 |
| 39 | 201002_s_at | ubiquitin-conjugating enzyme E2 variant 1 | −2.458030634 | −96.91142857 | 39.42645272 | 0.73692 | 18.12255094 | U39361.1 | UBE2V1 |
| 189 | 211560_s_at | cytochrome b5 outer mitochondrial membrane precursor | −2.455018755 | −1320.452857 | 537.8585621 | 0.32758 | 18.12255094 | AF130113.1 | CYB5-M |
| 40 | 218723_s_at | RGC32 protein | −2.430316919 | −52.30714286 | 21.52276621 | 0.64138 | 18.12255094 | NM_014059.1 | RGC32 |

TABLE 4

Progressive Supranuclear Palsy Genes

Input Parameters

| | |
|---|---|
| Imputation Engine | 10-Nearest Neighbor Imputer |
| Data Type | Two Class, unpaired data |
| Data in log scale? | FALSE |
| Number of Permutations | 1000 |
| Blocked Permutation? | FALSE |
| RNG Seed | 1234567 |
| (Delta, Fold Change) | (0.61653, 1.25000) |
| (Upper Cutoff, Lower Cutoff) | (3.68605, −3.10478) |

Computed Quantities

| | |
|---|---|
| Computed Exchangeability Factor S0 | 5.776675832 |
| S0 percentile | 0 |
| False Significant Number (Median, 90 percentile) | (0.81201, 4.87208) |
| False Discovery Rate (Median, 90 percentile) | (5.07508, 30.45047) |
| Pi0Hat | 0.81201 |

TABLE 4-continued

Progressive Supranuclear Palsy Genes

6 Positive Significant Genes

| Affymetrix probe set | Gene ID | Score(d) | Numerator(r) | Denominator(s + s0) | Fold Change | q-value (%) | Accession# | Gene symbol |
|---|---|---|---|---|---|---|---|---|
| 202210_x_at | glycogen synthase kinase 3 alpha | 4.095016079 | 164.3809524 | 40.1417111 | 2.02555 | 5.075078812 | NM_019884.1 | GSK3A |
| 221006_s_at | sorting nexin 27 | 3.951692062 | 100.3 | 25.38153237 | 1.65059 | 5.075078812 | NM_030918.1 | SNX27 |
| 216272_x_at | hypothetical protein FLJ13511 | 3.923369065 | 61.8952381 | 15.77604275 | 2.23041 | 5.075078812 | AF209931.1 | 7h3 |
| 213932_x_at | major histocompatibility complex, class I, A | 3.825337431 | 4129.521429 | 1079.518213 | 1.43912 | 5.075078812 | AI923492 | HLA-A |
| 221328_at | claudin 17 | 3.795178505 | 84.26904762 | 22.20423822 | 2.30284 | 5.075078812 | NM_012131.1 | CLDN17 |
| 208872_s_at | likely ortholog of mouse deleted in polyposis 1 | 3.686050606 | 87.94761905 | 23.85957992 | 1.46734 | 5.075078812 | AA814140 | DP1 |

10 Negative Significant Genes

| Gene Name | Gene ID | Score(d) | Numerator(r) | Denominator(s + s0) | Fold Change | q-value (%) | Accession# | Gene symbol |
|---|---|---|---|---|---|---|---|---|
| 202693_s_at | serine/threonine kinase 17a (apoptosis-inducing) | −3.589888923 | −94.16666667 | 26.23108088 | 0.61248 | 5.075078812 | NM_004760.1 | STK17A |
| 214150_x_at | ATPase, H+ transporting, lysosomal 9 kDa, V0 subunit e | −3.552662658 | −394.0428571 | 110.9147969 | 0.68258 | 5.075078812 | BE043477 | ATP6V0E |
| 201312_s_at | SH3 domain binding glutamic acid-rich protein like | −3.527794165 | −322.6 | 91.4452445 | 0.68794 | 5.075078812 | NM_003022.1 | SH3BGRL |
| 200773_x_at | prothymosin, alpha (gene sequence 28) | −3.476011013 | −278.4666667 | 80.11098516 | 0.72943 | 5.075078812 | NM_002823.1 | PTMA |
| 203685_at | B-cell CLL/lymphoma 2 | −3.281574496 | −84.41190476 | 25.72298903 | 0.57338 | 5.075078812 | NM_000633.1 | BCL2 |
| 40189_at | SET translocation (myeloid leukemia-associated) | −3.281286887 | −156.0047619 | 47.54377391 | 0.55794 | 5.075078812 | M93651 | SET |
| 200627_at | unactive progesterone receptor, 23 kD | −3.259403534 | −246.8309524 | 75.7288718 | 0.68266 | 5.075078812 | BC003005.1 | TEBP |
| 204274_at | estrogen receptor binding site associated, antigen, 9 | −3.193523692 | −49.88333333 | 15.62015446 | 0.46876 | 5.075078812 | AA812215 | EBAG9 |
| 200017_at | ribosomal protein S27a | −3.186418884 | −616.4214286 | 193.4527289 | 0.624 | 5.075078812 | NM_002954.1 | RPS27A |
| 218133_s_at | NIF3 NGG1 interacting factor 3-like 1 (*S. pombe*) | −3.104776922 | −67.23095238 | 21.65403637 | 0.31523 | 5.075078812 | NM_021824.1 | NIF3L1 |

TABLE 5

Alzheimer's Disease Genes
AD genes to p-value 9-8-04 for IDF

| Affymetrix probe set | | Gene name | Gene symbol | | |
|---|---|---|---|---|---|
| 204748_at | NM_000963.1 | prostaglandin-endoperoxide synthase 2(prostaglandin G/H synthase and cyclooxygenase) | PTGS2 | Chr: 1q25.2-q25.3 | 6.32248E−06 |
| 219370_at | NM_019845.1 | candidate mediator of the p53-dependent G2 arrest | REPRIMO | Chr: 2q23.3 | 2.54974E−05 |
| 204031_s_at | NM_005016.1 | poly(rC) binding protein 2 | PCBP2 | Chr: 12q13.12-q13.13 | 3.40446E−05 |

TABLE 5-continued

Alzheimer's Disease Genes
AD genes to p-value 9-8-04 for IDF

| Affymetrix probe set | | Gene name | Gene symbol | | |
|---|---|---|---|---|---|
| 206469_x_at | NM_012067.1 | aldo-keto reductase family 7, member A3 (aflatoxin aldehyde reductase) | AKR7A3 | Chr: 1p35.1-p36.23 | 7.10155E−05 |
| 202258_s_at | U50532.1 | hypothetical protein from BCRA2 region | CG005 | Chr: 13q12-q13 | 9.88449E−05 |
| 217819_at | NM_016099.1 | HSPC041 protein | LOC51125 | Chr: 8p11.21 | 0.000106867 |
| 201362_at | AF205218.1 | NS1-binding protein | NS1-BP | Chr: 1q25.1-q31.1 | 0.000130749 |
| 48580_at | U55777 | CpG binding protein | CGBP | Chr: 18q12 | 0.000143491 |
| 203977_at | NM_000116.1 | tafazzin (cardiomyopathy, dilated 3A (X-linked); endocardial fibroelastosis 2; Barth syndrome) | TAZ | Chr: Xq28 | 0.000161459 |
| 204072_s_at | NM_023037.1 | hypothetical protein CG003 | 13CDNA73 | Chr: 13q12.3 | 0.000201365 |
| 218069_at | NM_024096.1 | hypothetical protein MGC5627 | MGC5627 | Chr: 16p11.2 | 0.000209517 |
| 213587_s_at | AI884867 | vacuolar proton-ATPase subunit | LOC155066 | Chr: 7q36.1 | 0.000249003 |
| 213609_s_at | AB023144.1 | seizure related 6 homolog (mouse)-like | SEZ6L | Chr: 22q12.1 | 0.00025434 |
| 212935_at | AB002360.1 | MCF.2 cell line derived transforming sequence-like | MCF2L | Chr: 13q34 | 0.000276869 |
| 200899_s_at | NM_012215.1 | meningioma expressed antigen 5 (hyaluronidase) | MGEA5 | Chr: 10q24.1-q24.3 | 0.000290245 |
| 200677_at | NM_004339.2 | pituitary tumor-transforming 1 interacting protein | PTTG1IP | Chr: 21q22.3 | 0.00030473 |
| 206635_at | NM_000748.1 | cholinergic receptor, nicotinic, beta polypeptide 2 (neuronal) | CHRNB2 | Chr: 1q21.3 | 0.000318311 |
| 208944_at | D50683.1 | transforming growth factor, beta receptor II (70/80 kDa) | TGFBR2 | Chr: 3p22 | 0.000346525 |
| 210225_x_at | AF009635.1 | leukocyte immunoglobulin-like receptor, subfamily B (with TM and ITIM domains), member 3 | LILRB3 | Chr: 19q13.4 | 0.000356823 |
| 213251_at | AV712064 | Homo sapiens mRNA; cDNA DKFZp434C2112 (from clone DKFZp434C2112) | — | — | 0.000375103 |
| 45687_at | AA161130 | hypothetical protein MGC3121 | MGC3121 | Chr: 16p11.2 | 0.00037598 |
| 204392_at | NM_003656.2 | calcium/calmodulin-dependent protein kinase I | CAMK1 | Chr: 3p25.3 | 0.000394752 |
| 201124_at | AL048423 | integrin, beta 5 | ITGB5 | Chr: 3q21.2 | 0.000394779 |
| 221146_at | NM_018532.1 | — | — | — | 0.000414168 |
| 203289_s_at | BE791629 | Conserved gene telomeric to alpha globin cluster | CGTHBA | Chr: 16p13.3 | 0.000420479 |
| 210677_at | AF059203.1 | sterol O-acyltransferase 2 | SOAT2 | Chr: 12q13.13 | 0.000424393 |
| 220352_x_at | NM_024305.1 | hypothetical protein MGC4278 | MGC4278 | Chr: 16 | 0.000427682 |
| 209238_at | BE966922 | syntaxin 3A | STX3A | Chr: 11q12.1 | 0.000468537 |
| 204122_at | NM_003332.1 | TYRO protein tyrosine kinase binding protein | TYROBP | Chr: 19q13.1 | 0.000474222 |
| 201502_s_at | AI078167 | nuclear factor of kappa light polypeptide gene enhancer in B-cells inhibitor, alpha | NFKBIA | Chr: 14q13 | 0.000474846 |
| 221353_at | NM_002550.1 | olfactory receptor, family 3, subfamily A, member 1 | OR3A1 | Chr: 17p13.3 | 0.000493924 |
| 204906_at | BC002363.1 | ribosomal protein S6 kinase, 90 kDa, polypeptide 2 | RPS6KA2 | Chr: 6q27 | 0.00053106 |
| 215284_at | AF070575.1 | Homo sapiens clone 24407 mRNA sequence | — | — | 0.000544628 |
| 208110_x_at | NM_030973.1 | hypothetical protein TCBAP0758 | TCBAP0758 | Chr: 19q13.3 | 0.000547495 |
| 201323_at | NM_006824.1 | EBNA1 binding protein 2 | EBNA1BP2 | Chr: 1p35-p33 | 0.000561192 |
| 218909_at | NM_012424.1 | ribosomal protein S6 kinase, 52 kDa, polypeptide 1 | RPS6KC1 | Chr: 1q41 | 0.000558139 |
| 202128_at | NM_014821.1 | KIAA0317 gene product | KIAA0317 | Chr: 14q24.2 | 0.000586757 |
| 203550_s_at | NM_006589.1 | chromosome 1 open reading frame 2 | C1orf2 | Chr: 1q21 | 0.000600338 |
| 208729_x_at | D83043.1 | major histocompatibility complex, class I, B | HLA-B | Chr: 6p21.3 | 0.000601363 |
| 38149_at | D29642 | KIAA0053 gene product | KIAA0053 | Chr: 2p13.2 | 0.000607794 |
| 201371_s_at | AF062537.1 | cullin 3 | CUL3 | Chr: 2q36.3 | 0.000633371 |
| 200070_at | BC001393.1 | hypothetical protein CGI-57 | CGI-57 | Chr: 2q35 | 0.000666382 |
| 201071_x_at | NM_012433.1 | splicing factor 3b, subunit 1, 155 kDa | SF3B1 | Chr: 2q33.1 | 0.000711759 |
| 209176_at | AK001135.1 | Sec23-interacting protein p125 | P125 | Chr: 10q25-q26 | 0.000764806 |
| 212177_at | AL080186.1 | ESTs, Moderately similar to SR rich protein [Homo sapiens] [H. sapiens] | — | — | 0.000776339 |
| 213017_at | AL534702 | abhydrolase domain containing 3 | ABHD3 | Chr: 18q11.1 | 0.000803988 |
| 213205_s_at | AU159543 | KIAA0809 protein | SRISNF2L | Chr: 3p21.31 | 0.000811954 |
| 210784_x_at | AF009634.1 | leukocyte immunoglobulin-like receptor, subfamily B (with TM and ITIM domains), member 3 | LILRB3 | Chr: 19q13.4 | 0.00081537 |
| 218453_s_at | NM_018452.1 | chromosome 6 open reading frame 35 | C6orf35 | Chr: 6q25.3 | 0.00082292 |
| 201944_at | NM_000521.2 | hexosaminidase B (beta polypeptide) | HEXB | Chr: 5q13 | 0.00082772 |
| 212887_at | AI753659 | Sec23 homolog A (S. cerevisiae) | SEC23A | Chr: 14q13.2 | 0.000833993 |
| 221000_s_at | NM_030929.1 | hypothetical protein FKSG28 | FKSG28 | Chr: 10q24.31 | 0.000849443 |
| 202181_at | NM_014734.1 | KIAA0247 gene product | KIAA0247 | Chr: 14q24.1 | 0.000900183 |
| 218356_at | NM_013393.1 | FtsJ homolog 2 (E. coli) | FTSJ2 | Chr: 7p22 | 0.000907562 |
| 203859_s_at | NM_002579.1 | paralemmin | PALM | Chr: 19p13.3 | 0.000915165 |
| 204982_at | NM_014776.1 | G protein-coupled receptor kinase-interactor 2 | GIT2 | Chr: 12q24.1 | 0.00092724 |
| 214585_s_at | AL390171.1 | SAC2 suppressor of actin mutations 2-like (yeast) | SACM2L | Chr: 6p21.3 | 0.000936074 |
| 203462_x_at | NM_003751.1 | eukaryotic translation initiation factor 3, subunit 9 eta, 116 kDa | EIF3S9 | Chr: 7p22.3 | 0.000957623 |
| 207416_s_at | NM_004555.1 | nuclear factor of activated T-cells, cytoplasmic, calcineurin-dependent 3 | NFATC3 | Chr: 16q22.2 | 0.000971427 |
| 210593_at | M55580.1 | spermidine/spermine N1-acetyltransferase | SAT | Chr: Xp22.1 | 0.000979734 |
| 208720_s_at | AI890947 | RNA-binding region (RNP1, RRM) containing 2 | RNPC2 | Chr: 20q11.21 | 0.000994912 |
| 212176_at | AL080186.1 | SR rich protein | DKFZp564B0769 | Chr: 6q16.3 | 0.001040047 |
| 207480_s_at | NM_020149.1 | Meis1, myeloid ecotropic viral integration site 1 homolog 2 (mouse) | MEIS2 | Chr: 15q13.3 | 0.001081415 |
| 218840_s_at | NM_018161.1 | hypothetical protein FLJ10631 | FLJ10631 | Chr: 11q13.2 | 0.00109001 |
| 207349_s_at | NM_022803.1 | uncoupling protein 3 (mitochondrial, proton carrier) | UCP3 | Chr: 11q13 | 0.001109895 |

TABLE 5-continued

Alzheimer's Disease Genes
AD genes to p-value 9-8-04 for IDF

| Affymetrix probe set | | Gene name | Gene symbol | | |
|---|---|---|---|---|---|
| 202474_s_at | NM_005334.1 | host cell factor C1 (VP16-accessory protein) | HCFC1 | Chr: Xq28 | 0.001187725 |
| 218184_at | NM_020245.2 | tubby super-family protein | TUSP | Chr: 6q25-q26 | 0.001196863 |
| 212286_at | AW572909 | KIAA0874 protein | KIAA0874 | Chr: 18p11.21 | 0.001202382 |
| 203618_at | AB023167.1 | Fas apoptotic inhibitory molecule 2 | FAIM2 | Chr: 12q13 | 0.001228528 |
| 215599_at | X83300.1 | SMA4 | SMA4 | Chr: 5q13 | 0.001233795 |
| 208584_at | NM_016432.1 | — | — | — | 0.00124696 |
| 202778_s_at | NM_003453.1 | zinc finger protein 198 | ZNF198 | Chr: 13q11-q12 | 0.001247147 |
| 213817_at | AL049435.1 | Homo sapiens mRNA; cDNA DKFZp586B0220 (from clone DKFZp586B0220) | — | — | 0.001254835 |
| 221529_s_at | AF326591.1 | plasmalemma vesicle associated protein | PLVAP | Chr: 19p13.2 | 0.001263479 |
| 206994_at | NM_001899.1 | cystatin S | CST4 | Chr: 20p11.21 | 0.001263625 |
| 221619_s_at | AF189289.1 | mitochondrial carrier homolog 1 | MTCH1 | Chr: 6pter-p24.1 | 0.001298195 |
| 206947_at | NM_006057.1 | UDP-Gal: betaGlcNAc beta 1,3-galactosyltransferase, polypeptide 5 | B3GALT5 | Chr: 21q22.3 | 0.001316362 |
| 160020_at | Z48481 | matrix metalloproteinase 14 (membrane-inserted) | MMP14 | Chr: 14q11-q12 | 0.001331948 |
| 215074_at | AK022489.1 | myosin IB | MYO1B | Chr: 2q12-q34 | 0.00133769 |
| 209270_at | L25541.1 | laminin, beta 3 | LAMB3 | Chr: 1q32 | 0.001360362 |
| 211458_s_at | AF180519.1 | GABA(A) receptors associated protein like 3 | GABARAPL3 | Chr: 15q26.1 | 0.001371382 |
| 210799_at | M81590.1 | 5-hydroxytryptamine (serotonin) receptor 1B | HTR1B | Chr: 6q13 | 0.00143842 |
| 220111_s_at | NM_020373.1 | chromosome 12 open reading frame 3 | C12orf3 | Chr: 12p13.3 | 0.001474657 |
| 202463_s_at | NM_003926.4 | methyl-CpG binding domain protein 3 | MBD3 | Chr: 19p13.3 | 0.001513929 |
| 203292_s_at | NM_021729.2 | vacuolar protein sorting 11 (yeast) | VPS11 | Chr: 11q23 | 0.001543169 |
| 211979_at | AK024651.1 | G protein-coupled receptor 107 | GPR107 | Chr: 9q34.13 | 0.001555205 |
| 212006_at | D87684.1 | UBX domain containing 2 | UBXD2 | Chr: 2q21.2 | 0.001560719 |
| 216040_x_at | AK024135.1 | Homo sapiens cDNA FLJ14073 fis, clone HEMBB1001812. | — | — | 0.001589936 |
| 207951_at | NM_001891.1 | casein beta | CSN2 | Chr: 4q21.1 | 0.001597309 |
| 201478_s_at | U59151.1 | dyskeratosis congenita 1, dyskerin | DKC1 | Chr: Xq28 | 0.001600453 |
| 201594_s_at | NM_005134.1 | protein phosphatase 4, regulatory subunit 1 | PPP4R1 | Chr: 18p11.21 | 0.001609187 |
| 205423_at | NM_001127.1 | adaptor-related protein complex 1, beta 1 subunit | AP1B1 | Chr: 22q12.2 | 0.001644358 |
| 211932_at | BE867771 | hypothetical protein LOC220988 | LOC220988 | Chr: 2q31.2 | 0.001668192 |
| 216338_s_at | AK021433.1 | DKFZP566C243 protein | DKFZP566C243 | Chr: 6p21.1 | 0.001758194 |
| 204920_at | AF154830.1 | carbamoyl-phosphate synthetase 1, mitochondrial | CPS1 | Chr: 2q35 | 0.001772012 |
| 201604_s_at | NM_002480.1 | protein phosphatase 1, regulatory (inhibitor) subunit 12A | PPP1R12A | Chr: 12q15-q21 | 0.001798102 |
| 218865_at | NM_022746.1 | hypothetical protein FLJ22390 | FLJ22390 | Chr: 1q42.11 | 0.001805003 |
| 201247_at | BE513151 | sterol regulatory element binding transcription factor 2 | SREBF2 | Chr: 22q13 | 0.00182078 |
| 221947_at | BF112057 | interleukin 17 receptor C | IL-17RC | Chr: 3p25.3 | 0.001821911 |
| 213301_x_at | AL538264 | transcriptional intermediary factor 1 | TIF1 | Chr: 7q32-q34 | 0.001825354 |
| 212820_at | AB020663.1 | rabconnectin-3 | RC3 | Chr: 15q15.3 | 0.001836203 |
| 202274_at | NM_001615.2 | actin, gamma 2, smooth muscle, enteric | ACTG2 | Chr: 2p13.1 | 0.001891885 |
| 201714_at | NM_001070.1 | tubulin, gamma 1 | TUBG1 | Chr: 17q21 | 0.001897065 |
| 216009_at | U92027.1 | Homo sapiens, clone IMAGE: 4776814, mRNA | — | — | 0.001914452 |
| 215413_at | AK023832.1 | likely ortholog of mouse exocyst component protein 70 kDa homolog (S. cerevisiae) Exo70: exocyst component protein 70 kDa homolog (S. cerevisiae) | EXO70 | Chr: 17q25.3 | 0.001933923 |
| 215408_at | AK025072.1 | Homo sapiens cDNA: FLJ21419 fis, clone COL04084. | — | — | 0.001939356 |
| 211893_x_at | U66145.1 | CD6 antigen | CD6 | Chr: 11q13 | 0.001940368 |
| 216372_at | AF103295.1 | — | — | — | 0.001944136 |
| 201369_s_at | NM_006887.1 | zinc finger protein 36, C3H type-like 2 | ZFP36L2 | Chr: 2p22.3-p21 | 0.001969637 |
| 216354_at | AL031669 | — | — | — | 0.002004068 |
| 220066_at | NM_022162.1 | caspase recruitment domain family, member 15 | CARD15 | Chr: 16p12-q21 | 0.002020765 |
| 205075_at | NM_000934.1 | serine (or cysteine) proteinase inhibitor, clade F (alpha-2 antiplasmin, pigment epithelium derived factor), member 2 | SERPINF2 | Chr: 17p13 | 0.002051338 |
| 200679_x_at | BE311760 | high-mobility group box 1 | HMGB1 | Chr: 13q12 | 0.002092682 |
| 203760_s_at | U44403.1 | Src-like-adaptor | SLA | Chr: 8q24 | 0.002105136 |
| 217633_at | AW513509 | ESTs, Highly similar to Y539_HUMAN Hypothetical protein KIAA0539 [H. sapiens] | — | — | 0.002165551 |
| 204035_at | NM_003469.2 | secretogranin II (chromogranin C) | SCG2 | Chr: 2q35-q36 | 0.002212856 |
| 216872_at | X91103.1 | Hr44 antigen | HR44 | — | 0.002226376 |
| 203378_at | AB020631.1 | PCF11p homolog | PCF11 | Chr: 11q13 | 0.002226909 |
| 207364_at | NM_001586.1 | chromosome X open reading frame 2 | CXorf2 | Chr: Xq28 | 0.002242084 |
| 207214_at | NM_014471.1 | serine protease inhibitor, Kazal type 4 | SPINK4 | Chr: 9p13.2 | 0.002255836 |

III. Methods of Assaying for Alterations in Gene Expression

Thus, in accordance with the present invention, methods are provided for the assaying of gene expression in patients suffering from or at risk of ND. Applications of this assay are to (a) identify patients whose gene expression profile puts them at risk of developing ND; (b) identify patients whose symptoms are such that they may or may not be suffering from ND (i.e., provide a definitive diagnosis of ND); (c) assess the impact of an ND therapy; (d) monitor ND progression; (e) identify therapeutic targets; (f) identify disease genes (susceptibility genes and genes regulating age-at-onset of the disease); and (g) identify patients with clinical or molecular subtypes of the disease. In each of these assays, the expression of a particular set of genes, set forth in the preceding sections, will be measured. Examples of various techniques include microarray analysis, PCR, real-time PCR, Northern blotting, and in situ hybridization, all of which are well known in the art. The following is a discussion of various aspects of such methods.

1. Hybridization

There are a variety of ways by which one can assess gene expression. These methods either look at protein or at mRNA levels. Methods looking at mRNAs all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Since many nucleic acids, especially mRNAs, are in low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in liis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously (Chamberlan et al., 1990). The presence of many PCR primers in a single tube could cause many problems, such as the increased formation of misprimed PCR products and "primer dimers", the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller and Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR: and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846, 709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[x-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat.

Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA or total RNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3'0 end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

5. Mass Spectrometry

By exploiting the intrinsic properties of mass and charge, mass spectrometry (MS) can resolved and confidently identified a wide variety of complex compounds, including nucleic acids. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). See also U.S. Pat. Nos. 5,622,824; 5,716,825; 5,851,765; 5,869,242; 6,197,498;

6,436,640; 6,500621; 6.602,662; and 6,723,564, each of which are hereby incorporated by reference.

IV. Protein-Based Diagnostic Assays

In other aspects of the invention, one may employ a protein-based diagnostic approach to assess a gene products set forth in Tables 1-5. Applications of this assay are to (a) identify patients whose expression profile puts them at risk of developing ND; (b) identify patients whose symptoms are such that they may or may not be suffering from ND (i.e., provide a definitive diagnosis of ND); (c) assess the impact of an ND therapy; (d) monitor ND progression; (e) identify therapeutic targets; (f) identify disease proteins (susceptibility proteins and proteins regulating age-at-onset of the disease); and (g) identify patients with clinical or molecular subtypes of the disease.

1. Immunodetection

The most common form of protein identification is by the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, Cold Spring Harbor Laboratory, 1988; incorporated herein by reference).

In accordance with the present invention, immunodetection methods are provided. Some immunodetection methods include enzyme linked immunosorbent assay (ELISA), radioimrnunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev (1999); Gulbis and Galand (1993); De Jager et al. (1993); and Nakamura et al. (1987), each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. Patents concerning the use of such labels include U.S. Pat. Nos. 3,817,837; 3,850,752; 3,939,350; 3,996,345; 4,277, 437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine γ globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

2. Mass Spectrometry

By exploiting the intrinsic properties of mass and charge, mass spectrometry (MS) can resolved and confidently identified a wide variety of complex compounds, including nucleic acids. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000).

A. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 µL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

B. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

C. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

D. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

E. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000).

These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multicomponent quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

V. Screening for Modulators of Protein Expression and Function

The present invention further comprises methods for identifying modulators of the expression and/or function of the genes/gene products set forth in Tables 1-5. These assays may comprise random screening of large libraries of candidate substances; alternatively, the assays may be used to focus on particular classes of compounds selected with an eye towards structural attributes that are believed to make them more likely to modulate the expression or function of the target. For example, the enzymatic function of the protein expressed by one of the best markers (UCHL1 RNA), could be modulated by drug-like molecules.

To identify a modulator, one generally will determine the expression or function of a target gene in the presence and absence of the candidate substance, a modulator defined as any substance that alters function. For example, a method generally comprises:

(a) providing a candidate modulator;
(b) admixing the candidate modulator with an isolated cell, tissue or a suitable experimental animal;
(c) measuring expression of one or more gene targets in the cell, tissue or animal of step (c); and
(d) comparing the expression measured in step (c) with the expression of the cell, tissue or animal in the absence of said candidate modulator,
wherein a difference between the measured expression indicates that said candidate modulator is, indeed, a modulator of the expression of the target gene.

It will, of course, be understood that all the screening methods of the present invention are useful in themselves notwithstanding the fact that effective candidates may not be found. The invention provides methods for screening for such candidates, not solely methods of finding them.

As used herein, the term "candidate substance" refers to any molecule that may potentially inhibit or enhance the expression or activity of a gene target or may potentially inhibit or enhance the activity of the protein encoded by such gene. The candidate substance may be a protein or fragment thereof, a small molecule, or even a nucleic acid molecule. It may prove to be the case that the most useful pharmacological compounds will be compounds that are structurally related to the gene target of interest. Using lead compounds to help develop improved compounds is know as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, which have different susceptibility to alteration or which may affect the function of various other molecules. In one approach, one would generate a three-dimensional structure for a target molecule, or a fragment thereof. This could be accomplished by x-ray crystallography, computer modeling or by a combination of both approaches.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

VI. Gene Therapy

In another embodiment, the present invention provides for the administration of a gene therapy vector encoding one or more genes identified (Tables 1-5) as being downregulated in the neurodegenerative diseases set forth above. Alternatively, for genes that are overexpressed in ND, the transgenes may provide for reduced expression of appropriate targets. Various aspects of gene delivery and expression are set forth below.

1. Therapeutic Transgenes

Thus, in accordance with the present invention, there are provided methods of treating ND utilizing genes identified as being overexpressed or underexpressed in ND. By inhibiting or increasing the expression of various of these genes, therapeutic benefit may be provided to patients.

2. Antisense

The term "antisense" nucleic acid refers to oligo- and polynucleotides complementary to bases sequences of a target DNA or RNA. When introduced into a cell, antisense molecules hybridize to a target nucleic acid and interfere with its transcription, transport, processing, splicing or translation. Targeting double-stranded DNA leads to triple helix formation; targeting RNA will lead to double helix formation.

Antisense constructs may be designed to bind to the promoter or other control regions, exons, introns or even exon-intron boundaries of a gene. Antisense RNA constructs, or DNA encoding such antisense RNA's, may be employed to inhibit gene transcription or translation within a host cell. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine in the case of DNA (A:T), or uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" and "antisense sequences" mean nucleic acid sequences that are substantially complementary over their entire length and have very few base mismatches. For example, nucleic acid sequences of fifteen bases in length may be termed complementary when they have complementary nucleotides at thirteen or fourteen positions. Naturally, nucleic acid sequences with are "completely complementary" will be nucleic acid sequences which have perfect base pair matching with the target sequences, i.e., no mismatches. Other sequences with lower degrees of homology are contemplated. For example, an antisense construct with limited regions of high homology, but overall containing a lower degree (50% or less) total homology, may be used.

While all or part of the gene sequence may be employed in the context of antisense construction, statistically, any sequence of 17 bases long should occur only once in the human genome and, therefore, suffice to specify a unique target. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting a gene simply by testing the construct in vitro to determine whether the gene's function or expression is affected.

In certain embodiments, one may wish to employ antisense constructs which include other elements, for example, those which include C-5 propyne pyrimidines. Oligonucleotides which contain C-5 propyne analogs of uridine and cytidine have been shown to bind RNA with high affinity and to be potent inhibitors or gene expression (Wagner et al. 1993).

3. Ribozymes

The term "ribozyme" refers to an RNA-based enzyme capable of targeting and cleaving particular DNA and RNA sequences. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could include modified bases or modified phosphate backbones to improve stability or function.

4. RNA Interference

RNA interference (RNAi) is a form of gene silencing triggered by double-stranded RNA (dsRNA). DsRNA activates post-transcriptional gene expression surveillance mechanisms that appear to function to defend cells from virus infection and transposon activity. Fire et al. (1998); Grishok et al. (2000); Ketting et al. (1999); Lin & Avery (1999); Montgomery et al. (1998); Sharp (1999); Sharp & Zamore (2000); Tabara et al. (1999). Activation of these mechanisms targets mature, dsRNA-complementary mRNA for destruction. $RNA_i$ offers major experimental advantages for study of gene function. These advantages include a very high specificity, ease of movement across cell membranes, and prolonged down-regulation of the targeted gene. Fire et al. (1998); Grishok et al. (2000); Ketting et al. (1999); Lin & Avery (1999); Montgomery et al. (1998); Sharp (1999); Sharp & Zamore (2000); Tabara et al. (1999). Moreover, dsRNA has been shown to silence genes in a wide range of systems, including plants, protozoans, fungi, C. elegans, *Trypanosoma* and *Drosophila*. Grishok et al. (2000); Sharp (1999); Sharp & Zamore (2000).

Several principles are worth note (see Plasterk & Ketting, 2000) First, the dsRNA should be directed to an exon, although some exceptions to this rule have been shown. Second, a homology threshold (probably about 80-85% over 200 bases) is required. Most tested sequences are 500 base pairs or greater. Third, the targeted mRNA is lost after RNA$_i$. Fourth, the effect is non-stoichometric, and thus incredibly potent. In fact, it has been estimated that only a few copies of dsRNA are required to knock down >95% of targeted gene expression in a cell. Fire et al. (1998). Recently, shorter (~20 base pairs) synthetic duplex RNAs have been shown to efficiently perform RNAi, by using liposome transfection. Further, similar short interfering RNA (siRNA) duplexes of 19-25 base pairs have been used by transfection via recombinant DNA constructs containing a promoter for U6 small nuclear RNA (snRNA) to drive nuclear expression of a single RNA transcript. This is also known as the hairpin siRNA/suppression of endogenous RNA (SUPER) strategy and has been shown to eliminate the expression of a target gene in long-term mammalian cell cultures (Brummelkamp et al., 2002; Paul et al., 2002; Lee et al., 2002; Miyagishi et al., 2002).

Although the precise mechanism of RNA$_i$ is still unknown, the involvement of permanent gene modification or the disruption of transcription have been experimentally eliminated. It is now generally accepted that RNA$_i$ acts post-transcriptionally, targeting RNA transcripts for degradation. It appears that both nuclear and cytoplasmic RNA can be targeted. Bosher and Labouesse (2000).

5. Single Chain Antibodies

Naturally-occurring antibodies (of isotype IgG) produced by B cells, consist of four polypeptide chains. Two heavy chains (composed of four immunoglobulin domains) and two light chains (made up of two immunoglobulin domains) are held together by disulphide bonds. The bulk of the antibody complex is made up of constant immunoglobulin domains. These have a conserved amino acid sequence, and exhibit low variability. Different classes of constant regions in the stem of the antibody generate different isotypes of antibody with differing properties. The recognition properties of the antibody are carried by the variable regions (VH and VL) at the ends of the arms. Each variable domain contains three hypervariable regions known as complementarity determining regions, or CDRs. The CDRs come together in the final tertiary structure to form an antigen binding pocket. The human genome contains multiple fragments encoding portions of the variable domains in regions of the immunoglobulin gene cluster known as V, D and J. During B cell development these regions undergo recombination to generate a broad diversity of antibody affinities. As these B cell populations mature in the presence of a target antigen, hypermutation of the variable region takes place, with the B cells producing the most active antibodies being selected for further expansion in a process known as affinity maturation.

A major breakthrough was the generation of monoclonal antibodies, pure populations of antibodies with the same affinity. This was achieved by fusing B cells taken from immunized animals with myeloma cells. This generates a population of immortal hybridomas, from which the required clones can be selected. Monoclonal antibodies are very important research tools, and have been used in some therapies. However, they are very expensive and difficult to produce, and if used in a therapeutic context, can elicit and immune response which will destroy the antibody. This can be reduced in part by humanizing the antibody by grafting the CDRs from the parent monoclonal into the backbone of a human IgG antibody. It may be better to deliver antibodies by gene therapy, as this would hopefully provide a constant localized supply of antibody following a single dose of vector. The problems of vector design and delivery are dealt with elsewhere, but antibodies in their native form, consisting of two different polypeptide chains which need to be generated in approximately equal amounts and assembled correctly are not good candidates for gene therapy. However, it is possible to create a single polypeptide which can retain the antigen binding properties of a monoclonal antibody.

The variable regions from the heavy and light chains (VH and VL) are both approximately 110 amino acids long. They can be linked by a 15 amino acid linker (e.g., (glycine$_4$ serine)$_3$), which has sufficient flexibility to allow the two domains to assemble a functional antigen binding pocket. Addition of various signal sequences allows the scFv to be targeted to different organelles within the cell, or to be secreted. Addition of the light chain constant region (Ck) allows dimerization via disulphide bonds, giving increased stability and avidity. However, there is evidence that scFvs spontaneously multimerize, with the extent of aggregation (presumably via exposed hydrophobic surfaces) being dependent on the length of the glycine-serine linker.

The variable regions for constructing the scFv are obtained as follows. Using a monoclonal antibody against the target of interest, it is a simple procedure to use RT-PCR to clone out the variable regions from mRNA extracted from the parent hybridoma. Degenerate primers targeted to the relatively invariant framework regions can be used. Expression constructs are available with convenient cloning sites for the insertion of the cloned variable regions.

6. Vectors

In accordance with the present invention, both stimulatory and inhibitory genes may be provided to cells of an MS patient and expressed therein. Stimulatory genes are generally simply copies of the gene of interest, although in some cases they may be genes, the expression of which direct the expression of the gene of interest. Inhibitory genes, discussed above, may include antisense or single-chain antibody genes.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

A. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 6 lists non-limiting examples of elements/promoters that may be employed, in the context of the present invention, to regulate the expression of a RNA. Table 7 provides non-limiting examples of inducible elements, which are regions of a nucleic acid sequence that can be activated in response to a specific stimulus.

TABLE 6

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| α$_1$-Antitrypsin | Latimer et al., 1990 |
| H2B (TH2B) Histone | Hwang et al., 1990 |
| Mouse and/or Type I Collagen | Ripe et al., 1989 |

TABLE 6-continued

Promoter and/or Enhancer

| Promoter/Enhancer | References |
|---|---|
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 7

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |

TABLE 7-continued

Inducible Elements

| Element | Inducer | References |
|---|---|---|
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse α2 (XI) collagen (Tsumaki et al., 1998), D1A dopamine receptor gene (Lee et al., 1997), insulin-like growth factor II (Wu et al., 1997), and human platelet endothelial cell adhesion molecule-1 (Almendro et al., 1996).

B. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

C. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

D. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference).

E. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

F. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

G. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

H. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

I. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11, may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

J. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

i) Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

ii) AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

iii) Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one encoding gene of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

iv) Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

v) Delivery Using Modified Viruses

A nucleic acid to be delivered may be housed within an infective virus that has been engineered to express a specific binding ligand. The virus particle will thus bind specifically to the cognate receptors of the target cell and deliver-the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

7. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel and Baltimore, 1987), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

A. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

B. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

C. Calcium Phosphate

In other embodiments of the present invention, a nucleic acid may be introduced to the cells using calcium phosphate precipitation in an ex vivo context. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

D. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

E. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

F. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

G. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0 273 085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

VII. Protein-Based Therapies

Another therapy approach is the provision, to a subject, of an underexpressed protein (per Tables 1-5), synthetic or recombinant, or variants, mimetics or analogs thereof. Alternatively, one could provide a protein that interferes with an overexpressed protein (per Tables 1-5), such as an antibody (single chain, Fab', Fab'$_2$). Formulations would be selected based on the route of administration and purpose including, but not limited to, parenteral formulations, topical formulations, liposomal formulations and classic pharmaceutical preparations for oral administration.

VIII. Pharmaceutical Formulations And Routes Of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an anti-fungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Clinical study. Fifty 50 consecutive PD patients were enrolled that were diagnosed by neurology-board certified movement disorders specialists and that met modified United Kingdom PD Society Brain Bank (UKPDSBB) (Hughes et al., 1992) clinical diagnostic criteria and 55 age-matched consecutive healthy and neurodegenerative disease controls (Table 8) from the Partners Parkinson Center and memory clinic at Massachusetts General Hospital. To keep the number of individuals with a false positive clinical diagnosis of PD at a minimum, the UKPDBB criteria were modified to require the presence of three (instead of only two) cardinal features (bradykinesia, and two of rigidity, rest tremor, postural instability), none of 16 exclusion criteria, and at least 3 of 8 supportive features (Hughes et al., 1992).

TABLE 8

Demographics, clinical phenotypes and hematologic values for PD cases and controls.

| | | Controls (n = 55) | | | | |
|---|---|---|---|---|---|---|
| Diagnostic group | Parkinson's disease (n = 50) | Healthy controls (n = 22) | AD (n = 23) | PSP (n = 6) | Other Controls (n = 4) | P |
| Age at enrollment (years, SD) | 69.4 (8.4) | 64.4 (10.7) | 74.9 (10.3) | 74.5 (9.5) | 73.0 (8.6) | n.s. |
| Number of men (%) | 39 (78%) | 11 (50%) | 8 (35%) | 4 (67%) | 3 (75%) | s. |
| White blood cells (mean, SD) | 6.5 (1.41) | 6.4 ± 1.65 | 6.8 (1.4) | 6.7 (0.9) | 6.1 (0.8) | n.s. |
| Red blood cells | 4.4 ± 0.44 | 4.5 ± 0.36 | 4.5 (0.4) | 4.2 (0.2) | 4.4 (0.2) | n.s. |
| Platelets | 242.8 ± 70.89 | 232.9 ± 60.13 | 250 (64.9) | 252 (135.0) | 209 (45.4) | n.s. |
| Mean corpuscular volume | 89.9 ± 3.93 | 87.1 ± 5.55 | 89.2 (5.0) | 90 (2.9) | 91 (1.0) | n.s. |
| Mean corpuscular hemoglobin | 31.3 ± 1.58 | 29.7 ± 2.69 | 30.4 (1.8) | 31.6 (1.8) | 31.4 (0.1) | n.s. |
| MCHC‡ | 34.8 ± 0.83 | 34.1 ± 1.23 | 34.2 (0.9) | 35.2 (1.2) | 34.5 (0.3) | n.s. |
| Red cell distribution width | 13.6 ± 0.63 | 13.7 ± 1.03 | 13.6 (0.7) | 13.8 (0.4) | 13.7 (1.0) | n.s. |
| Neutrophils | 65.5 ± 8.83 | 57.6 ± 13.06 | 64.3 (10.5) | 62.5 (7.8) | 58.7 (10.0) | n.s. |
| Lymphocytes | 25.4 ± 7.72 | 31.6 ± 11.54 | 26.9 (8.5) | 27.3 (4.3) | 30.3 (9.8) | n.s. |
| Monocytes | 4.9 ± 1.03 | 5.9 ± 1.16 | 5.4 (1.3) | 6.0 (2.7) | 5.0 (1.0) | n.s. |
| Eosinophils | 3.6 ± 2.31 | 4.0 ± 2.59 | 2.3 (1.3) | 3.5 (2.3) | 5.3 (2.1) | n.s. |
| Basophils | 0.7 ± 0.48 | 0.8 ± 0.45 | 0.6 (0.5) | 0.5 (0.6) | 0.7 (0.6) | n.s. |
| Reticulocytes | 1.7 ± 0.54 | 1.8 ± 0.61 | 1.4 (0.4) | 1.8 (0.4) | 1.7 (0.3) | n.s. |
| RNA/tube (μg) | 9.1 ± 3.45 | 9.7 ± 3.14 | 8.0 (3.2) | 11.3 (5.5) | 9.4 (2.3) | n.s. |
| Clinical findings (number, %) | | | | | | |
| resting_tremor | 45 (90%) | | | | | |
| resting_tremor_on enrollment | 33 (66%) | | | | | |
| bradykinesia | 50 (100%) | | | | | |
| rigidity | 49 (98%) | | | | | |
| asymmetric_onset | 45 (90%) | | | | | |
| Postural imbalance | 23 (46%) | | | | | |
| dyskinesias | 11 (22%) | | | | | |
| cognitive_deficit | 15 (30%) | | | | | |
| motor_fluctuation | 16 (32%) | | | | | |
| hallucinations | 7 (14%) | | | | | |
| L-dopa | 31 (62%) | | | 4 (67%) | 2 (50%) | |
| Dopamine agonist | 24 (48%) | | | 2 (50%) | | |
| De novo | 9 (18%) | | | | | |
| Selegiline | 7 (14%) | | | 1 (25%) | | |
| Hoehn and Yahr | 2.3 (0.7) | | | | | |

‡Mean Corpuscular Hemoglobin Concentration;
*includes two patients with MSA, one with CBD, one with ET Healthy controls had no personal or family history of neurodegenerative diseases. Ninety percent of the healthy controls were spouses, thus controlling for environmental biases. Since the prevalence of PD in the elderly is relatively high (~1% at age >65), a previously validated PD screening questionnaire (Rocca et al., 1998) was applied to further reduce the chances of enrolling controls with undiagnosed PD. Exclusion criteria for all study subjects were age <21 years, hematologic malignancies or coagulopathies, known severe anemia (hematocrit <30), and known pregnancy. The study protocol was approved by the Institutional Review Board.

RNA isolation and quality control. Venous blood was collected in PAXgene (PreAnalytiX) tubes and immediately incubated at room temperature for 24 hrs. RNA was then extracted following the PAXgene procedure including DNase treatment. RNA quality was determined by spectrophotometry and by Agilent 2100 Bioanalyzer following the manufacturers rules. RNA passing quality control criteria was used for further analysis.

Microarray procedures. As previously described (Scherzer et al., 2003; 2004), 4 μg of total RNA were used for cDNA synthesis. cRNA was labeled with biotin and hybridized at 45° C. for 16-18 hrs to Affymetrix Human Genome U133A arrays (HG-U133A) Arrays (Affymetrix). The arrays were washed and stained and scanned on an HP Gene Array scanner (Affymetrix). Visual inspection was performed to identify arrays with production defects.

Real-time polymerase chain reaction. Briefly, for genes of interest, TaqMan Assay-on-demand and custom-assay primers and probes were designed using the manufacturer's "rules" including crossing exon junctions (primer/probe information is available upon request). Primers were analyzed for specificity by agarose gel electrophoresis. Glyceraldehyde-3-phosphate dehydrogenase was selected as endogenous control for RNA loading based on low variation in GAPD mRNA levels in the 105 blood samples observed by microarray analysis. To determine relative amplification efficiencies of target and endogenous reference genes, their amplification was assayed in a dilution series according to the manufacturers instructions. Equal efficiencies were defined as slope <0.1 of the plot of log input versus $\Delta$CT. For calibration and generation of standard curves, cDNA prepared from Universal Human Reference RNA (Stratagene) was used. Total RNA (3 μg) was reverse-transcribed into cDNA using TaqMan Reverse Transcription reagents and random hexamers as the primer (Applied Biosystems). Real-time PCR using an ABI Prism 7000 and Taqman kits was performed according to the manufacturers' protocols. No-template (negative) controls containing water substituted for template were run in multiple wells on every reaction plate. For each primer pair age-, sex-, and differential blood count-matched experimental samples and control samples were compared. To control for inter-assay variation, equal amounts of cDNA derived from Universal Reference RNA were spotted on each plate. These assays were highly reproducible with a coefficient of variation of 0.03 for the plate-to-plate control when measured on 6 different 96 well plates run on different days. RNA from each subject was loaded in triplicate or quadruplicate, and the entire experiments were performed twice with similar results.

Microarray data processing. The approach used was previously described (Scherzer et al., 2003; 2004). Briefly, raw CEL files were processed with the MAS5 algorithm performing global scaling with "target intensity" of 100 for all probe sets. Only high quality arrays with GAPD 3'-to-5' prime ratios $\leq$3 and present calls $\geq$4000 were included in the analysis to further reduce noise due to partial RNA degradation or hybridization outliers. Because technical variation is high for genes with low average expression intensities, only genes with intensities of $\geq$100 in at least one sample were considered for further analysis.

Supervised prediction method. The PD risk score is based on van't Veer et al. (2002). Genes in the training set are ranked by their absolute Pearson correlation with the binary class labels, and the top (predicting) genes are used in the marker. A template for each class is formed from the mean values of the discriminating genes. The risk score of a test case is defined as its Pearson correlation with the PD template minus its Pearson correlation with the non-PD template. The number of discriminating genes is picked by maximizing the rank sum of the PD scores in a leave-one-out cross-validation step.

Single gene significance analysis. Stringent significance thresholds were set in order to control for false positive results due to biological and technical noise, and to correct for multiple testing. Requiring—fold changes of at least 1.25 eliminated small changes in expression. To estimate the false discovery rate, permutation analysis (Significance Analysis of Microarrays, SAM; Tusher et al., 2001) was applied. This conservative statistical analysis keeps the number of false positives at a minimum, although the number of false negatives is likely to remain high. The DNA-Chip Analyzer (dChip) package was used to generate graphical representations of relative gene expression levels and to cluster genes. Expression levels were normalized for each gene by setting the average (mean) to 0, and the standard deviation to 1, across all samples. Scaled levels were color coded as a spectrum representing relative changes from the mean using the dChip software package (expression changes higher than the mean are displayed as shades of red and lower than the mean as shades of green).

Statistical analysis. To test for the influence of confounding changes in differential blood cell counts and reticulocyte counts on gene expression signals in PD cases and non-PD controls, multivariate analysis of covariance (MANCOVA) of relevant biological dependent variables was performed (Table 8). Sex, age and PD status were included as factors (PD, sex) and covariates (age) in the MANCOVA.

The third and second tertile odds ratio was the ratio of the odds in favor of PD for a subject with a risk score in the third or second tertile of score values, to the odds in favor of PD for a patient with a score in the first (lowest) tertile. The Cochran-Armitage Linear Trend Test for Proportions was applied to determine the P for trend.

The classical risk factors of PD (age, sex) were included as simultaneous predictors along with the risk score in a logistic regression model predicting the probability of having PD vs. not having PD. Estimates of risk (odds ratios) were calculated on the basis of estimated probabilities and-coefficients from the logistic regression model. The P-value for the relevant parameter was based on a Wald chi-square statistic. For statistical analyses, SAS version 8.2 (SAS Institute Inc.) was used.

Method of building the risk marker in the training set. The 66 samples (individuals with PD, and healthy as well as neurodegenerative disease controls) comprising the "training set" were used to build the risk marker profile. The training set was selected to include about 60% of the subjects (66/105), including 31 randomly selected PD patients, 17 randomly selected healthy subjects, and 18 randomly selected disease controls with either AD or progressive supranuclear palsy (PSP). The remaining ~40% PD and control subjects (39/105) were used as independent test samples.

(1) First, to reduce biological and technical noise, the inventors applied a selective intensity filter to exclude genes with low signal intensities, because false-positive results are particularly high for low-intensity genes. Only genes with signal intensity above the trimmed mean (100) in at least one sample were considered for further analysis. With this criterion, 13968 of the original 22283 genes were selected for further analysis.

(2) To identify the genes whose expression signals correlate with the binary diagnostic categories (PD vs. controls), the Pearson correlation coefficients were calculated. The 13968 genes were then rank-ordered by their descending absolute correlation coefficients. Genes with a greater correlation coefficient are likely candidates for predicting PD risk from gene expression in blood, i.e., risk of PD versus risk of other diagnosis (healthy or diseased control).

Figure 4:
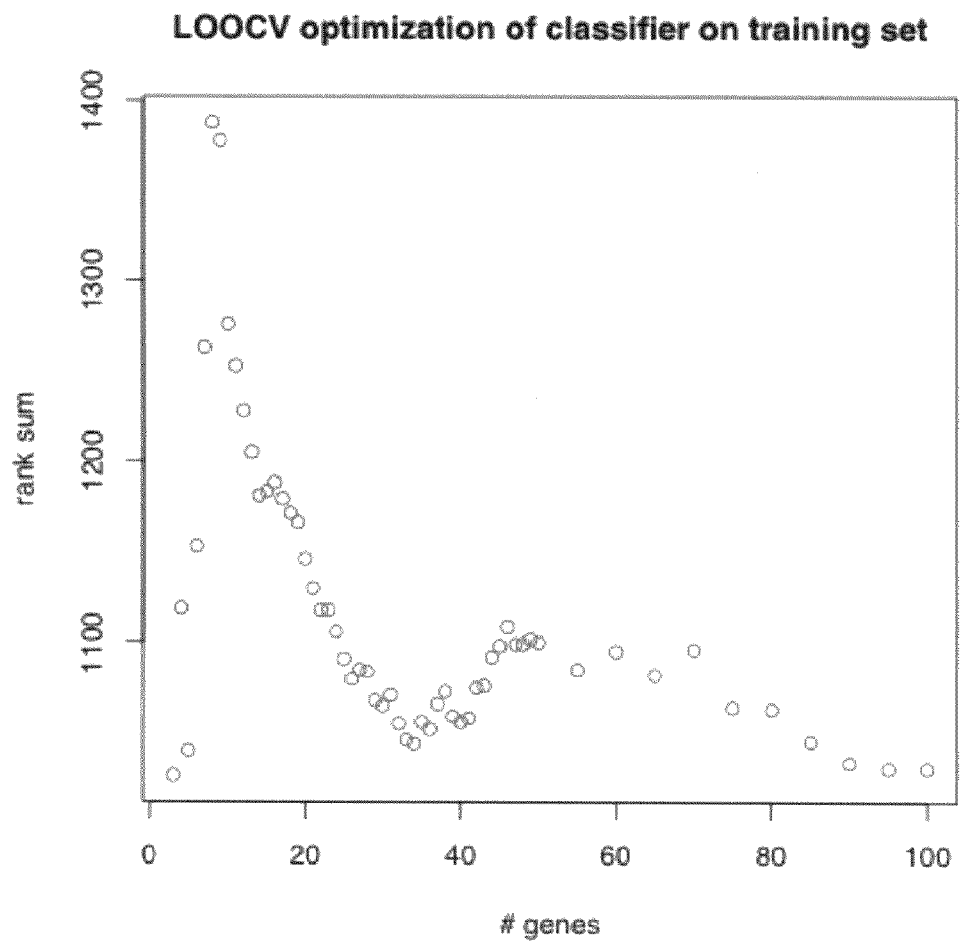
FIG. 4. Performance optimization of the PD risk marker. In a leave-one-out cross validation, the indicated number of genes was used to generate a series of putative risk markers that were applied to the left-out samples. The rank sum of the risk scores for the PD samples was used to assess risk score accuracy. For each iteration one additional marker gene from the top of the rank-ordered candidate list was added. The rank sum was maximized when the optimal number of marker genes was reached ($n_{opt}$=8 genes). Adding marker genes beyond this optimal number did not further improve the rank sum due to the introduction of noise.

(3) In order to optimize the performance of the risk marker, the optimal number of genes for assembling the multigene PD risk marker was determined. A leave-one-out cross validation procedure was used to individually evaluate the performance increasing numbers of genes in the multigene marker. One at a time, each sample in the training set was set aside, and the remaining 65 samples were used as a temporary training set. Within this temporary training set, the inventors re-calculated the Pearson correlation between the diagnostic category (PD vs. controls) and the 13968 genes' expression signal. Genes were rank-ordered by their descending absolute correlation coefficients. The top n genes were picked and calculated their average expression value within the PD samples and the non-PD samples separately, forming a "PD template" and a "non-PD template." Thus, each template is a vector of length n containing the average expression values within its class. The left-out sample was then evaluated by comparing its n genes to the two templates. After each sample was given a risk score (defined below) using the leave-one-out procedure, the rank sum of the scores from PD samples was calculated as an indicator of predictive ability. The rank sum was chosen as a read-out for optimizing the performance of the marker as it avoids introducing arbitrary parameters or cutoffs. For each iteration, one additional marker gene from the top of the candidate list was added. The rank sum was maximized when the optimal number of marker genes was reached ($n_{opt}$=8; FIG. 4). Adding marker genes beyond this optimal number did not further maximize the rank sum due to the introduction of noise.

(4) Next, the performance-optimized top eight genes were picked from the list of 13968 genes rank-ordered by their descending absolute correlation coefficients in the entire training set. Average expression value was calculated within the PD samples and the non-PD samples separately, forming a PD template and a non-PD template. The PD risk score of a sample was defined as the difference of the correlation between the novel sample and the PD template and the correlation between the novel sample and the non-PD template:

PD risk score=(correlation of the novel sample with the PD template)−(correlation of the novel sample with the non-PD template)

Together, the two templates and the scoring method comprise the PD risk marker.

Figure 5A:
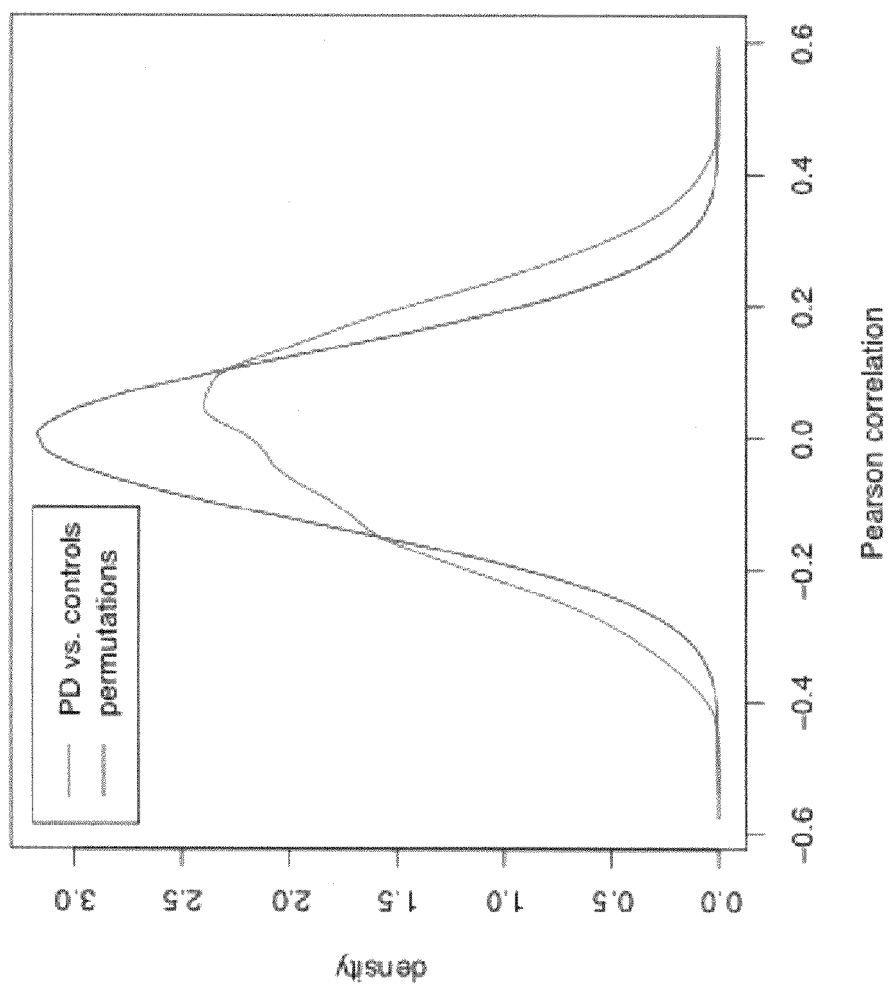
FIGS. 5A-B. Expression changes of the eight marker genes are significantly correlated with PD.
Figure 5B:
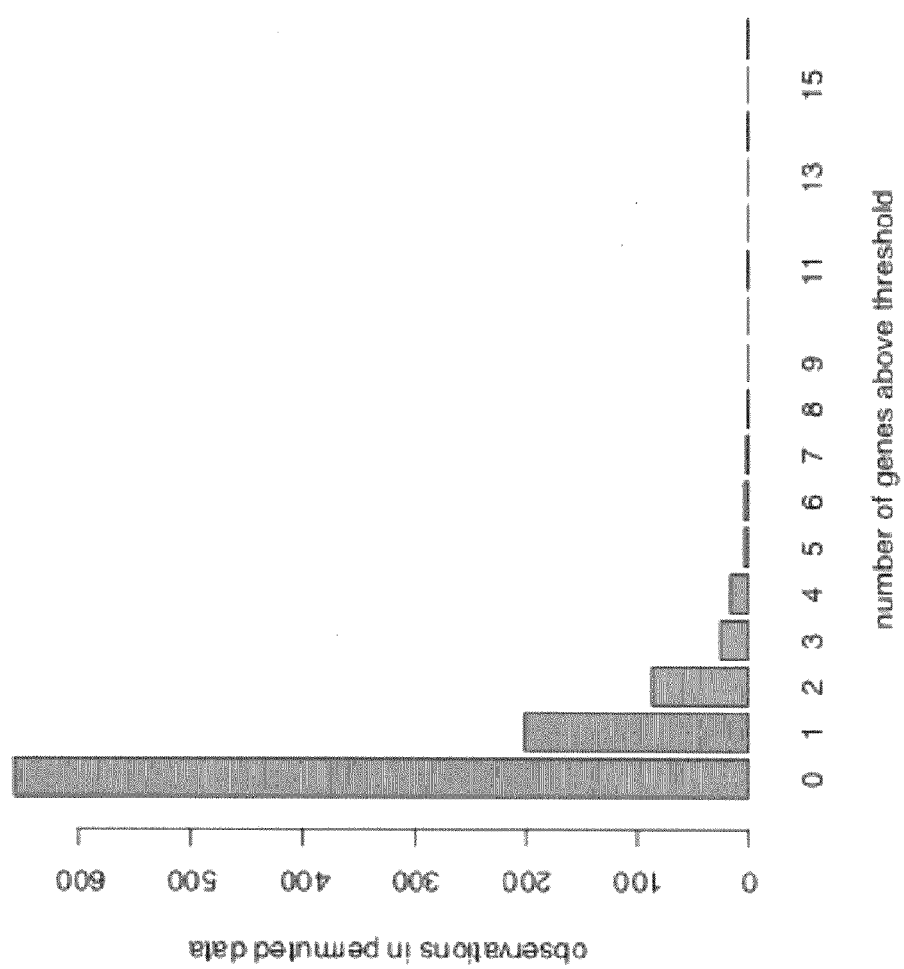

Significance analysis. To estimate whether the eight genes used for the optimized marker were significantly correlated with PD or controls, 1000 random class-label permutations of the data set were performed and calculated correlations between probe sets and class labels. Overall, the permutation correlations were distinctly smaller than the correlations with the true class labels (FIG. 5A). There were only four permutations with eight or more absolute correlations greater than the eight genes in the risk marker. The probability of discovering eight genes with correlations $\geq 0.4725$ purely by chance is estimated to be 0.004 based on 1000 random permutations. On average, there would be less than one gene selected by chance (FIG. 5B).

Leave-one-out cross validation (LOOCV). LOOCV was used to test performance of the PD risk marker in the training set. For LOOCV to be a valid estimate of future prediction performance, care must be taken to avoid an "information leak" in which information about the sample being tested is used to build the marker. To this end, LOOCV was performed such that the risk marker was built entirely from scratch with each leave-one-out iteration, and no parameters were retained between iterations.

One at a time, each sample in the training set was set aside, and the entire training procedure was applied to the remaining 65 samples: (1) first, genes with an intensity above the background (trimmed mean) were selected; (2) genes were rank-ordered by their absolute correlation with the binary prognostic categories; (3) then, the number of genes in the multigene marker was optimized through a (secondary) leave-one-out cross validation step in the "temporary" training set of each iteration (64 samples); (4) the performance-optimized top-ranked genes were used to construct PD and non-PD templates. Finally, the left-out sample was assigned a risk score, which is the correlation between the left-out sample and the PD templates minus the correlation between the left-out sample and the non-PD template.

Satisfyingly, the majority of the LOOCV feature numbers were either eight or nine, with a range of four to 20. Also, 80% of the LOOCV iterations resulted in a risk marker containing all the genes chosen for the full PD risk marker. Thus, the risk marker is robust to removal of individual samples.

Example 2

Results

To identify a transcriptional profile associated with PD, RNA extracted from whole blood of 50 PD patients predominantly at early disease stages (mean Hoehn & Yahr stage 2.3, range 1-4; Table 8), and 55 age-matched controls was probed with 22,283 oligonucleotide probe sets on microarrays. The disease controls included patients with AD that may be misclassified as PD (Hughes et al., 1992), as well as with PSP, multiple system atrophy, and corticobasal degeneration (CBD) that closely mimic the clinical features of PD, but differ in etiology, prognosis, and treatment response. Shifts in differential blood counts that could bias gene expression changes were assayed for and found no significant difference between PD and controls (Table 6).

A subset of the patient samples was randomly chosen to build the risk marker. This "training set" included about 60% of the subjects (66/105), including 31 PD patients, 17 healthy subjects, and 18 disease controls with AD or PSP. A powerful three-step supervised prediction method was used, similar to those used previously (van't Veer et al., 2002) to build a molecular marker for PD. The genes were rank-ordered according to the absolute value of their correlation coefficient with PD. The optimal number of genes for the marker was then determined by sequentially adding genes from the top of this rank-ordered list and evaluating its power for correct prediction accuracy based on the rank sum statistic. The maximum rank sum was reached with an optimal number of eight marker genes (FIG. 4). These marker genes were significantly correlated with PD (FIGS. 5A-B). The inventors then calculated the average expression value of the eight marker genes within the PD samples and the non-PD samples, forming a PD template and a non-PD template. For each sample, a PD risk score was calculated, which was defined as the correlation with the PD templates minus the correlation with the non-PD template.

Figure 1C:
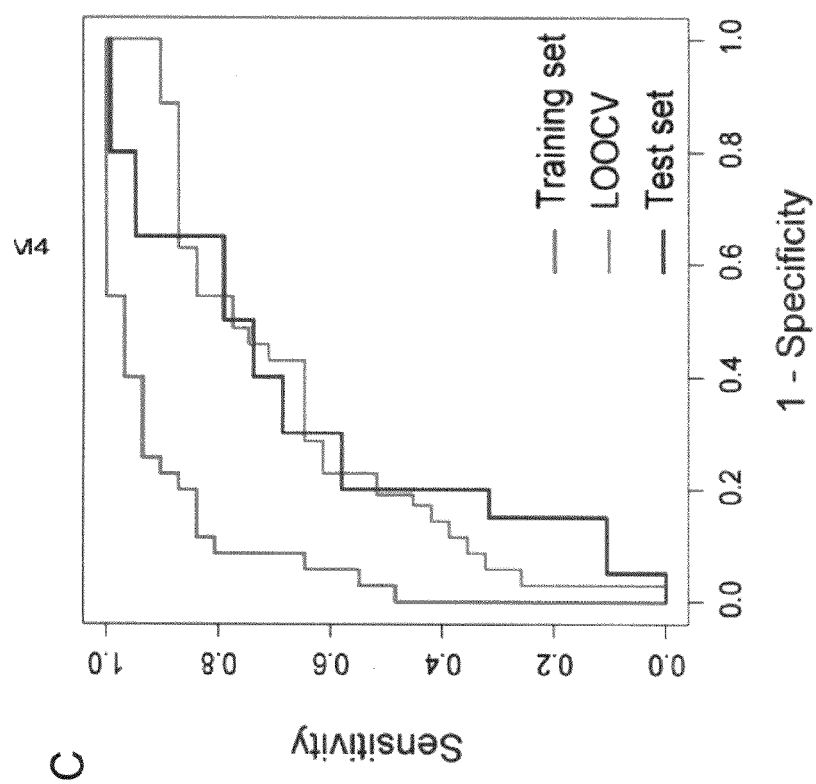

This risk marker correctly ranked 29 out of the 31 PD samples (93%) at the top of the list (high risk scores; FIG. 1A). 26 out of the 35 controls (74%) received low risk scores and were correctly ranked at the bottom of the list. The odds for PD in individuals in the third tertile (high score) and the second tertile (intermediate scores) were compared to the odds for PD in individuals in the first tertile (low scores). The nominal odds ratio for PD of subjects in the third tertile was 210 (95% confidence interval [C.I.] 18-2500) and in the second tertile 18 (95% C.I. 2.0-150) with a P for trend of <0.0001. For novel risk markers the "normal value" that best discriminates high-risk from low-risk individuals is unknown. The inventors therefore determined the receiver-operating-characteristics curve (ROC) of our marker and found high sensitivity and specificity at various cutoffs (FIG. 1C, red line). These estimates are based on the same series of patients that the marker was derived from, and therefore represent an upper limit.

To statistically validate the predictive value of the risk score on future samples a performance leave-one-out cross validation procedure was performed in which the left-out-sample was not involved in selecting the marker genes. The cross-validated odds ratios for PD were 5.7 (95% C.I. 1.6-21) and 2.2 (95% C.I. 0.6-7.8) for persons with scores in the third and second tertile, respectively. This confirmed that high scores correlate with PD risk (P for trend=0.005; Table 9).

TABLE 9

Odds Ratio for Parkinson's Disease According to Tertile of Risk Score

| Variable | N | Risk Score Tertile | | | P for trend |
| --- | --- | --- | --- | --- | --- |
| | | 1 | 2 | 3 | |
| | | Cross-validated odds ratio (95 percent confidence interval)# | | | |
| Training set | PD = 31 Controls = 35 | 1.0 | 2.2 (0.6-7.8) | 5.7 (1.6-7.8) | 0.005 |
| | | Odds ratio (95 percent confidence interval) | | | |
| Test set | PD = 19 Controls = 20 | 1.0 | 1.9 (0.4-9.6) | 5.1 (1-27) | 0.04 |

In each analysis the first tertile served as the reference group.
The cross-validated odds ratio was estimated based on leave-one-out cross-validation results.

Functionally, the eight marker genes do not appear to represent a single biologic pathway or process (FIGS. 1A-D), though all are known to be expressed in the human brain (Rebhan et al., 1997; Kalchman et al., 1997). The products of two of the eight genes, namely huntingtin interacting protein 2 (HIP2) and vitamin D receptor gene (VDR) are of particular interest to PD pathobiology (Kalchman et al., 1996; Wang et al., 2001; Sorkina et al., 2005; Kim et al., 2005). HIP2 encodes a neuronal ubiquitin-conjugating enzyme involved in the ubiquitinylation of huntingtin, mutated in the neurodegenerative disorder Huntington disease (Kalchman et al., 1996). Correspondingly, the ubiquitin-proteasome system is linked to monogenic forms of PD (Scherzer et al., 2004). A polymorphism in the VDR gene is overrepresented in PD patients in Korea (Kim et al., 2005) and in rats the ligand vitamin D ameliorates 6-hydroxydopamine-induced toxicity (Wang et al., 2001). CLTB is implicated in dopamine transporter endocytosis (Sorkina et al., 2005). The remaining five genes have no known role in PD pathogenesis and include CA12 or carbonic anhydrase XII, CEACAM4, a cell adhesion molecule, FPRL2, related to the G-protein-coupled receptor 1 family, ACRV1, initially described in acrosomal vesicles, and UTX, an X-linked gene of unknown function.

Figure 2A:
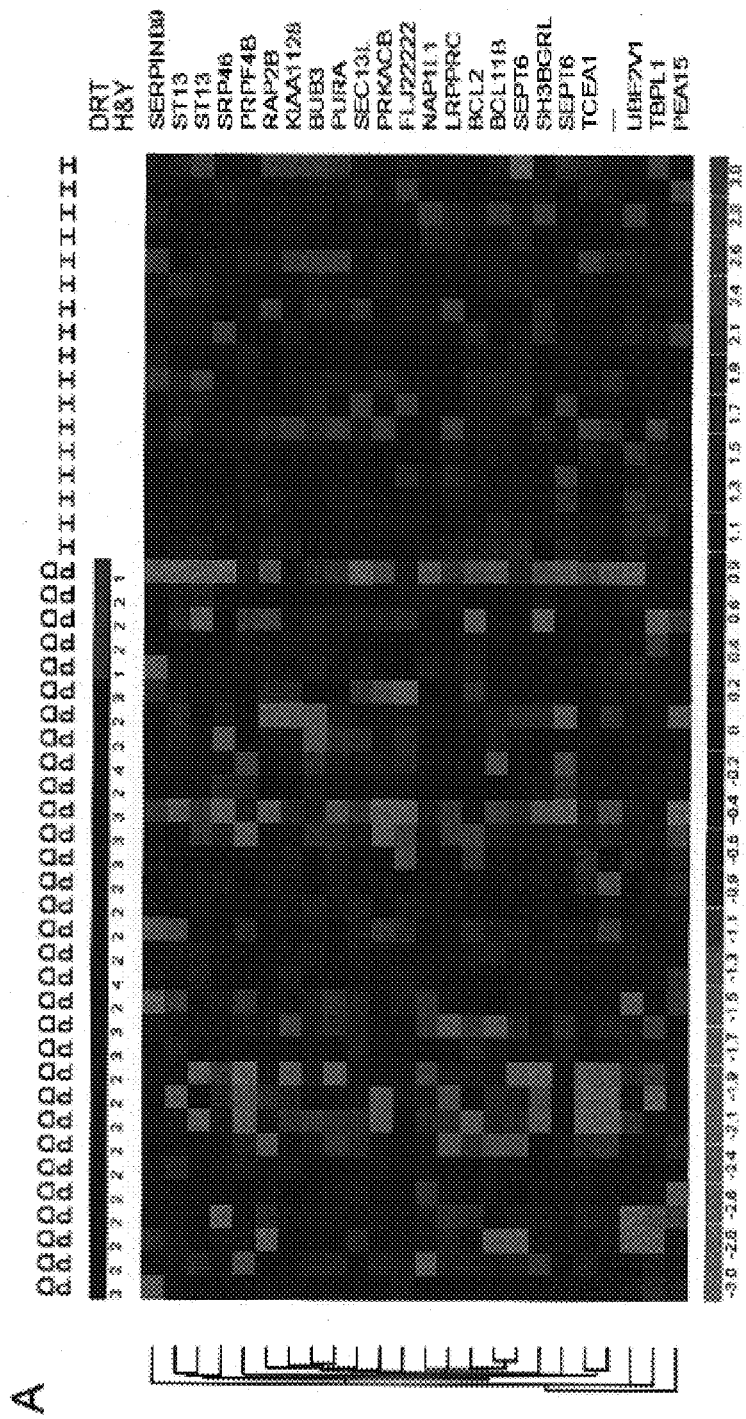
Figure 3A:
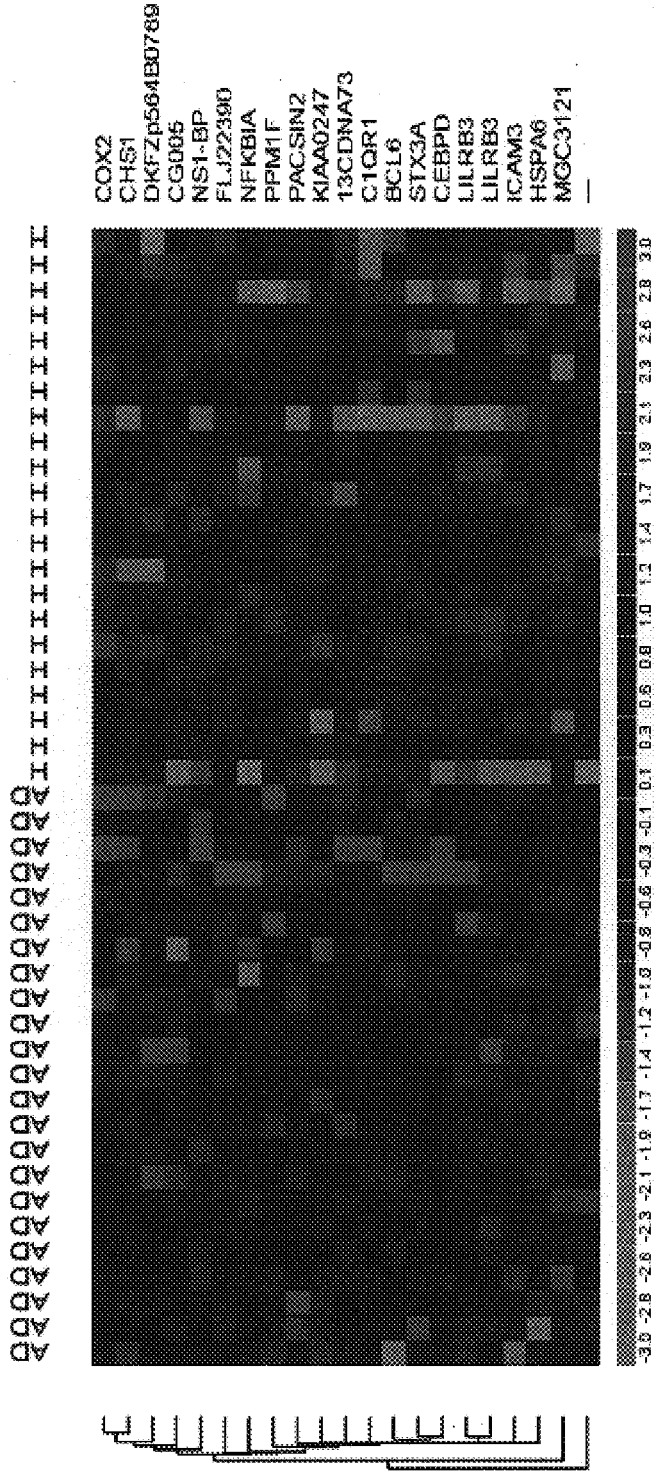
FIGS. 3A-D. Genes differentially expressed in patients with AD or PSP offer insights into disease-linked processes detectable in peripheral blood.
Figure 3B:
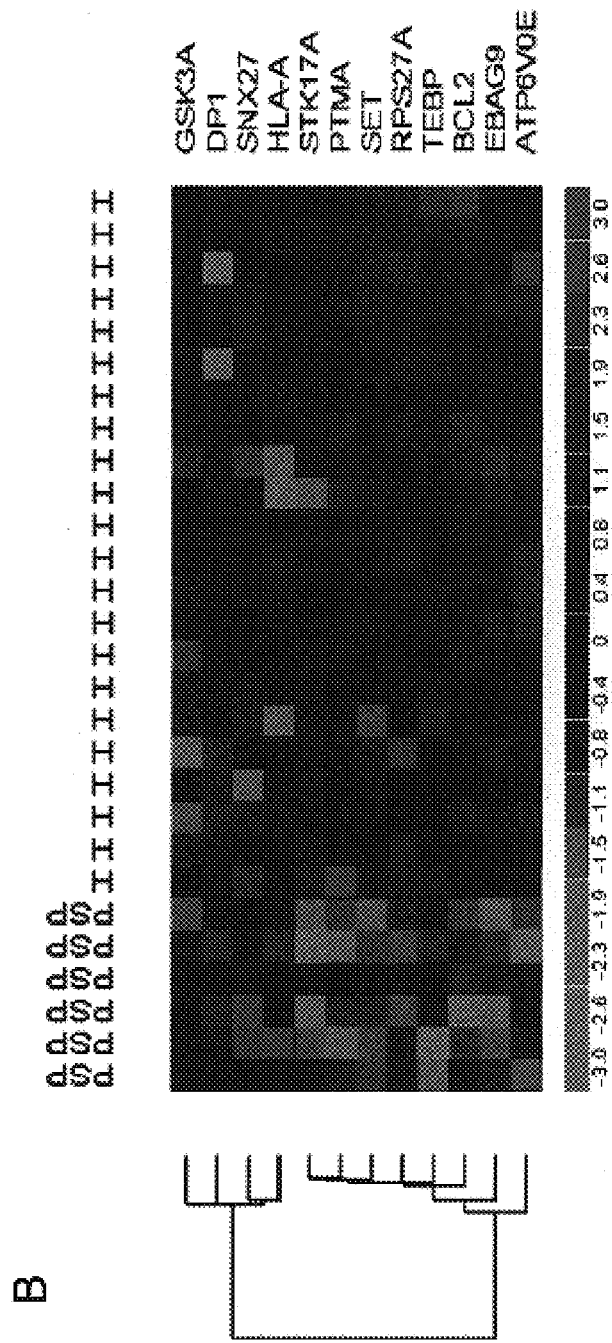
Figure 3C:
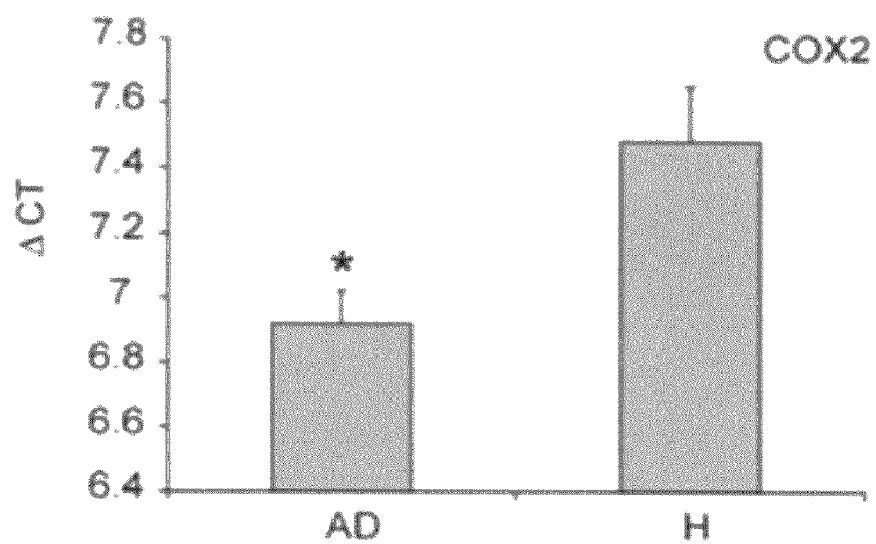
Figure 3D:
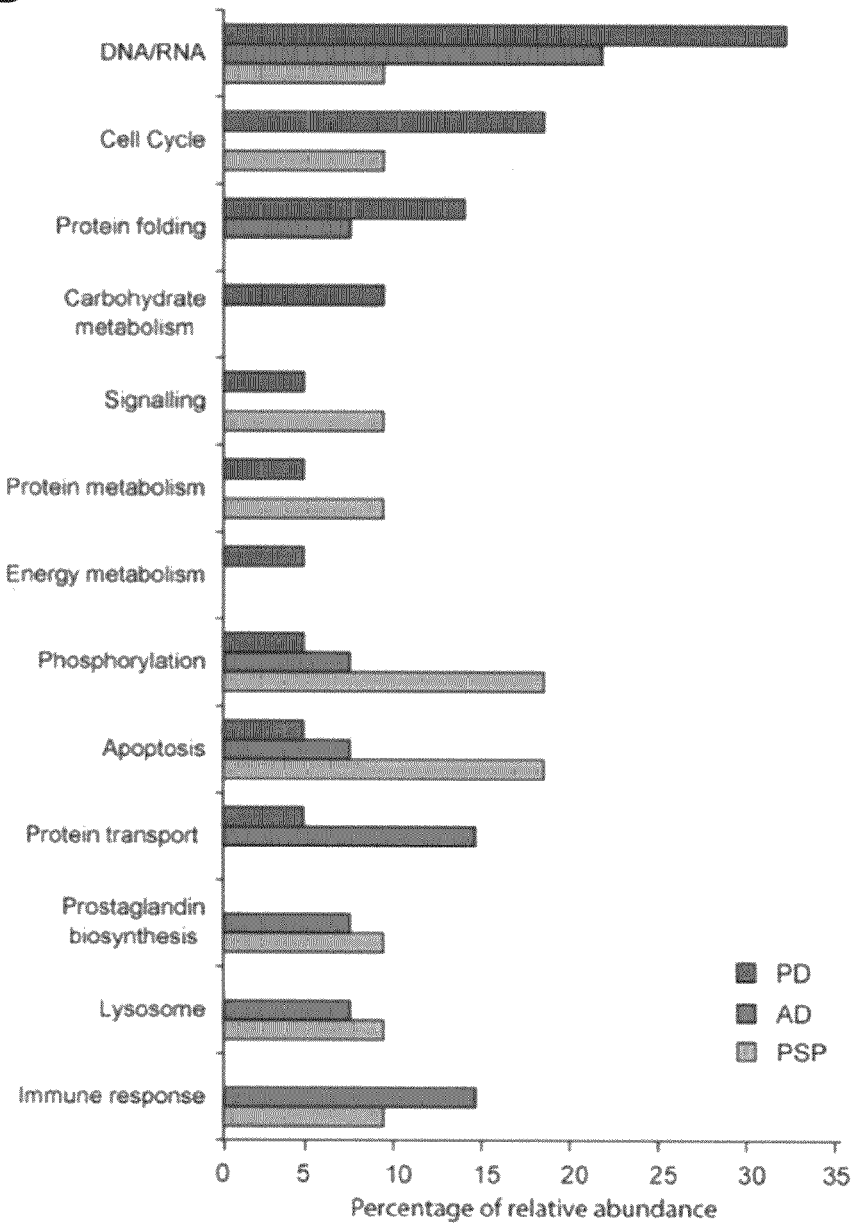

The molecular marker was designed to detect clinically useful gene expression changes that specifically correlate with PD. Discovery of genes dysregulated in PD compared to healthy controls however, regardless of their expression changes in other neurodegenerative diseases, might provide detailed biologic insights into the molecular pathology underlying PD-related changes in blood cells. Significance Analysis of Microarrays (Tusher et al., 2001) identified 22 unique genes that were significantly underexpressed in 31 PD patients (including five de novo PD patients) compared to healthy controls (false discovery rate (FDR) of 0.03; FIGS. 2A-C). Two of these genes, the HSP70-interacting protein (ST13) and UBE2V1, were again involved in the ubiquitin-proteasome pathway. Apoptosis-related genes such as BCL11B were also underexpressed in PD blood cells. A mutation in the gene LRPPRC causes French-Canadian-type-Leigh syndrome, a mitochondrial disease with neurodegeneration in the brainstem (Mootha et al., 2003), the brain region also affected in PD. The changes in mRNA levels for ST13 and BCL11B were confirmed by real time polymerase chain reactions (PCR) in large (n=51 and 45, respectively) age-, sex-, and blood count-matched samples (P=0.025 and P=0.005, respectively by t-test; FIGS. 2B-C). Satisfyingly, all eight genes in the risk marker were among the highly differentially expressed genes in this comparison (top 305 genes by SAM with FDR<0.2; top 228 genes by t-test with P values<0.005) out of all 22,283 genes assayed.

The most rigorous test for the significance and predictive value of a risk marker is validation on independent test samples. The risk score was applied to a test set of 39 samples, including 19 PD patients, five healthy individuals and 15 disease controls with movement or memory disorders. There was a significant difference of scores in patients with PD versus healthy and disease controls (P=0.047 by Wilcoxon). High scores were significantly associated with increased PD risk (P for trend=0.04). Individuals with scores in the third tertile (high score) had an odds ratio for PD of 5.1 (95% C. I. 1-27; Table 9), and individuals with a score in the second tertile (intermediate score) had an odds ratio of 1.9 (95% C. I. 0.4-9.6). The ROC curve in the test set (FIG. 1C, blue line) was highly consistent with the ROC curve for the cross-validated marker in the training set thus confirming the risk prediction observed for different cutoffs.

Figure 1D:
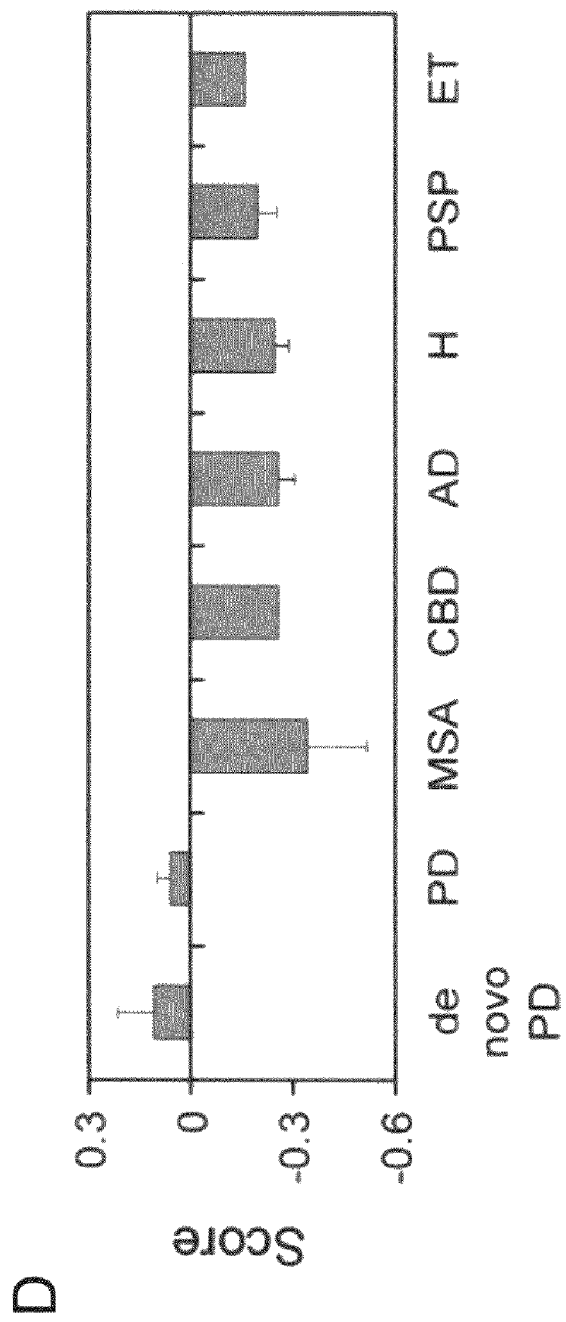

Overall, the risk marker predicted PD beyond the prediction afforded by the traditional risk factors of age and sex (P<0.0001 by Wald chi-square), and was not biased by dopamine replacement therapy (FIG. 1D).

Average scores were positive in treated and de novo PD patients (mean±SE, 0.06±0.04 and 0.11±0.1, respectively). Scores were negative in healthy controls (−0.24±0.04) and all neurodegenerative disease controls analyzed (AD, −0.25±0.05; PSP, −0.19±0.06; MSA, −0.34±0.17; CBD, −0.26; ET, −0.15). Most PD patients receive treatment with L-DOPA or dopamine agonists (dopamine replacement therapy) that ameliorate clinical symptoms without affecting the disease process, while most controls do not (Table 8). Therefore, it was important to determine whether dopamine replacement therapy biases the risk score. The data suggest that dopamine replacement medication does not bias the risk score. There was no difference in risk scores of PD patients on dopamine medication versus unmedicated de novo patients (P=0.96). Furthermore, there was no difference in risk scores in patients treated with distinct classes of PD medications, L-DOPA or dopamine agonists, compared to PD patients not treated with the respective class of medication (P=0.4, and 0.8, respectively). This is consistent with the notion that neither dopamine replacement in general, nor specific classes of dopamine replacement medications affect the risk score.

To determine whether the risk score was independent of the traditional risk factors for PD, sex and age, a logistic regression analysis was performed. Logistic regression analysis of the probability of PD that included the simultaneous markers of age, sex, and the risk score indicated that the risk score predicted PD beyond the prediction afforded by age and sex (P<0.0001 by Wald chi-square). A 0.3 unit increase in the risk score was estimated to increase the odds of PD by a factor of 6 (95% C.I. 2.9-15), holding sex and age constant. Age (or sex) by itself did not predict PD risk in this cohort, holding the risk score and sex (or age) constant (P=0.5 and 0.2, respectively).

In this study design, patients with other neurodegenerative diseases besides PD were included, which allowed the inventors to also examine whether there were differentially expressed genes in blood from these patients (FIG. 3A-D). In particular, 21 genes were found that were differentially transcribed in AD and 12 in PSP, compared to healthy controls with FDR=0.04 and 0.07, respectively. All of the changes in AD involved increased mRNA expression. The gene most highly overexpressed in blood of AD patients (2.2-fold), was COX2 (PTGS2), a prostaglandin cyclooxygenase, that is similarly upregulated in the brain of AD patients (reviewed in Pasinetti, 2002). COX2 is strongly implicated in inflammation in AD based on epidemiologic and molecular studies (reviewed in Pasinetti, 2002). Upregulation of COX2 mRNA was specific for AD compared to 60 non-AD neurodegenerative disease controls (FDR=0.008 by SAM or P=$4 \times 10^{-5}$ by t-test). COX2 mRNA was still significantly elevated in AD blood cells when all subjects on concomitant NSAID therapy (including COX2 inhibitors) where excluded from the analysis (AD, n=12; non-AD controls, n=41; P=$4.7 \times 10^{-7}$ by t-test), suggesting that this was not a medication-induced effect. Finally, the inventors confirmed the increase in COX2 mRNA abundance in blood of AD patients by real-time PCR in 10 AD patients and 7 healthy individuals (FIG. 3C; -fold change 1.4; mean±SE, AD, $\Delta$CT 6.93±0.10; healthy controls, $\Delta$CT 7.48±0.17, P=0.014).

Of the 12 significant transcripts in PSP patient blood (FIG. 3B), glycogen synthase kinase-3 alpha (GSK3A), one of two human GSK3 isoforms and a known tau kinase, was the most highly upregulated gene (>2 fold). GSK3 is associated with neuronal tangles in brain of PSP patients (Ferrer et al., 2002).

The inventors have thus identified a signature associated with PD risk that is embedded in the gene expression changes of PD patients' blood. Combining gene expression scans in cellular blood and linked clinical data will facilitate the rapid characterization of candidate biomarkers as demonstrated here with respect to PD. Large and prospective trials will be needed to precisely assess the clinical utility and predictive value of this molecular marker or derivatives thereof.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,683,202
U.S. Pat. No. 4,684,611
U.S. Pat. No. 4,797,368
U.S. Pat. No. 4,800,159
U.S. Pat. No. 4,883,750
U.S. Pat. No. 4,952,500
U.S. Pat. No. 5,139,941
U.S. Pat. No. 5,242,974
U.S. Pat. No. 5,279,721
U.S. Pat. No. 5,302,523
U.S. Pat. No. 5,322,783
U.S. Pat. No. 5,384,253
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,464,765
U.S. Pat. No. 5,472,672
U.S. Pat. No. 5,527,681
U.S. Pat. No. 5,529,756
U.S. Pat. No. 5,532,128
U.S. Pat. No. 5,538,877
U.S. Pat. No. 5,538,880
U.S. Pat. No. 5,545,531
U.S. Pat. No. 5,550,318
U.S. Pat. No. 5,554,501
U.S. Pat. No. 5,556,752
U.S. Pat. No. 5,561,071
U.S. Pat. No. 5,563,055
U.S. Pat. No. 5,563,055
U.S. Pat. No. 5,571,639
U.S. Pat. No. 5,580,859
U.S. Pat. No. 5,589,466
U.S. Pat. No. 5,591,616
U.S. Pat. No. 5,593,839
U.S. Pat. No. 5,599,695
U.S. Pat. No. 5,610,042

U.S. Pat. No. 5,622,824
U.S. Pat. No. 5,624,711
U.S. Pat. No. 5,656,610
U.S. Pat. No. 5,658,734
U.S. Pat. No. 5,700,637
U.S. Pat. No. 5,702,932
U.S. Pat. No. 5,716,825
U.S. Pat. No. 5,736,524
U.S. Pat. No. 5,757,994
U.S. Pat. No. 5,780,448
U.S. Pat. No. 5,788,166
U.S. Pat. No. 5,789,215
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,765
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,869,242
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,565
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825

U.S. Pat. No. 5,939,291
U.S. Pat. No. 5,942,391
U.S. Pat. No. 5,945,100
U.S. Pat. No. 5,981,274
U.S. Pat. No. 5,986,258
U.S. Pat. No. 5,994,136
U.S. Pat. No. 5,994,624
U.S. Pat. No. 6,004,755
U.S. Pat. No. 6,013,516
U.S. Pat. No. 6,197,498
U.S. Pat. No. 6,436,640
U.S. Pat. No. 6,500,621
U.S. Pat. No. 6,723,564
U.S. Pat. No. 6.602,662
U.S. Pat. No. RE 35,413
Abbondanzo, *Ann. Diagn. Pathol.*, 3(5):318-327, 1999.
Allredetal., *Arch. Surg.*, 125(1):107-113, 1990.
Almendro et al., *J. Immunol.*, 157(12):5411-5421, 1996.
Angel et al., *Mol. Cell. Biol.*, 7:2256, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1994.
Bahn et al., *J. Chem. Neuroanat.*, 22:79-94, 2001.
Bahr et al., *J. Mass Spectrom.*, 32:1111-1116, 1997.
Baichwal and Sugden, In: *Gene Transfer, Kucherlapati (Ed.), NY, Plenum Press*, 117-148, 1986.
Baneiji et al., *Cell*, 27(2 Pt 1):299-308, 1981.
Baneiji et al., *Cell*, 33(3):729-740, 1983.
Bentzley et al., *Anal Chem.*, 68(13):2141-2146, 1996.
Berkhout et al., *Cell*, 59:273-282, 1989.
Blanar et al., *EMBO J*, 8:1139, 1989.
Blomer et al., *J. Virol.*, 71(9):6641-6649, 1997.
Bodine and Ley, *EMBO J*, 6:2997, 1987.
Boshart et al., *Cell*, 41:521, 1985.
Bosher and Labouesse, *Nat. Cell. Biol.*, 2:E31-E36, 2000.
Bosze et al., *EMBO J*, 5(7):1615-1623, 1986.
Braddock et al., *Cell*, 58:269, 1989.
Brown et al. *Immunol. Ser.*, 53:69-82, 1990.
Brumrnelkamp et al., *Science*, 296(5567):550-553, 2002.
Bucknall et al., *J. Am. Soc. Mass Spectrom.*, 13(9):1015-1027, 2002.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Caprioli et al., *Anal. Chem.*, 69:4751, 1997.
Carbonelli et al., *FEMS Microbiol. Lett.*, 177(1):75-82, 1999.
Caronti et al., *Neuroreport.*, 10:2907-2910, 1999.
Celander and Haseltine, *J. Virology*, 61:269, 1987.
Celander et al., *J. Virology*, 62:1314, 1988.
Chabas et al., *Science*, 294:1731-1735, 2001.
Chamberlan et al., In: *PCR Protocols*, Innis et al. (Eds.), Academic Press, NY, 272-281, 1990.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatteijee et al., *Proc. Natl. Acad. Sci. USA*, 86:9114, 1989.
Chaurand et al., *Anal Chem.*, 71(23):5263-5270, 1999.
Chen and Okayama, *Mol. Cell Biol.*, 7(8):2745-2752, 1987.
Chen et al., *Nat. Biotechnol.*, 19:537-542, 2001.
Choi et al., *Cell*, 53:519, 1988.
Citron et al., *Proc. Natl. Acad. Sci. USA*, 91:11993-11997, 1994.
Cocea, *Biotechniques*, 23(5):814-816, 1997.

Cohen et al., *J. Cell. Physiol.*, 5:75, 1987.
Costa et al., *Mol. Cell. Biol.*, 8:81, 1988.
Cotten et al., *Proc. Natl. Acad. Sci. USA*, 89(13):6094-6098, 1992.
Coupar et al., *Gene*, 68:1-10, 1988.
Cripe et al., *EMBO J*, 6:3745, 1987.
Culotta and Hamer, *Mol. Cell. Biol.*, 9:1376, 1989.
Curiel, *Nat. Immun.*, 13(2-3):141-164, 1994.
Dandolo et al., *J. Virology*, 47:55-64, 1983.
De Jager et al., *Semin. Nucl. Med.*, 23(2):165-179, 1993.
De Villiers et al., *Nature*, 312(5991):242-246, 1984.
Deschamps et al., *Science*, 230:1174-1177, 1985.
Desiderio et al., *J. Mass Spectrom.*, 35(6):725-733, 2000.
Desiderio et al., *Methods Mol. Biol.*, 61:57-65, 1996.
Di Luca et al., *Eur. J. Pharmacol.*, 405:277-283, 2000.
Doolittle and Ben-Zeev, *Methods Mol Biol*, 109:215-237, 1999.
Duncan et al., *Rapid Commun. Mass Spectrom.*, 7(12):1090-1094, 1993.
Edbrooke et al., *Mol. Cell. Biol.*, 9:1908, 1989.
Edlund et al., *Science*, 230:912-916, 1985.
European Appln. 0 364 255
European Appln. 273 085
European Appln. 320 308
European Appln. 329 822
Faulstich et al., *Anal. Chem.*, 69(21):4349-4353, 1997.
Feany and Bender, *Nature*, 404: 394-398, 2000.
Fearnley and Lees, *Brain*, 114:2283-2301, 1991.
Fechheimer, et al., *Proc Natl. Acad. Sci. USA*, 84:8463-8467, 1987.
Feng and Holland, *Nature*, 334:6178, 1988.
Fenn et al., *Science*, 246(4926):64-71, 1989.
Ferrer et al., *Acta Neuropathol. (Berl)*, 104:583-591, 2002.
Firak and Subramanian, *Mol. Cell. Biol.*, 6:3667, 1986.
Fire et al., *Nature*, 391(6669):806-811, 1998.
Foecking and Hofstetter, *Gene*, 45(1):101-105, 1986.
Fraley et al., *Proc. Natl. Acad. Sci. USA*, 76:3348-3352, 1979.
Friedmann, *Science*, 244:1275-1281, 1989.
Frohman, In: *PCR Protocols: A Guide To Methods And Applications*, Academic Press, N.Y., 1990.
Fujita et al., *Cell*, 49:357, 1987.
GB Application No. 2 202 328
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gilles et al., *Cell*, 33:717, 1983.
Gloss et al., *EMBO J.*, 6:3735, 1987.
Gobom et al., *Anal. Chem.*, 72(14):3320-3326, 2000.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Gopal, *Mol. Cell Biol.*, 5:1188-1190, 1985.
Graham and Van Der Eb, *Virology*, 52:456-467, 1973.
Greene et al., *Immunology Today*, 10:272, 1989
Grishok et al., *Science*, 287:2494-2497, 2000.
Grosschedl and Baltimore, *Cell*, 41:885, 1985.
Grunhaus and Horwitz, *Seminar in Virology*, 3:237-252, 1992.
Gulbis and Galand, *Hum. Pathol.*, 24(12):1271-1285, 1993.
Harland and Weintraub, *J. Cell Biol.*, 101(3):1094-1099, 1985.
Harlow and Lane, In: *Antibodies: A Laboratory Manual*, Cold Spring Harbor Laboratory, Cold Spring Harbor, N.Y., 346-348, 1988.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horak et al., *Rapid Commun. Mass Spectrom.*, 15(4):241-248, 2001.
Horlick and Benfield, *Mol. Cell. Biol.*, 9:2396, 1989.
Horwich et al. *J. Virol.*, 64:642-650, 1990.
Huang et al., *Cell*, 27:245, 1981.
Hug et al., *Mol. Cell. Biol.*, 8:3065, 1988.
Hughes et al., *J. Neurol. Neurosurg. Psychiatry*, 55:181-184, 1992.
Hwang et al., *Mol. Cell. Biol.*, 10:585, 1990.
Ibarreta et al., *Ann. Neurol.*, 44:216-222, 1998.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc. Natl. Acad. Sci. USA*, 85(24):9436-9440, 1988.
Inouye and Inouye, *Nucleic Acids Res.*, 13: 3101-3109, 1985.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jespersen et al., *Anal Chem.*, 71(3):660-666, 1999.
Jiang et al., *J. Agric. Food Chem.*, 48:3305, 2000.
Johnson et al., *Mol. Cell. Biol.*, 9:3393, 1989.
Kabarle et al., *Anal. Chem.* 65(20):972A-986A, 1993.
Kadesch and Berg, *Mol. Cell. Biol.*, 6:2593, 1986.
Kaeppler et al., *Plant Cell Reports*, 9:415-418, 1990.
Kalchman et al., *J. Biol. Chem.*, 271:19385-19394, 1996.
Kalchman et al., *Nat. Genet.*, 16:44-53, 1997.
Kamme et al., *J. Neurosci.*, 23:3607-3615, 2003.
Kanazawa et al., *Biol. Pharm. Bull.*, 22(4):339-346, 1999.
Kaneda et al., *Science*, 243:375-378, 1989.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kazmaier et al., *Anesthesiology*, 89(4):831-817, 1998.
Kelleher and Vos, *Biotechniques*, 17(6):1110-7, 1994.
Ketting et al., *Cell*, 99(2):133-141, 1999.
Kiledjian et al., *Mol. Cell. Biol.*, 8:145, 1988.
Kim et al., *J. Korean Med. Sci.*, 20:495-498, 2005.
Klamut et al., *Mol. Cell. Biol.*, 10:193, 1990.
Koch et al., *Mol. Cell. Biol.*, 9:303, 1989.
Kraus et al. *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, N.Y., 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86:1173, 1989.
Lareyre et al., *J. Biol. Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Lebkowski et al., *Mol. Cell. Biol.*, 8(10):3988-3996, 1988.
Lee et al., *Biochem. Biophys. Res. Commun.*, 240(2):309-313, 1997.

Lee et al., *Nature Biotechnol.*, 19:500-505, 2002.
Lee et al., *Nature*, 294:228, 1981.
Lee et al., *Nucleic Acids Res.*, 12:4191-206, 1984.
Levenson et al., *Hum. Gene Ther.*, 9(8):1233-1236, 1998.
Levinson et al., *Nature*, 295:79, 1982.
Li et al., *J. Leukoc. Biol.*, 66:567-574, 1999.
Li et al., *Trends Biotechnol.*, 18:151, 2000.
Lin and Avery, *Nature*, 402:128-129, 1999.
Lin et al., *Mol. Cell. Biol.*, 10:850, 1990.
Lovelace et al., *J. Chromatogr.*, 562(1-2):573-584, 1991.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Lynn et al., *J. Mol. Evol.*, 48(5):605-614, 1999.
Macejak and Sarnow, *Nature*, 353:90-94, 1991.
Majors and Varmus, *Proc. Natl. Acad. Sci. USA*, 80:5866, 1983.
Maniatis, et al., *Molecular Cloning, A Laboratory Manual*, Cold Spring Harbor Press, Cold Spring Harbor, N.Y., 1989.
Mann et al., *Cell*, 33:153-159, 1983.
Marie et al., *Anal. Chem.*, 72(20):5106-5114, 2000.
McLaughlin et al., *J. Virol.*, 62(6):1963-1973, 1988.
McNeall et al., *Gene*, 76:81, 1989.
Miketova et al., *Mol. Biotechnol.*, 8(3):249-253, 1997.
Miksicek et al., *Cell*, 46:203, 1986.
Miller et al., *Am. J. Clin. Oncol.*, 15(3):216-221, 1992.
Mirgorodskaya et al., *Rapid Commun. Mass Spectrom.*, 14(14):1226-1232, 2000.
Montgomery et al., *Proc. Natl. Acad. Sci. USA*, 95:15502-15507, 1998.
Mootha et al., *Proc. Natl. Acad. Sci. USA*, 100:605-610, 2003.
Mordacq and Linzer, *Genes and Dev.*, 3:760, 1989.
Moreau et al., *Nucl. Acids Res.*, 9:6047, 1981.
Muddiman et al., *Fres. J. Anal. Chem.*, 354:103, 1996.
Mueller and Wold, *Science*, 246:780-786, 1989.
Muesing et al., *Cell*, 48:691, 1987.
Muzyczka, *Curr. Topics Microbiol. Immunol.*, 158:97-129, 1992.
Nabel and Baltimore, *Nature* 326:711-713, 1987.
Nakamura et al., In: *Handbook of Experimental Immunology* (4th Ed.), Weir et al. (Eds), 1:27, Blackwell Scientific Publ., Oxford, 1987.
Naldini et al., *Science*, 272(5259):263-267, 1996.
Nelson et al., *Anal. Chem.*, 66:1408, 1994.
Ng et al., *Nuc. Acids Res.*, 17:601, 1989.
Nguyen et al., *J. Chromatogr. A.*, 705(1):21-45, 1995.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Ohara et al., *Proc. Natl. Acad. Sci. USA*, 86:5673-5677, 1989.
Omirulleh et al., *Plant Mol. Biol.*, 21(3):415-28, 1993.
Ondek et al., *EMBO J.*, 6:1017, 1987.
Omitz et al., *Mol. Cell. Biol.*, 7:3466, 1987.
Palmiter et al., *Nature*, 300:611, 1982.
Pasinetti, *J. Alzheimers Dis.*, 4:435-445, 2002.
Paskind et al., *Virology*, 67:242-248, 1975.
Paul et al., *Nature Biotechnol.*, 20:505-508, 2002.
PCT Appln. PCT/US87/00880
PCT Appln. PCT/US89/01025
PCT Appln. WO 88/10315
PCT Appln. WO 89/06700
PCT Appln. WO 90/07641
PCT Appln. WO 94/09699
PCT Appln. WO 95/06128
Pech et al., *Mol. Cell. Biol.*, 9:396, 1989.
Pelletier and Sonenberg, *Nature*, 334(6180):320-325, 1988.
Perales et al., *Proc. Natl. Acad. Sci. USA*, 91:4086-4090, 1994.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Rebhan et al., In: *GeneCards: encyclopedia for genes, proteins and diseases*, Rehovot, Israel, 1997.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ridgeway, In: *Vectors: A survey of molecular cloning vectors and their uses*, Rodriguez and Denhardt (Eds.), Stoneham: Butterworth, 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rocca et al., *J. Clin. Epidemiol.*, 51:517-523, 1998.
Roepstorff, *EXS.*, 88:81-97, 2000.
Rosen et al., *Cell*, 41:813, 1988.
Roux et al., *Proc. Natl. Acad. Sci. USA*, 86:9079-9083, 1989.
Sakai et al., *Genes and Dev.*, 2:1144, 1988.
Sambrook et al., In: *Molecular cloning*, Cold Spring Harbor Laboratory Press, Cold Spring Harbor, N.Y., 1989.
Satake et al., *J. Virology*, 62:970, 1988.
Schaffner et al., *J. Mol. Biol.*, 201:81, 1988.
Scherzer and Feany, *Trends Genet.*, 20:273-277, 2004.
Scherzer et al., *Arch Neurol.*, 61:1200-1205, 2004.
Scherzer et al., *Hum. Mol. Genet.*, 12:2457-2466, 2003.
Scherzer et al., In: *Principles of Molecular Neurosurger*, Freese et al. (Eds.), Karger-Basel, 18:1-12, 2003.
Schlossmacher et al., *Neurobiol. Aging*, 13:421-434, 1992.
Searle et al., *Mol. Cell. Biol.*, 5:1480, 1985.
Sharp and Marciniak, *Cell*, 59:229, 1989.
Sharp and Zamore, *Science*, 287:2431-2433, 2000.
Sharp, *Genes Dev.*, 13:139-141, 1999.
Shaul and Ben-Levy, *EMBO J*, 6:1913, 1987.
Sherman et al., *Mol. Cell. Biol.*, 9:50, 1989.
Shin et al., *Mol. Cells*, 10:65-70, 2000.
Sleigh and Lockett, *J. EMBO*, 4:3831, 1985.
Slonim, *Nat. Genet.*, 32(suppl):502-508, 2002.
Sorkina et al., *Traffic*, 6:157-170, 2005.
Spalholz et al., *Cell*, 42:183, 1985.
Spandau and Lee, *J. Virology*, 62:427, 1988.
Spandidos and Wilkie, *EMBO J*, 2:1193, 1983.
Stephens and Hentschel, *Biochem. J*, 248:1, 1987.
Stoeckli et al., *Nat. Med.*, 7(4):493-496, 2001.
Stuart et al., *Nature*, 317:828, 1985.
Sullivan and Peterlin, *Mol. Cell. Biol.*, 7:3315, 1987.
Sunada et al., *Neurosci. Lett.*, 1998;254:180-182, 1998.
Swartzendruber and Lehman, *J. Cell. Physiology*, 85:179, 1975.
Tabara et al., *Cell*, 99(2):123-132, 1999.
Takach et al., *J. Protein Chem.*, 16:363, 1997.
Takebe et al., *Mol. Cell. Biol.*, 8:466, 1988.
Tavernier et al., *Nature*, 301:634, 1983.

Taylor and Kingston, *Mol. Cell. Biol,* 10:165, 1990a.
Taylor and Kingston, *Mol. Cell. Biol.,* 10:176, 1990b.
Taylor et al., *J. Biol. Chem.,* 264:15160, 1989.
Temin, In: *Gene Transfer,* Kucherlapati (Ed.), NY, Plenum Press, 149-188, 1986.
Thiesen et al., *J. Virology,* 62:614, 1988.
Tratschin et al., *Mol. Cell. Biol.,* 4:2072-2081, 1984.
Treisman, *Cell,* 42:889, 1985.
Tronche et al., *Mol. Biol. Med.,* 7:173, 1990.
Trudel and Constantini, *Genes and Dev.,* 6:954, 1987.
Tsumaki et al., *J. Biol. Chem.,* 273(36):22861-22864, 1998.
Tur-Kaspa et al., *Mol. Cell Biol.,* 6:716-718, 1986.
Tusher et al., *Proc. Natl. Acad. Sci. USA,* 98:5116-5121, 2001.
Tyndell et al., *Nuc. Acids. Res.,* 9:6231, 1981.
Vannice and Levinson, *J. Virology,* 62:1305, 1988.
van't Veer et al., *Nature,* 415:530-536, 2002.
Vasseur et al., *Proc Natl. Acad. Sci. USA,* 77:1068, 1980.
Villanueva et al., *Enzyme Microb. Technol.,* 29:99, 1999.
Wagner et al., *Proc. Natl. Acad. Sci. USA* 87(9):3410-3414, 1990.
Wagner et al., *Science,* 260:1510-1513, 1993.
Walker et al., *Nucleic Acids Res.,* 20(7):1691-1696, 1992.
Wang and Calame, *Cell,* 47:241, 1986.
Wang et al., *Anal. Chem.,* 72(21):5285-5289, 2000.
Wang et al., *Brain Res.,* 904:67-75, 2001.
Wang et al., *J. Agric. Food. Chem.,* 47:1549, 1999.
Weber et al., *Cell,* 36:983, 1984.
Weinberger et al. *Mol. Cell. Biol,* 8:988, 1984.
Wilson et al., *Science,* 244:1344-1346, 1989.
Winoto and Baltimore, *Cell,* 59:649, 1989.
Wittliff and Erlander, *Methods Enzymol.,* 356:12-25, 2002.
Wittmann et al., *Biotechnol. Bioeng.,* 72:642, 2001.
Wong et al., *Gene,* 10:87-94, 1980.
Wu and Wu, *Adv. Drug Delivery Rev.,* 12:159-167, 1993.
Wu and Wu, *Biochemistry,* 27:887-892, 1988.
Wu and Wu, *J. Biol. Chem.,* 262:4429-4432, 1987.
Wu et al., *Anal. Chem.,* 70:456A, 1998.
Wu et al., *Biochem. Biophys. Res. Commun.,* 233(1):221-226, 1997.
Wu et al., *Biochim. Biophys. Acta,* 1466:315-327, 2000.
Yang et al., *J. Agric. Food. Chem.,* 48:3990, 2000.
Yutzey et al. *Mol. Cell. Biol.,* 9:1397, 1989.
Zhao-Emonet et al., *Biochim. Biophys. Acta,* 1442(2-3):109-119, 1998.
Zhong et al., *Clin. Chem. ACTA.,* 313:147, 2001.
Zufferey et al., *Nat. Biotechnol.,* 15(9):871-875, 1997.
Zweigenbaum et al., *Anal. Chem.,* 71(13):2294-300, 1999.
Zweigenbaurn et al., *J. Pharm. Biomed. Anal.,* 23(4):723-733, 2000.

What is claimed is:

1. A method of predicting whether a human subject is afflicted with Parkinson's disease (PD) comprising:
    (a) obtaining an mRNA- or protein-containing peripheral blood sample from said subject;
    (b) determining the expression level of ST13 mRNA or protein in said sample;
    (c) comparing the expression level of ST13 mRNA or protein with the expression level of ST13 mRNA or protein in peripheral blood samples from individuals not afflicted with PD; and
    (d) determining decreased expression of ST13 mRNA or protein in the sample from said subject relative to said samples from individuals not afflicted with PD, thereby predicting said subject is afflicted with PD.

2. The method of claim 1, further comprising determining the expression level of one or more genes selected from the group consisting of genes set forth in Tables 2 and 3 in said samples from said subject and said individuals not afflicted with PD.

3. The method of claim 1, further comprising determining the expression level of at least two genes selected from the group consisting of genes set forth in Tables 2 and 3 in said samples from said subject and said individuals not afflicted with PD.

4. The method of claim 1, further comprising determining the expression level of at least three genes selected from the group consisting of genes set forth in Tables 2 and 3 in said samples from said subject and said individuals not afflicted with PD.

5. The method of claim 1, further comprising determining the expression level of at least four genes selected from the group consisting of genes set forth in Tables 2 and 3 in said samples from said subject and said individuals not afflicted with PD.

6. The method of claim 1, further comprising determining the expression level of at least five genes selected from the group consisting of genes set forth in Tables 2 and 3 in said samples from said subject and said individuals not afflicted with PD.

7. The method of claim 1, further comprising determining the expression level of at least six genes selected from the group consisting of genes set forth in Tables 2 and 3 in said samples from said subject and said individuals not afflicted with PD.

8. The method of claim 1, further comprising determining the expression level of at least seven genes selected from the group consisting of genes set forth in Tables 2 and 3 in said samples from said subject and said individuals not afflicted with PD.

9. The method of claim 1, further comprising determining the expression level of at least eight genes selected from the group consisting of genes set forth in Tables 2 and 3 in said samples from said subject and said individuals not afflicted with PD.

10. The method of claim 1, further comprising determining the expression level of at least nine genes selected from the group consisting of genes set forth in Tables 2 and 3 in said samples from said subject and said individuals not afflicted with PD.

11. The method of claim 1, further comprising determining the expression level of 10-20 genes selected from the group consisting of genes set forth in Tables 2 and 3 in said samples from said subject and said individuals not afflicted with PD.

12. The method of claim 1, wherein expression level is determined by multiplex PCR of transcripts.

13. The method of claim 1, wherein expression level is determined by northern blot.

14. The method of claim 1, wherein expression level is determined by reverse transcription PCR (RT-PCR).

15. The method of claim 1, wherein expression level is determined by microarray analysis of mRNA transcripts.

16. The method of claim 1, wherein expression level is determined by RNAse protection.

17. The method of claim 1, wherein expression level is determined by immunohistochemistry, ELISA or western blot.

18. The method of claim 15, wherein microarray analysis comprises use of oligonucleotides that hybridize to mRNA transcripts or cDNAs for ST13, and wherein the oligonucleotides are disposed or directly synthesized on the surface of a chip or wafer.

19. The method of claim 18, wherein said oligonucleotides are about 10 to about 50 nucleotides in length.

* * * * *

UNITED STATES PATENT AND TRADEMARK OFFICE
CERTIFICATE OF CORRECTION

PATENT NO. : 7,595,159 B2 Page 1 of 1
APPLICATION NO. : 11/266774
DATED : September 29, 2009
INVENTOR(S) : Clemens R. Scherzer et al.

It is certified that error appears in the above-identified patent and that said Letters Patent is hereby corrected as shown below:

In column 1, line 10, insert the following paragraph:
--This invention was made with government support under Grant No. AG024816 awarded by the Public Health Services/National Institutes of Health. The government has certain rights in the invention.--.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,595,159 B2
APPLICATION NO. : 11/266774
DATED : September 29, 2009
INVENTOR(S) : Scherzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Seventh Day of December, 2010

David J. Kappos
*Director of the United States Patent and Trademark Office*